United States Patent
March et al.

(10) Patent No.: US 11,771,112 B2
(45) Date of Patent: Oct. 3, 2023

(54) PLANT BASE/ANIMAL CELL HYBRID MEAT SUBSTITUTE

(71) Applicant: EAT SCIFI INC., San Leandro, CA (US)

(72) Inventors: Joshua March, San Francisco, CA (US); Nahyun Cho, Oakland, CA (US); Katherine Gora, Berkeley, CA (US); Dongjun Zhao, Glenview, IL (US)

(73) Assignee: EAT SCIFI INC., San Leandro, CA (US)

( * ) Notice: Subject to any disclaimer, the term of this patent is extended or adjusted under 35 U.S.C. 154(b) by 0 days.

(21) Appl. No.: 18/176,690

(22) Filed: Mar. 1, 2023

(65) Prior Publication Data
US 2023/0189840 A1    Jun. 22, 2023

Related U.S. Application Data

(63) Continuation of application No. PCT/US2022/078365, filed on Oct. 19, 2022.

(60) Provisional application No. 63/283,144, filed on Nov. 24, 2021, provisional application No. 63/257,418, filed on Oct. 19, 2021.

(51) Int. Cl.
| | |
|---|---|
| *A23J 3/04* | (2006.01) |
| *A23J 3/22* | (2006.01) |
| *A23J 3/14* | (2006.01) |
| *C12N 5/077* | (2010.01) |

(52) U.S. Cl.
CPC ............... *A23J 3/227* (2013.01); *A23J 3/04* (2013.01); *A23J 3/14* (2013.01); *C12N 5/0658* (2013.01)

(58) Field of Classification Search
CPC ..... A23J 3/227; A23J 3/04; A23J 3/14; C12N 5/0658; A23L 13/00
USPC .......................................................... 426/657
See application file for complete search history.

(56) References Cited

U.S. PATENT DOCUMENTS

| | | | |
|---|---|---|---|
| 7,270,829 B2 | 9/2007 | Van Eelen | |
| 9,011,949 B2 | 4/2015 | Brown et al. | |
| 9,332,779 B2 | 5/2016 | Marga | |
| 9,526,267 B2 | 12/2016 | Anderson et al. | |
| 9,700,067 B2 * | 7/2017 | Fraser | A23L 13/424 |
| 9,737,875 B2 | 8/2017 | Brown et al. | |
| 9,752,122 B2 | 9/2017 | Marga et al. | |
| 9,808,029 B2 | 11/2017 | Fraser et al. | |
| 9,826,772 B2 | 11/2017 | Fraser et al. | |
| 9,833,768 B2 | 12/2017 | Brown et al. | |
| 9,938,327 B2 | 4/2018 | Shankar et al. | |
| 9,943,096 B2 | 4/2018 | Fraser et al. | |
| 10,039,306 B2 | 8/2018 | Vrljic et al. | |
| 10,087,434 B2 | 10/2018 | Kale et al. | |
| 10,093,913 B2 | 10/2018 | Kale et al. | |
| 10,172,380 B2 | 1/2019 | Varadan et al. | |
| 10,172,381 B2 | 1/2019 | Vrljic et al. | |
| 10,273,492 B2 | 4/2019 | Shankar et al. | |
| 10,287,568 B2 | 5/2019 | Kale et al. | |
| 10,314,325 B2 | 6/2019 | Fraser et al. | |
| 10,327,464 B2 | 6/2019 | Fraser et al. | |
| 10,689,656 B2 | 6/2020 | Shankar et al. | |
| 10,798,958 B2 | 10/2020 | Varadan et al. | |
| 10,863,761 B2 | 12/2020 | Brown et al. | |
| 10,920,196 B2 | 2/2021 | Genovese et al. | |
| 10,986,848 B2 | 4/2021 | Holz-Schietinger et al. | |
| 10,993,462 B2 | 5/2021 | Vrljic et al. | |
| 11,013,250 B2 | 5/2021 | Vrljic et al. | |
| 11,051,532 B2 | 7/2021 | Henderson, Jr. et al. | |
| 2005/0010965 A1 | 1/2005 | Vein | |
| 2006/0029922 A1 | 2/2006 | Van Eelen et al. | |
| 2007/0104901 A1 | 5/2007 | Siegel et al. | |
| 2008/0260913 A1 | 10/2008 | Orcutt et al. | |
| 2010/0011452 A1 | 1/2010 | Tomizuka et al. | |
| 2010/0074998 A1 | 3/2010 | Espeleta Vega et al. | |
| 2010/0166940 A1 | 7/2010 | McMindes et al. | |
| 2011/0301249 A1 | 12/2011 | Challakere | |
| 2013/0274129 A1 | 10/2013 | Katzen et al. | |
| 2014/0193547 A1 | 7/2014 | Brown et al. | |
| 2014/0220217 A1 | 8/2014 | Brown et al. | |
| 2015/0056346 A1 | 2/2015 | Margolis | |
| 2015/0216216 A1 | 8/2015 | Marga | |
| 2015/0289541 A1 | 10/2015 | Brown et al. | |
| 2015/0305390 A1 | 10/2015 | Vrljic et al. | |
| 2015/0366233 A1 | 12/2015 | Brown et al. | |
| 2016/0222054 A1 | 8/2016 | Brown et al. | |
| 2016/0227830 A1 | 8/2016 | Genovese et al. | |
| 2016/0227831 A1 | 8/2016 | Marga | |
| 2016/0340411 A1 | 11/2016 | Fraser et al. | |
| 2017/0035076 A1 | 2/2017 | Geistlinger et al. | |
| 2017/0099856 A1 | 4/2017 | Anderson et al. | |

(Continued)

FOREIGN PATENT DOCUMENTS

| | | |
|---|---|---|
| CN | 101897418 B | 8/2013 |
| EP | 2773223 B1 | 3/2019 |

(Continued)

OTHER PUBLICATIONS

Arye and Levenberg, "Tissue Engineering for Clean Meat Production". Front. Sustain. Food Syst, Jun. 18, 2019; vol. 3, Article 46, 19 pages.

(Continued)

*Primary Examiner* — Hamid R Badr
(74) *Attorney, Agent, or Firm* — Cooley LLP

(57) ABSTRACT

Meat substitute recipes with animal cells and exogenous heme-containing protein on plant-based meat dough matrices are disclosed. Methods of producing are also disclosed.

20 Claims, 20 Drawing Sheets
Specification includes a Sequence Listing.

(56) References Cited

U.S. PATENT DOCUMENTS

| | | |
|---|---|---|
| 2017/0188612 A1 | 7/2017 | Varadan et al. |
| 2017/0342131 A1 | 11/2017 | Fraser et al. |
| 2017/0342132 A1 | 11/2017 | Fraser et al. |
| 2018/0199605 A1 | 7/2018 | Fraser et al. |
| 2018/0199606 A1 | 7/2018 | Fraser et al. |
| 2018/0371469 A1 | 12/2018 | Shankar et al. |
| 2019/0008192 A1 | 1/2019 | Brown et al. |
| 2019/0037893 A1 | 2/2019 | Ajami et al. |
| 2019/0045809 A1 | 2/2019 | Lee et al. |
| 2019/0133162 A1 | 5/2019 | Varadan et al. |
| 2019/0160461 A1 | 5/2019 | Hanyu et al. |
| 2019/0292217 A1 | 9/2019 | Davis et al. |
| 2019/0292555 A1 | 9/2019 | Davis et al. |
| 2019/0338309 A1 | 11/2019 | Vallier et al. |
| 2019/0364948 A1 | 12/2019 | Tetrick et al. |
| 2020/0080050 A1 | 3/2020 | Nahmias |
| 2020/0100525 A1 | 4/2020 | Savir et al. |
| 2020/0140810 A1 | 5/2020 | Ben-Arye et al. |
| 2020/0140821 A1 | 5/2020 | Elfenbein et al. |
| 2020/0236971 A1 | 7/2020 | Audibert et al. |
| 2020/0332267 A1 | 10/2020 | Hoyt et al. |
| 2020/0340000 A1 | 10/2020 | Roy-Chaudhuri et al. |
| 2020/0352195 A1 | 11/2020 | Bansal-Mutalik et al. |
| 2021/0030014 A1 | 2/2021 | Brown et al. |
| 2021/0037851 A1 | 2/2021 | Fraser et al. |
| 2021/0037870 A1* | 2/2021 | Krieger .................. A23J 3/227 |
| 2021/0051976 A1 | 2/2021 | Fraser et al. |
| 2021/0051977 A1 | 2/2021 | Vrljic et al. |
| 2021/0070842 A1 | 3/2021 | Fraser et al. |
| 2021/0106032 A1 | 4/2021 | Leung et al. |
| 2021/0139843 A1 | 5/2021 | Nahmias |
| 2021/0171912 A1 | 6/2021 | Genovese et al. |
| 2021/0235733 A1 | 8/2021 | Kayser et al. |
| 2021/0251251 A1 | 8/2021 | Holz-Schietinger et al. |
| 2021/0289824 A1 | 9/2021 | Brown et al. |
| 2021/0307358 A1 | 10/2021 | Henderson, Jr. et al. |
| 2021/0345654 A1 | 11/2021 | Krieger et al. |
| 2021/0395690 A1 | 12/2021 | Nahmias et al. |
| 2022/0007695 A1 | 1/2022 | Kayser et al. |
| 2022/0183317 A1 | 6/2022 | Krieger et al. |

FOREIGN PATENT DOCUMENTS

| | | |
|---|---|---|
| JP | H104975 A | 1/1998 |
| JP | 2010200627 A | 9/2010 |
| KR | 101151203 B1 | 5/2012 |
| WO | WO-2015161099 A1 | 10/2015 |
| WO | WO-2017124100 A1 | 7/2017 |
| WO | WO-2018022016 A1 | 2/2018 |
| WO | WO-2018189738 A1 | 10/2018 |
| WO | WO-2018227016 A1 | 12/2018 |
| WO | WO-2020074858 A1 | 4/2020 |
| WO | WO-2020095305 A1 | 5/2020 |
| WO | WO-2020100143 A1 | 5/2020 |
| WO | WO-2020123876 A1 | 6/2020 |
| WO | WO-2020149791 A1 | 7/2020 |
| WO | WO-2020160187 A2 | 8/2020 |
| WO | WO-2020222239 A1 | 11/2020 |
| WO | WO-2020230138 A1 | 11/2020 |
| WO | WO-2020237021 A1 | 11/2020 |
| WO | WO-2021148955 A1 | 7/2021 |
| WO | WO-2021148960 A1 | 7/2021 |
| WO | WO-2021158103 A1 | 8/2021 |
| WO | WO-2021250407 A1 | 12/2021 |
| WO | WO-2022047263 A1 | 3/2022 |

OTHER PUBLICATIONS

[Author Unknown] "License Agreement Has Been Entered into with Meatable BV" Nov. 26, 2020 https://ips-cell.net/e/topics/whatsnew/20201126.html, 3 pages.

[Author Unknown] "MeaTech Announces Filing of Provisional Patent Application for Novel Bioprinting Method". News by MeaTech 3D Ltd. (Jun. 3, 2021); https://www.prnewswire.com/news-releases/meatech-announces-filing-of-provisional-patent-application-for-novel-bioprinting-method-301304916.html, 5 pages.

[Author Unknown] "Motif FoodWorks Announces New Partnerships to Improve Taste and Experience in Plant-based Foods". Newswire by Motif FoodWorks, Aug. 3, 2021, https://www.prnewswire.com/news-releases/motif-foodworks-announces-new-partnerships-to-improve-taste-and-experience-in-plant-based-foods-301346987.html, printed Dec. 6, 2021, 4 pages.

[Author Unknown] "Motif FoodWorks Announces Research Collaboration With Renowned Scientist to Develop "Unprecedented" Improvements in Plant-based Foods". Vegconomist—the vegan business magazine—, Jun. 2, 2020, https://vegconomist.com/companies-and-portraits/motif-foodworks-announces-research-collaboration-with-renowned-%E2%80%8B%E2%80%8Bscientist-to-develop-unprecedented-improvements-in-plant-based-foods/, printed Dec. 6, 2021, 7 pages.

[Author Unknown] "Motif FoodWorks Gains Exclusive Access to Transformative Plant-Based Technologies. Motif to expand work with Professor Alejandro Marangoni and the University of Guelph Ontario to create plant-based cheese that stretches and melts, and plant-based meat with healthier, marbleized fat". Newswire by Motif FoodWorks, May 13, 2021, https://www.prnewswire.com/news-releases/motif-foodworks-gains-exclusive-access-to-transformative-plant-based-technologies-301290898.html, printed Dec. 6, 2021, 5 pages.

Allan et al., "Bioprocess Design Considerations for Cultured Meat Production With a Focus on the Expansion Bioreactor". Front. Sustain. Food Syst., Jun. 12, 2019, vol. 3, Article 44, pp. 1-9.

Bhat, et al., "Technological, regulatory, and ethical aspects of in vitro meat: A future slaughter-free harvest". Comprehensive Reviews in Food Science and Food Safety. (Jul. 2019); 18(4): 1192-1208.

Blumenthal, Sam, "'Culture' Shock". https://medium.com/aurelius/culture-shock-fc464b9f6ac6, Aug. 18, 2020, 23 pages.

Bonnet, et al., "Ontogenesis of muscle and adipose tissues and their interactions in ruminants and other species". Animal (Jul. 2010); 4(7): 1093-1109. Epub Apr. 21, 2010.

Choi, et al., "Muscle stem cell isolation and in vitro culture for meat production: A methodological review". Compr Rev Food Sci Food Saf., Jan. 2021, 20(1): 429-457. Epub Nov. 6, 2020.

Christov, et al., "Muscle satellite cells and endothelial cells: close neighbors and privileged partners". Mol Biol Cell. Apr. 2007; 18(4): 1397-1409. Epub Feb. 7, 2007.

Coles, et al., "Proliferation Rates of Bovine Primary Muscle Cells Relate to Liveweight and Carcase Weight in Cattle". PLoS One. Apr. 15, 2015; 10(4): e0124468.

Ding et al., "Maintaining bovine satellite cells stemness through p38 pathway". Sci Rep. Jul. 17, 2018; 8(1): 10808.

Dmitrieva, et al., "Skeletal Muscle Resident Progenitor Cells Coexpress Mesenchymal and Myogenic Markers and Are Not Affected by Chronic Heart Failure-Induced Dysregulations". Stem Cells Int. Jan. 3, 2019; 2019: 5690345, 12 pages.

Fernyhough, et al., "Primary adipocyte culture: adipocyte purification methods may lead to a new understanding of adipose tissue growth and development". Cytotechnology (Oct. 2004); 46(2): 163-172.

Fish, et al., "Prospects and challenges for cell-cultured fat as a novel food ingredient". Trends in Food Science & Technology (Apr. 1, 2020); 98: 53-67.

Foye-Edwards, R., "The 'Steaks' Are High: In Vitro Meat Moves From The Petri Dish To The Palate". Article (online), Journal of Young Investigators, Nov. 1, 2014, pp. 1-5, URL: https://www.jyi.org/2014-november/2017/3/23/the-steaks-are-high-in-vitro-meat-moves-from-the-petri-dish-to-the-palate.

Fraeye, et al., "Sensorial and nutritional aspects of cultured meat in comparison to traditional meat: much to be inferred". Frontiers in Nutrition (Mar. 24, 2020); 7: 35, p. 1-7.

Fronticelli., et al., 2005, Geneseq Accession No. ADZ80046, computer printout, pp. 1-3.

Fu, et al., "Reduced satellite cell density and myogenesis in Wagyu compared with Angus cattle as a possible explanation of its high marbling". Animal. May 2018; 12(5): 990-997. Epub Oct. 9, 2017.

(56) References Cited

OTHER PUBLICATIONS

Genovese., et al., 2021, US20210171912A1, effective filing date, Oct. 30, 2013.
Gerlach, et al., "Adipogenesis of human adipose-derived stem cells within three-dimensional hollow fiber-based bioreactors". Tissue Engineering Part C: Methods. (Jan. 1, 2012); 18(1): 54-61.
Gonzalez, et al., "Satellite cells and their regulation in livestock". Journal of Animal Science, May 2020, vol. 98, Issue 5, skaa081, pp. 1-13.
Green and Meuth, "An established pre-adipose cell line and its differentiation in culture". Cell (Oct. 1, 1974); 3(2): 127-133.
Hausman, et al., "Board-invited review: the biology and regulation of preadipocytes and adipocytes in meat animals". Journal of Animal Science (Apr. 1, 2009); 87(4): 1218-1246.
Hernandez, B., et al., "Comparison Between Two Different Methods to Obtain the Proportions of Myoglobin Redox Forms on Fresh Meat from Reflectance Measurements". Journal of Food Science Technology, 2015, vol. 52, pp. 8212-8219.
Hsieh, et al., "Development of a synthetic meat flavor mixture by using surface response methodology". Journal of Food Science (Sep. 1980); 45(5): 1125-1130.
Hunt, et al., "AMSA meat color measurement guidelines", American Meat Science Association, Champaign, Illinois USA, Updated Dec. 21, 2012, 136 pages.
International Preliminary Report on Patentability for International Application No. PCT/US2020/033945, dated Nov. 16, 2021, 15 pages.
International Search Report and Written Opinion for International Application No. PCT/US2020/033945, dated Oct. 26, 2020, 20 pages.
International Search Report and Written Opinion for International Application No. PCT/US2022/078365 dated Jan. 17, 2023, 14 pages.
Jung, et al., "Large-scale production of human mesenchymal stem cells for clinical applications". Biotechnology and Applied Biochemistry (Mar. 2012); 59(2): 106-120.
Kadim, et al., "Cultured meat from muscle stem cells: A review of challenges and prospects". Journal of Integrative Agriculture (Feb. 1, 2015); 14(2): 222-233.
Kanatous and Mammen, "Regulation of myoglobin expression". J Exp Biol. (Aug. 15, 2010); 213(Pt 16): 2741-2747.
Katzen et al., 2013, US 20130274129 A1.
Ladeira, et al., "Nutrigenomics and beef quality: A review about lipogenesis". International Journal of Molecular Sciences (Jun. 2016); 17(6): 918.
Lim, Juyun, "Hedonic scaling: A review of methods and theory." Food Quality and Preference, Dec. 2011, vol. 22, Issue 8, pp. 133-141.
Liu, et al., "Oleate induces transdifferentiation of chicken fibroblasts into adipocyte-like cells". Comparative Biochemistry and Physiology Part A: Molecular & Integrative Physiology (Sep. 1, 2009); 154(1): 135-141.
Mercola, Joseph, Dr., "Controversy Over Fake Meat Burger Heats Up as Documents Reveal FDA Safety Concerns". Organic Consumers Association News, Aug. 21, 2017, https://www.organicconsumers.org/news/controversy-over-fake-meat-burger-heats-documents-reveal-fda-safety-concerns, 2 pages.
Moritz et al., "Alternatives for large-scale production of cultured beef: A review". Journal of Integrative Agriculture, Feb. 2015, vol. 14, Issue 2, pp. 208-216.
Nobusue, et al., "Establishment of a preadipocyte cell line derived from mature adipocytes of GFP transgenic mice and formation of adipose tissue". Cell Tissue Research (Jun. 2008); 332(3): 435-446.
Pawlowski, et al., "Inducible and Deterministic Forward Programming of Human Pluripotent Stem Cells into Neurons, Skeletal Myocytes, and Oligodendrocytes". Stem Cell Reports (Apr. 11, 2017); 8(4): 803-812.
Post, M., "Cultured Meat From Stem Cells: Challenges And Prospects", Meat Science, Nov. 2012, 92(3): 297-301.
Roesner, A., et al., "Hypoxia Induces a Complex Response of Globin Expression in Zebrafish (*Danio rerio*)". The Journal of Experimental Biology, Jun. 2006, vol. 209 (Pt 11), pp. 2129-2137.
Schweihofer, J., "The Color of Meat Depends on Myoglobin: Part 1", Article (online), Michigan State University Extension, Oct. 10, 2014, 3 pages, URL: https://www.canr.msu.edu/news/the_color_of_meat_depends_on_myoglobin_part_1, (Oct. 8, 2020).
Shang, et al., "Oleate promotes differentiation of chicken primary preadipocytes in vitro". Bioscience Reports (Feb. 7, 2014); 34(1): e00093, pp. 51-57.
Warris, P.D., "The extraction of haem pigments from fresh meat". Food Science + Technology (Feb. 1979); 14(1): 75-80.
Wei, et al., "Bovine dedifferentiated adipose tissue (DFAT) cells: DFAT cell isolation". Adipocyte (Jul. 24, 2013); 2(3): 148-159.
Yan, Z., "Regulatory Elements Governing Transcription in Specialized Myofiber Subtypes". The Journal of Biological Chemistry, May 18, 2001, vol. 276, No. 20, pp. 17361-17366. Epub Feb. 26, 2001.
Yin, et al., "In vitro myogenic and adipogenic differentiation model of genetically engineered bovine embryonic fibroblast cell lines". Biotechnology Letters (Feb. 2010); 32(2): 195-202.
Yin, et al., "Satellite cells and the muscle stem cell niche". Physiol Rev. Jan. 2013; 93(1): 23-67.
Yu, et al., "Studies on meat color, myoglobin content, enzyme activities, and genes associated with oxidative potential of pigs slaughtered at different growth stages". Asian-Australas J Anim Sci. (Dec. 2017); 30(12): 1739-1750. Epub May 14, 2017.
Zhang et al., "Challenges and possibilities for bio-manufacturing cultured meat". Trends in Food Science & Technology, Mar. 2020, vol. 97, pp. 443-450.

* cited by examiner

Beef Control Patty
5% (w/w) animal meat
5% (w/w) animal fat
No Myoglobin
With Flavoring Agent
5% (w/w) animal meat
5% (w/w) animal fat
1.55% Myoglobin
With Flavoring Agent
Plant-based
Control Patty
With Flavoring Agent
Fig. 8B  Raw  Cooked

PLANT BASE/ANIMAL CELL HYBRID MEAT SUBSTITUTE

CROSS-REFERENCE TO RELATED APPLICATIONS

This application is a continuation application of International Application No. PCT/US2022/078365, filed Oct. 19, 2022, which claims the benefit of U.S. Provisional Application No. 63/257,418, filed Oct. 19, 2021, and U.S. Provisional Application No. 63/283,144, filed Nov. 24, 2021, the content of each of which is herein incorporated by reference in its entirety.

REFERENCE TO AN ELECTRONIC SEQUENCE LISTING

The contents of the electronic sequence listing (ARFO_020_01WO_SeqList_ST26.xml; Size: 33,972 bytes; and Date of Creation: Oct. 19, 2022) is herein incorporated by reference in its entirety.

BACKGROUND

Animal meat is one of the most versatile protein-rich food products available, and a common staple in Western diets. However, the practice of intensive animal agriculture poses an increasingly significant environmental problem due to its heavy use of water and land resources, as well as its high greenhouse gas emissions.

On the other hand, current meat substitute products, such as plant-based meat substitutes, cannot offer tastes similar to animal meat, and therefore have not been widely accepted by consumers.

There is a need in the art for meat substitute products that closely mimic the characteristics and tastes of animal meat. The present disclosure provides such meat substitute products, process for making such products, and more.

SUMMARY

In one aspect, the present disclosure provides a hybrid meat substitute product comprising:
 a) a plant-based meat dough;
 b) animal cells; and
 c) exogenous heme-containing protein.

In some embodiments, the hybrid meat substitute product comprises at least 0.75% heme-containing protein by weight, and at least 2.5% animal cells by weight, wherein the animal cells are cultured animal cells.

In some embodiments, the hybrid meat substitute product comprises: d) animal fat.

In some embodiments, the hybrid meat substitute product does not comprise methylcellulose or its derivative.

In some embodiments, the animal cells comprise, or are derived from, skeletal muscle cells, myoblasts, myogenic cells, fibroblasts, mesenchymal stem cells, endothelial cells, adipose progenitor cells, preadipocytes, or cardiomyocytes. In some embodiments, the animal cells are not hepatocytes. In some embodiments, the animal cells are myoblasts. In some embodiments, the animal cells are substantially undifferentiated cultivated myoblast cells. In some embodiments, at least 90%, 80%, 70%, 60% of the animal cells do not exhibit muscle fibers or myotubes.

In some embodiments, the animal cells are cultivated cells. In some embodiments, the animal cells are suspension culture cells (i.e., wherein more than 90%, 80%, 70%, or 60% of the animal cells not adhered to any growth substrate). In some embodiments, the animal cells are not in a meat structure. In some embodiments, the animal cells do not comprise any connective tissue and/or a blood vessel.

In some embodiments, the hybrid meat substitute product comprises between 0.1-40% animal cells by weight. In some embodiments, the hybrid meat substitute product comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, or 39%, animal cells by weight, including all ranges and subranges in between. In some embodiments, the hybrid meat substitute product comprises at least 2.5% animal cells by weight, including all ranges and subranges in between. In some embodiments, the hybrid meat substitute product comprises no more than 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, or 39%, animal cells by weight, including all ranges and subranges in between. In some embodiments, the hybrid meat substitute product comprises between 2-10% animal cells by weight. In some embodiments, the hybrid meat substitute product comprises no more than 20% animal cells by weight.

In some embodiments, the hybrid meat substitute product comprises between 0.1-10% exogenous heme-containing protein by weight. In some embodiments, the hybrid meat substitute product comprises at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% exogenous heme-containing protein by weight, including all ranges and subranges in between. In some embodiments, the hybrid meat substitute product comprises at least 0.25% exogenous heme-containing protein by weight. In some embodiments, the hybrid meat substitute product comprises no more than 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% exogenous heme-containing protein by weight, including all ranges and subranges in between.

In some embodiments, the hybrid meat substitute product comprises between 0.5-2.5% exogenous heme-containing protein by weight. In some embodiments, the hybrid meat substitute product comprises between 0.5-2% exogenous heme-containing protein by weight. In some embodiments, the hybrid meat substitute product comprises between 0.5-1% exogenous heme-containing protein by weight. In some embodiments, the hybrid meat substitute product comprises at least 0.5% exogenous heme-containing protein by weight. In some embodiments, the hybrid meat substitute product comprises animal cells and exogenous heme-containing protein at an amount according to one of the combinations listed in Table 1A.

In some embodiments, the hybrid meat substitute product comprises between 0.1-10% total heme-containing protein by weight. In some embodiments, the hybrid meat substitute product comprises at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% total heme-containing protein by weight, including all ranges and subranges in between. In some embodiments, the hybrid meat substitute product comprises at least 0.25% total heme-containing protein by weight. In some embodiments, the hybrid meat substitute product comprises no more than 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% total heme-containing protein by weight, including all ranges and subranges in between.

In some embodiments, the hybrid meat substitute product comprises between 0.6-2.6% total heme-containing protein by weight. In some embodiments, the hybrid meat substitute product comprises between 0.6-1.6% total heme-containing protein by weight. In some embodiments, the hybrid meat substitute product comprises between 0.5-1.0% total heme-containing protein by weight. In some embodiments, the hybrid meat substitute product comprises at least 0.6% total heme-containing protein by weight. In some embodiments, the hybrid meat substitute product comprise animal cells and total heme-containing protein at an amount according to one of the combinations listed in Table 1B.

In some embodiments, the exogenous heme-containing protein is selected from the group consisting of a non-symbiotic hemoglobin, a Hell's gate globin I, a flavohemoprotein, a leghemoglobin, a heme-dependent peroxidase, a cytochrome c peroxidase, a mammalian myoglobin, an androglobin, a cytoglobin, a globin E, a globin X, a globin Y, a hemoglobin, a myoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin, a truncated 2/2 globin, a hemoglobin 3, a cytochrome, and a peroxidase. In some embodiments, the exogenous heme-containing protein is a myoglobin. In some embodiments, at least 30%, 40%, 50%, 60%, 70%, 80%, or 90% of the myoglobin is oxymyoglobin. In some embodiments, at least 30%, 40%, 50%, 60%, 70%, 80%, or 90% of the myoglobin is deoxymyoglobin. In some embodiments, at least 30%, 40%, 50%, 60%, 70%, 80%, or 90% of the myoglobin is metmyoglobin. In some embodiments, the heme-containing protein is bovine myoglobin, wherein the bovine myoglobin comprises an amino acid sequence having at least 80%, 85%, 90%, or 95% identity to SEQ ID NO: 1.

In some embodiments, the hybrid meat substitute product comprises between 0.0003-0.03% by weight of iron (Fe) bound to the (exogenous or total) heme-containing protein. In some embodiments, the hybrid meat substitute product comprises at least 0.0003%, 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, or 0.026%, by weight of iron (Fe) bound to the (exogenous or total) heme-containing protein. In some embodiments, the hybrid meat substitute product comprises at least 0.00075% by weight of iron (Fe) bound to the (exogenous or total) heme-containing protein. In some embodiments, the hybrid meat substitute product comprises at least 0.0015% by weight of iron (Fe) bound to the (exogenous or total) heme-containing protein. In some embodiments, the hybrid meat substitute product comprises no more than 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, 0.026%, or 0.03% by weight of iron (Fe) bound to the (exogenous or total) heme-containing protein. In some embodiments, the hybrid meat substitute product comprises between 0.0015-0.006% by weight of iron (Fe) bound to the (exogenous or total) heme-containing protein.

In some embodiments, the animal fat is from cultivated cells. In some embodiments, the animal fat is from cultivated adipocytes.

In some embodiments, the hybrid meat substitute product comprises between 0.1-30% animal fat by weight. In some embodiments, the hybrid meat substitute product comprises between 5-30% animal fat by weight. In some embodiments, the hybrid meat substitute product comprises between 10-20% total fat by weight. In some embodiments, the hybrid meat substitute product comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, animal fat by weight, including all ranges and subranges in between. In some embodiments, the hybrid meat substitute product comprises at least 2.5% animal fat by weight. In some embodiments, the hybrid meat substitute product comprises no more than 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, animal fat by weight, including all ranges and subranges in between. In some embodiments, the hybrid meat substitute product comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, total fat by weight, including all ranges and subranges in between. In some embodiments, the hybrid meat substitute product comprises no more than 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, total fat by weight, including all ranges and subranges in between. In some embodiments, the hybrid meat substitute product comprises animal fat and exogenous heme-containing protein at an amount according to one of the combinations listed in Table 2A. In some embodiments, the hybrid meat substitute product comprises animal fat and total heme-containing protein at an amount according to one of the combinations listed in Table 2B.

In some embodiments, at least a portion of the exogenous heme-containing protein is comprised within the animal cells. In some embodiments, less than 10%, 20%, 30%, 40%, 50%, or 60% of the (relative) exogenous heme-containing protein in the hybrid meat substitute product is comprised within the animal cells.

In some embodiments, the exogenous heme-containing protein is provided as an cell-free or substantially cell-free ingredient.

In some embodiments, the animal cells are bovine cells, porcine cells, ovine cells, chicken cells, turkey cells, or cells from an aquatic animal species.

In some embodiments, the animal fat is from a bovine, porcine, or ovine source.

In some embodiments, the hybrid meat substitute product does not comprise any binding agent selected from methylcellulose, hydroxypropylmethyl cellulose, guar gum, locust bean gum, xanthan gum, agar, pectin, carrageenan, konjac, alginate, agarose, starch (native or modified), flours, and derivatives thereof. In some embodiments, the hybrid meat substitute product does not comprise any binding agent.

In one aspect, the present disclosure provides hybrid meat substitute products comprising:
a) 60%-97% plant-based meat dough by weight;
b) 1%-10% cultivated animal cells by weight;
c) 1%-10% exogenous heme-containing protein by weight;
d) 1%-25% animal fat by weight;
wherein the animal cells have not differentiated into muscle fibers and wherein the cultivated animal cells are from a cow.

In one aspect, the present disclosure provides hybrid meat substitute products comprising:
a) 60%-97% plant-based meat dough by weight;
b) 1%-10% cultivated animal cells by weight;
c) 1%-10% total heme-containing protein by weight;
d) 1%-25% animal fat by weight;
wherein the animal cells have not differentiated into muscle fibers and wherein the cultivated animal cells are from a cow.

In some embodiments, at least 20%, at least 30%, at least 40%, at least 50%, at least 60%, at least 70%, at least 80%, at least 90%, at least 95%, at least 98%, at least 99%, or 100%, of the animal cells are myoblasts. In some embodiments, at least 70% of the animal cells are myoblast.

In some embodiments, at least 20%, at least 30%, at least 40%, at least 50%, at least 60%, at least 70%, at least 80%, at least 90%, at least 95%, at least 98%, at least 99%, or 100%, of the animal cells are fibroblasts. In some embodiments, at least 70% of the animal cells are fibroblast.

In some embodiments, the animal cells are not adhered to any growth substrate. In some embodiments, the animal cells are not hepatocytes.

In some embodiments, the hybrid meat substitute product mimics ground meat. In some embodiments, the hybrid meat substitute product is shaped like a burger patty. In some embodiments, the hybrid meat substitute product does not have any methylcellulose.

In one aspect, the present disclosure provides consumer food items selected from the group consisting of: a burger, a meatball, a chili, a shepherd's pie, pizza, taco lasagna, sloppy joe, stroganoff, and meatloaf, wherein said consumer food comprises the hybrid substitute meat product of the disclosure or a cooked product thereof.

In one aspect, the present disclosure provides cooked food products prepared by cooking a food item comprising the hybrid substitute meat product of the disclosure.

In one aspect, the present disclosure provides methods of producing the hybrid substitute meat products of the disclosure, comprising mixing the animal cells with plant-based ingredient(s). In some embodiments, the method further comprises mixing the exogenous heme-containing protein with the animal cells and the plant-based ingredient(s), wherein the exogenous heme-containing protein is provided as an isolated ingredient. In some embodiments, the method further comprises mixing the animal fat with the animal cells and the plant-based ingredient(s).

BRIEF DESCRIPTION OF DRAWINGS

FIG. 1A is a chart showing the scores of visual appeal factors for meat substitute products comprising 0.25%-0.75% (w/w) exogenous myoglobin. FIG. 1B is a chart showing the scores of olfactory appeal factors for meat substitute products comprising 0.25%-0.75% (w/w) exogenous myoglobin. FIG. 1C is a chart showing the scores of flavor appeal factors for meat substitute products comprising 0.25%-0.75% (w/w) exogenous myoglobin.

FIG. 2A is a chart showing the scores of visual appeal factors for meat substitute products comprising 1.00%-1.70% (w/w) exogenous myoglobin. FIG. 2B is a chart showing the scores of olfactory appeal factors for meat substitute products comprising 1.00%-1.70% (w/w) exogenous myoglobin. FIG. 2C is a chart showing the scores of flavor appeal factors for meat substitute products comprising 1.00%-1.70% (w/w) exogenous myoglobin.

FIG. 3A is a chart showing the scores of visual appeal factors for meat substitute products comprising 5% (w/w) animal meat, 5% (w/w) animal fat, and with/without 1.55% (w/w) exogenous myoglobin. FIG. 3B is a chart showing the scores of olfactory appeal factors for meat substitute products comprising 5% (w/w) animal meat, 5% (w/w) animal fat, and with/without 1.55% (w/w) exogenous myoglobin. FIG. 3C is a chart showing the scores of flavor appeal factors for meat substitute products comprising 5% (w/w) animal meat, 5% (w/w) animal fat, and with/without 1.55% (w/w) exogenous myoglobin.

FIG. 4A is a chart showing the scores of visual appeal factors for meat substitute products comprising 5% (w/w) animal meat, 5% (w/w) animal fat, with/without 1.55% (w/w) exogenous myoglobin, and with a flavoring blend. FIG. 4B is a chart showing the scores of olfactory appeal factors for meat substitute products comprising 5% (w/w) animal meat, 5% (w/w) animal fat, with/without 1.55% (w/w) exogenous myoglobin, and with a flavoring blend. FIG. 4C is a chart showing the scores of flavor appeal factors for meat substitute products comprising 5% (w/w) animal meat, 5% (w/w) animal fat, with/without 1.55% (w/w) exogenous myoglobin, and with a flavoring blend.

FIG. 6A is a chart showing the scores of visual appeal factors for meat substitute products comprising 2.5% (w/w) animal meat and/or 0.5%-0.75% (w/w) exogenous myoglobin. FIG. 6B is a chart showing the scores of olfactory appeal factors for meat substitute products comprising 2.5% (w/w) animal meat and/or 0.5%-0.75% (w/w) exogenous myoglobin. FIG. 6C is a chart showing the scores of flavor appeal factors for meat substitute products comprising 2.5% (w/w) animal meat and/or 0.5%-0.75% (w/w) exogenous myoglobin.

FIG. 8A-B depict pictures of meat substitute products according to the present disclosure. FIG. 8A shows photos of burger patties (raw and cooked) made of meat substitute products comprising 5% (w/w) animal meat, 5% (w/w) animal fat, and with/without 1.55% (w/w) exogenous myoglobin, together with corresponding plant matrix base or 100% beef patty controls. FIG. 8B shows photos of burger patties (raw and cooked) made of meat substitute products comprising 5% (w/w) animal meat, 5% (w/w) animal fat, with/without 1.55% (w/w) exogenous myoglobin, and a flavoring blend, together with corresponding plant matrix base or 100% beef patty controls.

FIG. 9A shows a photo of a semi-cooked trial burger patty without methylcellulose binder. FIG. 9B shows a photo of a fully cooked trial burger patty without methylcellulose binder.

DETAILED DESCRIPTION

Figure 1A:
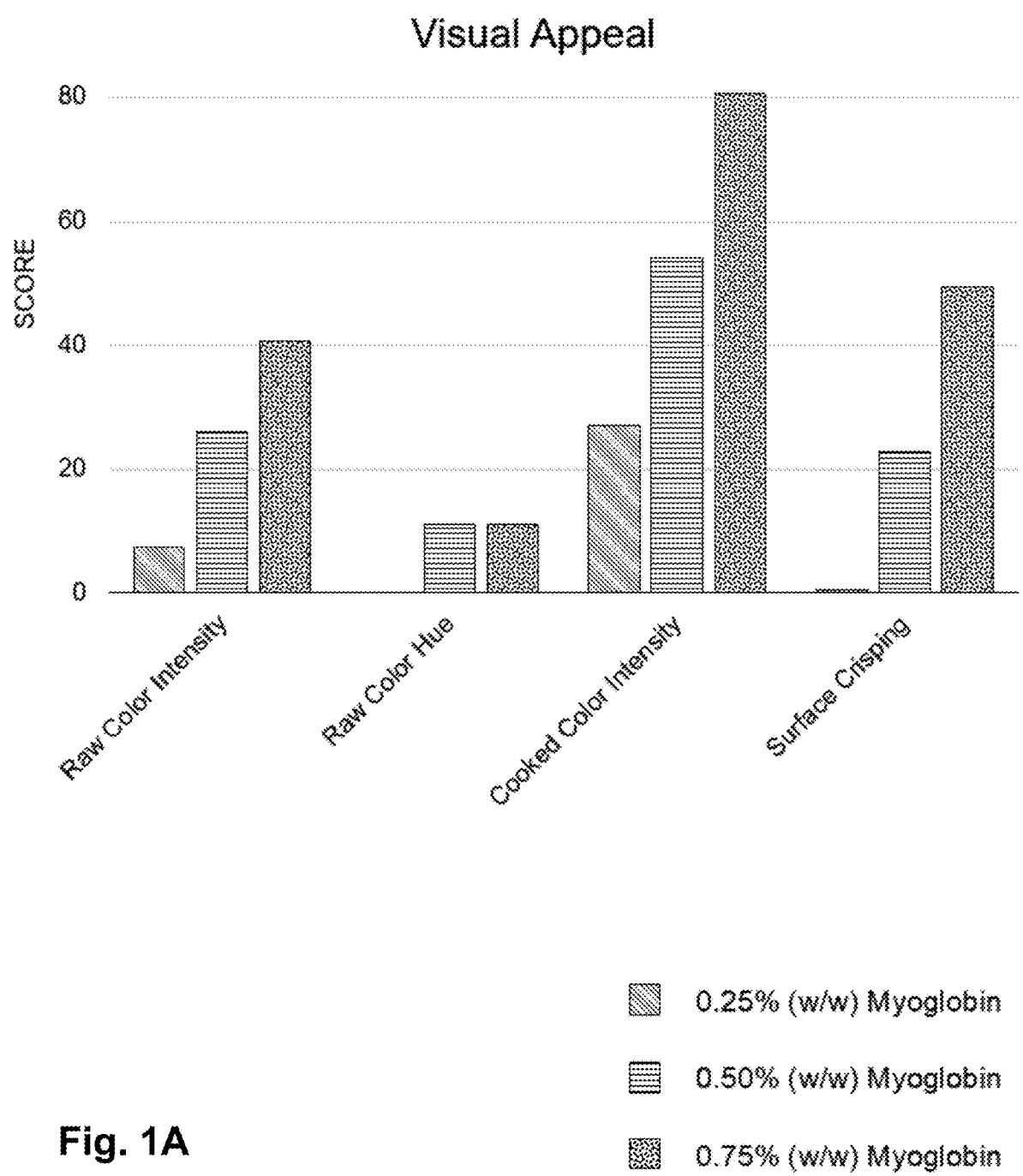
FIG. 1A-C shows the results of a consumer preference test of meat substitute products.

The details of the disclosure are set forth in the accompanying description below. Although methods and materials similar or equivalent to those described herein can be used in the practice or testing of the present disclosure, illustrative methods, and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Embodiments according to the present disclosure will be described more fully hereinafter. Aspects of the disclosure may, however, be embodied in different forms and should not be construed as limited to the embodiments set forth herein. Rather, these embodiments are provided so that this disclosure will be thorough and complete, and will fully convey the scope of the invention to those skilled in the art. Unless explicitly indicated otherwise, all specified some embodiments, features, and terms intend to include both the recited embodiment, feature, or term and biological equivalents thereof. The terminology used in the description herein is for the purpose of describing particular embodiments only and is not intended to be limiting.

Definitions

As used in this specification and the appended claims, the singular forms "a," "an" and "the" include plural references unless the content clearly dictates otherwise.

As used in this specification and the appended claims, the term "and/or" is used in this disclosure to either "and" or "or" unless indicated otherwise.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

Ranges in this document should be understood to be inclusive of their end points. A content range of 1-5% w/w of an ingredient, for example, includes contents of 1.0% w/w and 5.0% w/w. Sections of this document will reference various possible values and will then recite that this list of values also includes all ranges and subranges therebetween. This should be interpreted as also disclosing the total range of values listed in the text as well as any subrange from any one number to another number listed in the relevant text. For example, a recitation of 1%, 2%, 3%, 4%, 5%, or 6% content of a particular ingredient, including all "ranges and subranges" therebetween, would also encompass the range of values of 1% to 6%, and/or subranges, such as 3% to 4%.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The term "animal meat" as used herein refers to flesh derived from skeletal muscle or from other organs (e.g., kidney, heart, liver, gallbladder, intestine, stomach, bone marrow, brain, thymus, lung, tongue), or parts thereof, derived from an animal. The animal meat can be dark or white meat. Suitable animals from which the animal meat can be derived include but are not limited to cattle, lamb, mutton, horse, poultry (e.g., chicken, duck, goose, turkey), fowl (any bird species, pigeon, dove, grouse, partridge, ostrich, emu, pheasant, quail), fresh or saltwater fish (e.g., catfish, tuna, spearfish, shark, halibut, sturgeon, salmon, bass, muskie, pike, bowfin, gar, eel, paddlefish, bream, carp, trout, walleye, snakehead, crap-pie, sister, mussel, scallop, abalone, squid, octopus, sea urchin, cuttlefish, tunicate), crustacean (e.g., crab, lobster, shrimp, barnacle), game animals (e.g., deer, fox, wild pig, elk, moose, reindeer, caribou, antelope, zebra, squirrel, marmot, rabbit, bear, beaver, muskrat, opossum, raccoon, armadillo, porcupine, bison, buffalo, boar, lynx, bobcat, bat), reptiles (e.g., snakes, turtles, lizards, alligators, crocodiles), any insect or other arthropod, rodent (nutria, guinea pig, rat, mice, vole, groundhog, capybara), kangaroo, whale, and seal. The term refers to ground, chopped, shredded, or otherwise processed animal meat. The term encompasses both uncooked, cooking, and cooked animal meat unless otherwise indicated herein or clearly contradicted by context. The meat may be intact, in chunks, in steak form, ground, finely textured, trim or residues derived from processing frozen animals, low temperature rendered, mechanically separated or deboned (MDM, which is a meat paste that is recovered from animal bones, and a comminuted product that is devoid of the natural fibrous texture found in intact muscles) (i.e., meat removed from bone by various mechanical means), cooked, or combinations thereof. The meat may include muscle, skin, fat (including rendered fat such as lard and tallow, flavor enhanced animal fats, fractionated or further processed animal fat tissue), or other animal components.

The term "binding agent" as used herein refers to an agent that promotes, supports, or enables holding together ingredients in one cohesive mass.

The term "dough" or "plant-based meat dough" as used herein refers to a blend of dry ingredients ("dry mix"; e.g., proteins, carbohydrates, and lipids including solid and liquid fats and oils) and liquid ingredients ("liquid mix"; e.g., water, flavoring or juice [i.e., liquid based extract from a non-animal source such as a plant or any part of a plant]) from which a meat substitute product is produced through the application of mechanical energy (e.g., spinning, agitating, shaking, shearing, pressure, turbulence, impingement, confluence, beating, friction, wave), radiation energy (e.g., microwave, electromagnetic), thermal energy (e.g., heating, steam texturizing), enzymatic activity (e.g., crosslinking activity), chemical reagents (e.g., pH and/or ionic strength adjusting agents, kosmotropic salts, chaotropic salts, gypsum, surfactants, emulsifiers, fatty acids, amino acids), other methods that lead to protein denaturation and protein fiber alignment, or combinations of these methods, followed by fixation of the fibrous structure (e.g., by rapid temperature and/or pressure change, rapid dehydration, chemical fixation, redox). In some embodiments, the present disclosure teaches plant-based meat dough, which refers to plant-based meat substitute products. References to plant-based meat dough contents in a hybrid meat substitute product does not include animal cells, animal fat, or exogenous heme protein (even if from a plant source), as these are accounted for separately.

The term "meat-like" as used herein refers to resemblance (visual, olfactory, and/or flavor) to animal meat.

The term "hybrid meat substitute product" as used herein refers to a food product that comprises a plant-based meat dough, and no more than 60% (w/w) of animal cells. In some embodiments, the hybrid meat substitute product further comprises exogenous heme-containing protein (e.g., exogenous myoglobin). In some embodiments, the hybrid meat substitute product has structure, texture, taste, flavor and/or other properties comparable to those of animal meat. In some embodiments, the animal cells are muscle (e.g., myoblast) cells. In some embodiments, the hybrid meat substitute product further comprises animal fat. In some embodiments, the animal fat is provided in the form of adipocyte cells. Adipocyte cells are not considered "animal cells" for the purpose of this disclosure. The term "hybrid meat substitute product" refers to uncooked, cooking, and cooked hybrid meat substitute product unless otherwise indicated herein or clearly contradicted by context.

The term "exogenous heme-containing protein" as used herein refers to a heme-containing protein that is artificially added to the plant-based meat dough. In some embodiments, the exogenous heme-containing protein is provided as an isolated ingredient. In some embodiments, the exogenous heme-containing protein is expressed as a recombinant protein in non-animal cells such as those from a yeast, fungi, algae, or plant. In some embodiments, the exogenous heme-containing protein is provided as part of another ingredient in the hybrid meat substitute product (e.g., in a complex extract or within cells that artificially express the heme-containing product). When provided within a cell, the exogenous heme-containing protein is 1) expressed in the cell from an exogenous gene (i.e., the protein does not exist in the wild type cells); and/or 2) is expressed at super physiological levels due to one or more genetic modification(s) to the cells (e.g., by adding extra copies of a gene encoding a heme-containing protein, or genetically engineering the gene loci encoding the native heme-containing protein for overexpression). Animal cells expressing myoglobin are disclosed in US 2021/0037870, which is hereby incorporated in its entirety for all purposes. In some embodiments the animal cells of the present disclosure contain unmodified levels of heme-containing protein, and the vast majority of the heme-containing protein is provided from other sources.

The term "super physiological," as used herein, refers to expression/accumulation higher than an appropriate control. For example, when used in the context of cells comprising genetic modifications to increase expression of heme-containing protein, the term "super physiological" refers to the cell's accumulation of heme-containing protein at levels higher than the normal expression level of that heme-containing protein in the wild type cells under the same conditions (e.g., in culture).

The terms "cultured meat", "cultured cells" "cell-based meat", "cultivated cells" and "cultivated meat" generally refer to meat/cells that contain animal cells grown outside the animal, for example in bioreactor systems or other similar production or cell culture systems.

The terms "genetically modified cell line" or "cell line comprising a genetic modification" refer to a cell line that has been genetically altered, modified, or engineered, such that it exhibits an altered, modified, or different genotype and/or phenotype (e.g., when the genetic modification affects coding nucleic acid sequences of the cell), as compared to the cell from which it was derived. It is understood that in some embodiments, the terms refer not only to the particular cell line in question, but also to the progeny or potential progeny of such a cell line.

The terms "genetically modified", "genetically engineered" or "genetic modification" may refer to any manipulation of a host cell's genome (e.g., by insertion, deletion, mutation, or replacement of nucleic acids). Genetically modified cells include cells harboring artificially added extra recombinant DNA, such as plasmids.

The term "immortalization" generally refers to increasing the Hayflick limit of a cell. "Hayflick limit" generally refers to the finite number of divisions a cell can undergo before the cell becomes senescent. Each time a cell undergoes mitosis, the telomeres on the ends of each chromosome may shorten. Generally cell division ceases once telomeres shorten to a critical length. In some cases, an immortalized cell may undergo a finite number of mitoses. In some cases, an immortalized cell may undergo mitosis indefinitely.

The term "differentiation" generally refers to a change from a relatively generalized type of cell to a more specialized kind of cell. In some cases, this may comprise an event where either a mononuclear myogenic cell (skeletal muscle cell) fuses with more myogenic cells into a multinucleated muscle fiber capable of generating increased contractile force, or the transition of a fibroblast, mesenchymal stem cell, or an adipose progenitor cell to a mature adipocyte that contains intracellular fat droplets. Myogenic cells can be induced to differentiate when they reach a sufficiently high density. The differentiation of myogenic cells is called "myogenesis", and the differentiation of fat progenitor cells is called "adipogenesis". In some embodiments, the animal cells of the present disclosure do not form or accumulate muscle fibers.

As used herein the term "sequence identity" refers to the extent to which two optimally aligned polynucleotides or polypeptide sequences are invariant throughout a window of alignment of residues, e.g. nucleotides or amino acids. An "identity fraction" for aligned segments of a test sequence and a reference sequence is the number of identical residues which are shared by the two aligned sequences divided by the total number of residues in the reference sequence segment, i.e. the entire reference sequence or a smaller defined part of the reference sequence. "Percent identity" or % (percent) "sequence identity" is the identity fraction times 100. Comparison of sequences to determine percent identity can be accomplished by a number of well-known methods, including for example by using mathematical algorithms, such as, for example, those in the BLAST suite of sequence analysis programs. Unless noted otherwise, the term "sequence identity" in the claims refers to sequence identity as calculated by BLAST version 2.11.0 using default parameters at the effective filing date of this application.

The term "suspension culture" or "suspension cell culture" or "suspension cell(s)" refers to cell culture in which the majority or all of cells in a culture vessel are present in suspension e.g., are not attached to any substratum or surface, the vessel surface, or to another surface within the vessel. The suspension culture may be shaken, rocked, agitated, rolled or stirred to maintain the cells in suspension. In some embodiments, suspension cultures may contain a small amount of aggregated cells (e.g. small clusters of less than 5 cells), which still count as not being attached to a surface.

The term "derived from" when used in reference to a cell refers to a target cell that is obtained from, changed from, or produced by one or more parent cells (e.g., from a cell line or biological tissue). The parent cell(s) may be a different cell type, which may undergo differentiation, trans-differentiation, or reprogramming to produce the target cell. Alternatively, the parent cell(s) may be the same cell type. In some embodiments, the parent cell(s) undergo one or more physical, chemical, and/or biological treatments (e.g., cell sorting, suspension culturing, mutagenesis, genetic engineering, incubation with growth factors/cytokines/small molecule chemicals) to produce the target cell.

The term "plant-based" as used herein should be interpreted broadly to comprise ingredients not sourced from animals. In some embodiments, the "plant-based" meat dough of the present disclosure, might also include ingredients from yeast, fungi, algae, etc.

Hybrid Meat Substitute Products

The present disclosure relates to hybrid meat substitute products and methods of producing the same. In one aspect, the present disclosure provides hybrid meat substitute products comprising a) a plant-based meat dough; b) animal cells; and c) exogenous heme-containing protein. In some embodiments, the hybrid meat substitute product further comprises d) animal fat.

Meat substitute products, such as plant-based meat substitutes, can help decrease the consumption of animal meat and address the increasingly significant environmental problem caused by intensive animal agriculture. However, a primary hurdle in the meat substitute products industry is that such products do not mimic the characteristics and tastes of animal meat. As a result, consumer acceptance is still relatively low for the current meat substitute products.

For example, US 2021/0051976 discloses meat substitute products with leghemoglobin to produce a popular vegetarian burger. These products combine heme-containing proteins with one or more plant-sourced flavor precursor molecules in an attempt to mimic the visual and flavor appeal of beef burgers. These products, however, lack animal cells, and therefore are unable to fully replicate the consumer experience or nutritional profile of beef burgers.

In contrast, the present disclosure provides hybrid meat substitute products that combine animal cells with exogenous heme-containing products to more closely mimic the characteristics and tastes of animal meat. Without being bound by any particular theory, it is contemplated that exogenous heme-containing protein (e.g., myoglobin) combines with compounds contained within the animal cells during cooking to amplify the consumer likability of meat substitute products. In some embodiments, the hybrid meat substitute products are mostly composed of plant-based ingredients (e.g., the plant-based meat dough), and contain only fractional amounts of animal cells, thereby reducing the overall use of animal products. In some embodiments, the presently disclosed invention is based on the discovery that only small amounts of animal cells are required in combination with exogenous heme-containing proteins, to mimic the flavor of full beef burgers. In other words, the present invention is based, in part, on Applicant's unexpected finding that the addition of animal cells to plant-based meat doughs comprising exogenous heme-containing proteins can further improve upon the flavor of existing vegetarian option (e.g., US 2021/0051976) and can eliminate or reduce the consumer preference (e.g., visual, olfactory, and flavor) differences between a meat substitute product containing at least a portion of animal cells, and traditional meat products comprising 95%+ meat.

In some embodiments, the hybrid meat substitute product of the present disclosure does not include any ingredients harvested from animals, and therefore does not require the killing of animals. In some embodiments, the animal cells of the present disclosure are cultivated cells.

Persons having skill in the art will recognize that traditional hybrid meat substitute products comprising only fractional amounts of animal cells (e.g., 10% animal cells in 90% plant-based meat dough) will only contain small amounts of heme-containing protein. Thus, the present disclosure teaches that hybrid meat products with only animal cells and plant-based meat dough are not sufficient to mimic the experience of a full beef burger.

The low heme-containing protein content problems of traditional hybrid meat products are further complicated when using cultivated cells. Cultivated cells have been reported to produce significantly lower levels of heme-containing proteins than their harvested meat counterparts. Moreover, cultivated cells that are not fully differentiated into muscle or organ tissue (e.g., have not developed muscle fibers) have near zero contents of heme-containing proteins. In some embodiments, the hybrid meat substitute products of the present disclosure are not fully differentiated, and have low levels of endogenous (naturally produced within the cell) heme-containing protein.

Each of the features of the presently disclosed hybrid meat substitute product are discussed in more detail below.

Hybrid Meat Substitute Product Evaluation

The products of the present disclosure were developed and based upon consumer trials. In some embodiments, the hybrid meat substitute products of the present disclosure were evaluated using a "degree of difference" rating scale. (see Lim, Juyun. "Hedonic scaling: A review of methods and theory." *Food Quality and Preference* Volume 22, Issue 8 (2011): 733-747, which is incorporated by reference herein in its entirety). For example, a 9-point "degree of difference" scale can be a balanced bipolar scale around neutral at the center with four positive and four negative categories on each side. In some embodiments, the categories are labeled with phrases representing various degrees of affect and those labels are arranged successively to suggest a single continuum of likes and dislikes, such as:

9. Like Extremely
8. Like Very Much
7. Like Somewhat
6. Like Slightly
5. Neither Like nor Dislike
4. Dislike Slightly
3. Dislike Somewhat
2. Dislike Very Much
1. Dislike Extremely In some embodiments, a "degree of difference" rating scale uses two controls: a positive control of animal meat product, and a negative control of plant-based meat substitute product. In some embodiments, a 7-point "degree of difference" scale based on such controls can be a single continuum of likeness compared to either the positive control or the negative control. In some embodiments, the scale may be:

7. Match to the Positive Control
6. Moderately Closer to the Positive Control
5. Slightly Closer to the Positive Control 4. Close to Neither Controls
3. Slightly Closer to the Negative Control
2. Moderately Closer to the Negative Control
1. Match to the Negative Control A person skilled in the art will readily recognize proper controls for such experiments. In some embodiments, the positive control product is the corresponding animal meat product, and the negative control product is the plant-based meat substitute product identical to the hybrid meat substitute product except for the one or more distinguishing features (e.g., exogenous heme-containing protein).

Such "degree of difference" rating scale can be used to measure various features of the food product. Non-limiting examples of such features include 1) visual appeals such as raw color intensity, raw color hue, cooked color intensity, cooked color hue, and surface crisping, 2) olfactory appeals such as meaty/beefiness aroma and mineral/iron aroma, 3) flavor appeals such as meaty/beefiness flavor, mineral/iron flavor, and balance/sweetness, and 4) overall consumer liking.

For each feature of the food product, scores from multiple tasters based on such "degree of difference" rating scale can be converted to an average score by 1) converting the points of scale to evenly distributed values on a 0-100 scale—for example, for a 9-point scale, the $1^{st}$ point has a score of 0, the $2^{nd}$ point has a score of 12.5, the $3^{rd}$ point has a score of 25, and so on; and 2) averaging the scores from each taster.

Exogenous Heme-Containing Protein

In some embodiments, the hybrid meat substitute products of the present disclosure are fortified with one or more exogenous heme-containing proteins. As mentioned above, the present inventors discovered, that traditional slaughter free hybrid meat substitute products suffered from low heme-containing protein content because 1) the products only contained a small portion of animal cells (e.g., less than 20% or 30%), and ii) because the animal cells, were cultivated, and therefore had low heme containing protein content. In some embodiments, even differentiated cultured cells failed to achieve sufficiently high heme protein contents to produce hybrid products with sufficient resemblance to traditional slaughter meat products. In some embodiments, the hybrid meat substitute products of the present disclosure contain exogenous heme-containing protein. In some embodiments, the exogenous heme-containing protein comprises heme protein provided in addition to any heme-proteins in the animal cells.

"Heme-containing proteins," "hemeproteins" and "hemoproteins," are proteins that possess a heme group, which contains an iron ion coordinated to a porphyrin (a group of heterocyclic rings, which can reversibly bind to a molecule of oxygen gas). The heme group confers functionality, which can include oxygen carrying, oxygen reduction, electron transfer, and other processes. Hemeproteins can be hemoglobins, found in the blood of animal species, or myoglobins, found within cardiac or skeletal muscle cells. Hemeproteins vary in their gene and protein structure, giving them different oxygen affinities and oxygen dissociation constants.

In some embodiments, the exogenous heme-containing protein is a protein selected from the group consisting of a non-symbiotic hemoglobin, a Hell's gate globin I, a flavo-hemoprotein, a leghemoglobin, a heme-dependent peroxidase, a cytochrome c peroxidase, a mammalian myoglobin, an androglobin, a cytoglobin, a globin E, a globin X, a globin Y, a hemoglobin, a myoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin, a truncated 2/2 globin, a hemoglobin 3, a cytochrome, and a peroxidase. In some embodiments, the exogenous heme-containing protein is a bovine myoglobin. In some embodiments, the exogenous heme-containing protein is a myoglobin from *Bos taurus*.

In some embodiments, the exogenous heme-containing protein comprises an amino acid sequence having at least 60%, at least 65%, at least 70%, at least 75%, at least 80%, at least 85%, at least 90%, at least 95%, at least 96%, at least 97%, at least 98%, at least 99%, at least 99.5%, or 100% identity to a mammalian myoglobin protein such as the *Bos taurus* myoglobin (SEQ ID NO: 1), *Sus scrofa* myoglobin (SEQ ID NO: 19), or *Equus caballus* myoglobin (SEQ ID NO: 20), a hemoglobin from *Vigna radiata* (SEQ ID NO: 18). *Hordeum vulgare* (SEQ ID NO: 5), *Zea mays* (SEQ ID NO: 13). *Oryza saliva* subsp *japonica* (rice) (SEQ ID NO: 14), or *Arabidopsis thaliana* (SEQ ID NO: 15), a Hell's gate globin I such as that from *Methylacidiphilum infernorum* (SEQ ID NO: 2), a flavohemoprotein such as that from *Aquifex aeolicus* (SEQ ID NO: 3), a leghemoglobin such as that from *Glycine max* (SEQ ID NO: 4), *Pisum sativum* (SEQ ID NO: 16), or *Vigna unguiculata* (SEQ ID NO: 17), a heme-dependent peroxidase such as from *Magnaporthe oryzae* (SEQ ID NO: 6), or *Fusarium oxysporum* (SEQ ID NO: 7), a cytochrome c peroxidase from *Fusarium graminearum* (SEQ ID NO: 8), a truncated hemoglobin from *Chlamydomonas moewusii* (SEQ ID NO: 9), *Tetrahymena pyriformis* (SEQ ID NO: 10, group I truncated), *Paramecium caudatum* (SEQ ID NO: 11, group I truncated), a hemoglobin from *Aspergillus niger* (SEQ ID NO: 12), a *Synechocystis* PCC6803 truncated hemoglobin (SEQ ID NO: 21), a *Synechococcus* sp. PCC 7335 truncated hemoglobin (SEQ ID NO: 22), a *Nostoc commune* hemoglobin (SEQ ID NO: 23), a *Vitreoscilla stercoraria* hemoglobin (SEQ ID NO: 24), a *Corynebacterium glutamicum* hemoglobin (SEQ ID NO: 25), a *Bacillus subtilis* truncated hemoglobin (SEQ ID NO: 26), a *Bacillus megaterium* truncated hemoglobin (SEQ ID NO: 27), a *Saccharomyces cerevisiae* flavohemoglobin (SEQ ID NO: 28), a *Nicotina tobaccum* hemoglobin (SEQ ID NO: 29), a *Medicago sativa* hemoglobin (SEQ ID NO: 30), or a *Glycine max* hemoglobin (SEQ ID NO: 31).

In some embodiments, the heme-containing protein is myoglobin. Myoglobin is a ~17 kDa hemeprotein. It possesses a single heme group, where hemoglobin contains four heme groups. It is naturally expressed in animal skeletal muscle cells in type I, type II A, and type II B muscle. Myoglobin reversibly binds to oxygen and serves as an oxygen storage system. The heme group in myoglobin provides a red pigment to meat, depending on the oxidation state of the iron ion. In fresh meat, the iron ion is bound to oxygen and in the +2 oxidation state, making oxymyoglobin, and giving the meat a red color. Metmyoglobin is the oxidized form of the oxygen-carrying hemeprotein myoglobin, with the iron at +3 oxidation. Metmyoglobin is the cause of the characteristic brown coloration of meat that occurs as it ages. In some embodiments, the heme containing protein is red. In some embodiments, the heme containing protein is oxymyoglobin. In some embodiments, the heme containing protein is metmyoglobin. In some embodiments, the heme-containing protein is a mixture of oxymyoglobin and metmyoglobin. Unless stated otherwise, or obvious from the context, references to "myoglobin" or "heme protein"/"heme containing protein" more generally, include all oxidation states of the protein.

In some embodiments, the exogenous heme-containing protein is a myoglobin from *Bos taurus*. In some embodiments, the myoglobin comprises an amino acid sequence having at least 80%, at least 85%, at least 90%, at least 95%, at least 96%, at least 97%, at least 98%, at least 99%, at least 99.5%, or 100% identity to SEQ ID NO: 1. In some embodiments, the myoglobin comprises an amino acid sequence having at least 95% identity to SEQ ID NO: 1.

An exemplary bovine myoglobin has the amino acid sequence of:

(SEQ ID NO: 1)
MGLSDGEWQLVLNAWGKVEADVAGHGQEVLIRLFTGHPETLEKFDKFKHL

KTEAEMKASEDLKKHGNTVLTALGGILKKKGHHEAEVKHLAESHANKHKI

PVKYLEFISDAIIHVLHAKHPSDFGADAQAAMSKALELFRNDMAAQYKVL

GFHG

In some embodiments, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the myoglobin is oxymyoglobin. In some embodiments, at least 70% of the myoglobin is oxymyoglobin.

In some embodiments, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the myoglobin is deoxymyoglobin. In some embodiments, at least 70% of the myoglobin is deoxymyoglobin.

In some embodiments, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or 100% of the myoglobin is metmyoglobin. In some embodiments, at least 70% of the myoglobin is metmyoglobin.

In some embodiments, the exogenous heme-containing protein comprises or consists of recombinantly expressed protein. In some embodiments, the exogenous heme-containing protein is recombinantly expressed in a host cell. In some embodiments, the host cells are bacteria, yeast, insect or mammalian cells. In some embodiments, the heme-containing proteins are purified after recombinant expression. In some embodiments, the recombinantly expressed exogenous heme-containing protein are comprised within stock solutions having a concentration/purity of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% by weight. A 100 gram stock solution of 90% w/w heme-containing protein, could comprise, for example, 90 grams of heme-containing protein and 10 grams of water/buffer. Regardless of the purity/concentration of the stock solution used to deliver the heme-containing protein, measurements regarding the heme-protein content of any products within this disclosure are based on the weight of the protein itself, and not any impurities/solvents.

In some embodiments, the exogenous heme-containing protein is provided as a cell-free ingredient, as a stock solution, not contained within cells. In some embodiments, the exogenous heme-containing protein is a substantially cell-free ingredient, wherein at least 70%, 80%, 90%, or 95% or more of the exogenous heme-containing protein is not encompassed within a cell.

In some embodiments, the exogenous heme-containing protein comprises or consists of proteins extracted from a plant, fungi or animal. In some embodiments, the exogenous heme-containing protein is extracted from a plant. In some embodiments, the plant is selected from the group consisting of soybean, sprouted soybean, alfalfa, golden flax, black bean, black eyed pea, northern, garbanzo, mung bean, cowpeas, pinto beans, pod peas, quinoa, sesame, sunflower, wheat berries, spelt, barley, wild rice, or rice. In some embodiments, the extracted exogenous heme-containing protein is comprised within a stock solution having a purity of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% by weight.

In some embodiments, at least a portion of the exogenous heme-containing protein is comprised within the animal cells of the disclosure. For example, in some embodiments, animal cells included in the hybrid meat substitute product are modified to exhibit super physiological levels of heme-containing protein. In some embodiments the animal cells with wild type levels (or super physiological levels) of heme-containing protein are further supplemented with additional exogenous heme-containing protein within products of the present disclosure. In some embodiments, the Total Heme-Containing Protein Levels (such as those present within a hybrid meat substitute product) comprises the wild type level of protein included in the animal cells, and any exogenous heme-containing protein added to the hybrid meat substitute product, including super physiological levels of heme within the animal cells.

In some embodiments, cells providing exogenous heme-containing protein accumulate "super physiological" levels of that protein. Thus, in some embodiments, animal cells delivering "exogenous heme-containing proteins" comprise both a basal amount of heme-containing protein (i.e. amount of protein that would be present in wild type cells), and an enhanced amount of heme-containing protein that represents the portion of accumulated protein that is over and above that of an appropriate control cell (e.g., from a genetic modification). The term "exogenous heme-containing protein" as used herein with reference to animal cells comprises only the super physiological levels of heme-containing protein within the cell. The term "Total Heme-Containing Protein" with reference to the cell, comprises the total content of heme-containing protein within the cell, which includes the basal amount and any enhanced amount achieved through (e.g., genetic modifications).

In some embodiments, the animal cells of the present disclosure comprise at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% Total Heme-Containing Protein by weight of the cells, including all ranges and subranges in between. In some embodiments, the animal cells comprise between 0.1-0.5%, 0.5-1%, 1-2%, 2-3%, 3-4%, 4-5%, 5-6%, 6-7%, 7-8%, 8-9%, 9-10%, 10-12%, 12-15%, 15-20%, 20-25%, 25-30%, 30-35%, or 35-40%, Total Heme-Containing Protein by weight of the cells, including all ranges and subranges in between. In some embodiments, the animal cells comprise between 0.1-1%, 0.5-2%, 1-3%, 2-4%, 3-5%, 4-6%, 5-7%, 6-8%, 7-9%, 8-10%, 9-12%, 10-15%, 12-20%, 15-25%, 20-30%, 25-35%, or 30-40%, Total Heme-Containing Protein by weight of the cells, including all ranges and subranges in between. In some embodiments, the animal cells comprise between 0.1-2%, 0.5-3%, 1-4%, 2-5%, 3-6%, 4-7%, 5-8%, 6-9%, 7-10%, 8-12%, 9-15%, 10-20%, 12-25%, 15-30%, 20-35%, or 25-40%, Total Heme-Containing Protein by weight of the cells, including all ranges and subranges in between. In some embodiments the heme-containing protein weight of animal cells is calculated based on dry weight. In some embodiments heme-containing protein weight of animal cells is calculated based on culture weight, of cells immediately after they are separated from their culture medium (e.g., after media separation from their suspension culture).

In some embodiments, the animal cells of the present disclosure comprise at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% exogenous heme-containing protein by weight of the cells, including all ranges and subranges in between. In some embodiments, the animal cells comprise between 0.1-0.5%, 0.5-1%, 1-2%, 2-3%, 3-4%, 4-5%, 5-6%, 6-7%, 7-8%, 8-9%, 9-10%, 10-12%, 12-15%, 15-20%, 20-25%, 25-30%, 30-35%, or 35-40%, exogenous heme-containing protein by weight of the cells, including all ranges and subranges in between. In some embodiments, the animal cells comprise between 0.1-1%, 0.5-2%, 1-3%, 2-4%, 3-5%, 4-6%, 5-7%, 6-8%, 7-9%, 8-10%, 9-12%, 10-15%, 12-20%, 15-25%, 20-30%, 25-35%, or 30-40%, exogenous heme-containing protein by weight of the cells, including all ranges and subranges in between. In some embodiments, the animal cells comprise between 0.1-2%, 0.5-3%, 1-4%, 2-5%, 3-6%, 4-7%, 5-8%, 6-9%, 7-10%, 8-12%, 9-15%, 10-20%, 12-25%, 15-30%, 20-35%, or 25-40%, exogenous heme-containing protein by weight of the cells, including all ranges and subranges in between. In some embodiments the heme-containing protein weight of animal cells is calculated based on dry weight. In some embodiments heme-containing protein weight of animal cells is calculated based on culture weight, of cells immediately after they are separated from their culture medium (e.g., after media separation from their suspension culture).

In some embodiments, the hybrid meat substitute product comprises between 0.1-10% exogenous heme-containing protein by weight of the product.

In some embodiments, the hybrid meat substitute product comprises about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, 9.5%, or 10%, exogenous heme-containing protein by weight, including all ranges and subranges therebetween.

In some embodiments, the hybrid meat substitute product comprises at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5%, exogenous heme-containing protein by weight, including all ranges and subranges in between. In some embodiments, the hybrid meat substitute product comprises at least 0.25% exogenous heme-containing protein by weight.

In some embodiments, the hybrid meat substitute product comprises no more than 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, 9.5%, or 10%, exogenous heme-containing protein by weight, including all ranges and subranges in between.

In some embodiments, the hybrid meat substitute product comprises between 0.1-0.2%, 0.2-0.3%, 0.3-0.4%, 0.4-0.5%, 0.5-0.6%, 0.6-0.7%, 0.7-0.8%, 0.8-0.9%, 0.9-1%, 1-1.1%, 1.1-1.2%, 1.2-1.3%, 1.3-1.4%, 1.4-1.5%, 1.5-1.6%, 1.6-1.7%, 1.7-1.8%, 1.8-1.9%, 1.9-2%, 2-2.2%, 2.2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, or 9.5-10%, exogenous heme-containing protein by weight, including all ranges and subranges in between.

In some embodiments, the hybrid meat substitute product comprises between 0.1-0.3%, 0.2-0.4%, 0.3-0.5%, 0.4-0.6%, 0.5-0.7%, 0.6-0.8%, 0.7-0.9%, 0.8-1%, 0.9-1.1%, 1-1.2%, 1.1-1.3%, 1.2-1.4%, 1.3-1.5%, 1.4-1.6%, 1.5-1.7%, 1.6-1.8%, 1.7-1.9%, 1.8-2%, 1.9-2.2%, 2-2.5%, 2.2-3%, 2.5-3.5%, 3-4%, 3.5-4.5%, 4-5%, 4.5-5.5%, 5-6%, 5.5-6.5%, 6-7%, 6.5-7.5%, 7-8%, 7.5-8.5%, 8-9%, 8.5-9.5%, or 9-10%, exogenous heme-containing protein by weight, including all ranges and subranges in between.

In some embodiments, the hybrid meat substitute product comprises between 0.1-0.4%, 0.2-0.5%, 0.3-0.6%, 0.4-0.7%, 0.5-0.8%, 0.6-0.9%, 0.7-1%, 0.8-1.1%, 0.9-1.2%, 1-1.3%, 1.1-1.4%, 1.2-1.5%, 1.3-1.6%, 1.4-1.7%, 1.5-1.8%, 1.6-1.9%, 1.7-2%, 1.8-2.2%, 1.9-2.5%, 2-3%, 2.2-3.5%, 2.5-4%, 3-4.5%, 3.5-5%, 4-5.5%, 4.5-6%, 5-6.5%, 5.5-7%, 6-7.5%, 6.5-8%, 7-8.5%, 7.5-9%, 8-9.5%, or 8.5-10%, exogenous heme-containing protein by weight, including all ranges and subranges in between.

In some embodiments, the hybrid meat substitute product comprises between 0.1-0.6%, 0.2-0.7%, 0.3-0.8%, 0.4-0.9%, 0.5-1%, 0.6-1.1%, 0.7-1.2%, 0.8-1.3%, 0.9-1.4%, 1-1.5%, 1.1-1.6%, 1.2-1.7%, 1.3-1.8%, 1.4-1.9%, 1.5-2%, 1.6-2.2%, 1.7-2.5%, 1.8-3%, 1.9-3.5%, 2-4%, 2.2-4.5%, 2.5-5%, 3-5.5%, 3.5-6%, 4-6.5%, 4.5-7%, 5-7.5%, 5.5-8%, 6-8.5%, 6.5-9%, 7-9.5%, or 7.5-10%, exogenous heme-containing protein by weight, including all ranges and subranges in between.

In some embodiments, the hybrid meat substitute product comprises between 0.1-0.9%, 0.2-1%, 0.3-1.1%, 0.4-1.2%, 0.5-1.3%, 0.6-1.4%, 0.7-1.5%, 0.8-1.6%, 0.9-1.7%, 1-1.8%, 1.1-1.9%, 1.2-2%, 1.3-2.2%, 1.4-2.5%, 1.5-3%, 1.6-3.5%, 1.7-4%, 1.8-4.5%, 1.9-5%, 2-5.5%, 2.2-6%, 2.5-6.5%, 3-7%, 3.5-7.5%, 4-8%, 4.5-8.5%, 5-9%, 5.5-9.5%, or 6-10%, exogenous heme-containing protein by weight, including all ranges and subranges in between.

In some embodiments, the hybrid meat substitute product comprises between 0.5-2% exogenous heme-containing protein by weight.

In some embodiments, the hybrid meat substitute product comprises between 0.5-1.5% exogenous heme-containing protein by weight.

In some embodiments, the hybrid meat substitute product comprises between 1-2% exogenous heme-containing protein by weight.

In some embodiments, the hybrid meat substitute product comprises between 0.1-10% Total Heme-Containing Protein by weight of the product.

In some embodiments, the hybrid meat substitute product comprises about 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, 9.5%, or 10%, Total Heme-Containing Protein by weight, including all ranges and subranges therebetween.

In some embodiments, the hybrid meat substitute product comprises at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5%, Total Heme-Containing Protein by weight, including all ranges and subranges in between. In some embodiments, the hybrid meat substitute product comprises at least 0.25% Total Heme-Containing Protein by weight.

In some embodiments, the hybrid meat substitute product comprises no more than 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, 9.5%, or 10%, Total Heme-Containing Protein by weight, including all ranges and subranges in between.

In some embodiments, the hybrid meat substitute product comprises between 0.1-0.2%, 0.2-0.3%, 0.3-0.4%, 0.4-0.5%, 0.5-0.6%, 0.6-0.7%, 0.7-0.8%, 0.8-0.9%, 0.9-1%, 1-1.1%, 1.1-1.2%, 1.2-1.3%, 1.3-1.4%, 1.4-1.5%, 1.5-1.6%, 1.6-1.7%, 1.7-1.8%, 1.8-1.9%, 1.9-2%, 2-2.2%, 2.2-2.5%, 2.5-3%, 3-3.5%, 3.5-4%, 4-4.5%, 4.5-5%, 5-5.5%, 5.5-6%, 6-6.5%, 6.5-7%, 7-7.5%, 7.5-8%, 8-8.5%, 8.5-9%, 9-9.5%, or 9.5-10%, Total Heme-Containing Protein by weight, including all ranges and subranges in between.

In some embodiments, the hybrid meat substitute product comprises between 0.1-0.3%, 0.2-0.4%, 0.3-0.5%, 0.4-0.6%, 0.5-0.7%, 0.6-0.8%, 0.7-0.9%, 0.8-1%, 0.9-1.1%, 1-1.2%, 1.1-1.3%, 1.2-1.4%, 1.3-1.5%, 1.4-1.6%, 1.5-1.7%, 1.6-1.8%, 1.7-1.9%, 1.8-2%, 1.9-2.2%, 2-2.5%, 2.2-3%, 2.5-3.5%, 3-4%, 3.5-4.5%, 4-5%, 4.5-5.5%, 5-6%, 5.5-6.5%, 6-7%, 6.5-7.5%, 7-8%, 7.5-8.5%, 8-9%, 8.5-9.5%, or 9-10%, Total Heme-Containing Protein by weight, including all ranges and subranges in between.

In some embodiments, the hybrid meat substitute product comprises between 0.1-0.4%, 0.2-0.5%, 0.3-0.6%, 0.4-0.7%, 0.5-0.8%, 0.6-0.9%, 0.7-1%, 0.8-1.1%, 0.9-1.2%, 1-1.3%, 1.1-1.4%, 1.2-1.5%, 1.3-1.6%, 1.4-1.7%, 1.5-1.8%, 1.6-1.9%, 1.7-2%, 1.8-2.2%, 1.9-2.5%, 2-3%, 2.2-3.5%, 2.5-4%, 3-4.5%, 3.5-5%, 4-5.5%, 4.5-6%, 5-6.5%, 5.5-7%, 6-7.5%, 6.5-8%, 7-8.5%, 7.5-9%, 8-9.5%, or 8.5-10%, Total Heme-Containing Protein by weight, including all ranges and subranges in between.

In some embodiments, the hybrid meat substitute product comprises between 0.1-0.6%, 0.2-0.7%, 0.3-0.8%, 0.4-0.9%, 0.5-1%, 0.6-1.1%, 0.7-1.2%, 0.8-1.3%, 0.9-1.4%, 1-1.5%, 1.1-1.6%, 1.2-1.7%, 1.3-1.8%, 1.4-1.9%, 1.5-2%, 1.6-2.2%, 1.7-2.5%, 1.8-3%, 1.9-3.5%, 2-4%, 2.2-4.5%, 2.5-5%, 3-5.5%, 3.5-6%, 4-6.5%, 4.5-7%, 5-7.5%, 5.5-8%, 6-8.5%, 6.5-9%, 7-9.5%, or 7.5-10%, Total Heme-Containing Protein by weight, including all ranges and subranges in between.

In some embodiments, the hybrid meat substitute product comprises between 0.1-0.9%, 0.2-1%, 0.3-1.1%, 0.4-1.2%, 0.5-1.3%, 0.6-1.4%, 0.7-1.5%, 0.8-1.6%, 0.9-1.7%, 1-1.8%, 1.1-1.9%, 1.2-2%, 1.3-2.2%, 1.4-2.5%, 1.5-3%, 1.6-3.5%, 1.7-4%, 1.8-4.5%, 1.9-5%, 2-5.5%, 2.2-6%, 2.5-6.5%, 3-7%, 3.5-7.5%, 4-8%, 4.5-8.5%, 5-9%, 5.5-9.5%, or 6-10%, Total Heme-Containing Protein by weight, including all ranges and subranges in between.

In some embodiments, the hybrid meat substitute product comprises between 0.5-2% Total Heme-Containing Protein by weight.

In some embodiments, the hybrid meat substitute product comprises between 0.5-1.5% Total Heme-Containing Protein by weight.

In some embodiments, the hybrid meat substitute product comprises between 1-2% Total Heme-Containing Protein by weight.

In some embodiments, one gram of the heme-containing protein comprises between 0.0003-0.03 gram of bound iron (Fe). In some embodiments, one gram of the heme-containing protein comprises between 0.001-0.01 gram of bound iron (Fe). In some embodiments, one gram of the heme-containing protein comprises about 0.003 gram of bound iron (Fe). (For example, a mammalian myoglobin has a molecular weight of about 17.8 kDa, and one myoglobin comprises one iron (Fe) atom (molecular weight of 55.84 Da) bound to its heme group.) Accordingly, in some embodiments, the amount of the iron (Fe) bound to the heme-containing protein within the hybrid meat substitute product or the animal cells of the disclosure can be calculated by multiplying the amount of the heme-containing protein by a factor of 0.003.

In some embodiments, the hybrid meat substitute product comprises between 0.0003-0.03% by weight of iron (Fe) bound to the exogenous heme-containing protein.

In some embodiments, the hybrid meat substitute product comprises about 0.0003%, 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, 0.026%, or 0.03% by weight of iron (Fe) bound to the exogenous heme-containing protein, including all ranges and subranges therebetween.

In some embodiments, the hybrid meat substitute product comprises at least 0.0003%, 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, or 0.026%, by weight of iron (Fe) bound to the exogenous heme-containing protein, including all ranges and subranges in between.

In some embodiments, the hybrid meat substitute product comprises no more than 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, 0.026%, or 0.03% by weight of iron (Fe) bound to the exogenous heme-containing protein, including all ranges and subranges in between.

In some embodiments, the hybrid meat substitute product comprises between 0.0003%-0.0004%, 0.0004%-0.0005%, 0.0005%-0.0006%, 0.0006%-0.0007%, 0.0007%-0.0008%, 0.0008%-0.0009%, 0.0009%-0.001%, 0.001%-0.0012%, 0.0012%-0.0014%, 0.0014%-0.0016%, 0.0016%-0.0018%, 0.0018%-0.002%, 0.002%-0.0023%, 0.0023%-0.0026%, 0.0026%-0.003%, 0.003%-0.0035%, 0.0035%-0.004%, 0.004%-0.0045%, 0.0045%-0.005%, 0.005%-0.006%, 0.006%-0.007%, 0.007%-0.008%, 0.008%-0.009%, 0.009%-0.01%, 0.01%-0.012%, 0.012%-0.014%, 0.014%-0.016%, 0.016%-0.018%, 0.018%-0.02%, 0.02%-0.023%, 0.023%-0.026%, or 0.026%-0.03%, by weight of iron (Fe) bound to the exogenous heme-containing protein, including all ranges and subranges in between.

In some embodiments, the hybrid meat substitute product comprises between 0.0003%-0.0005%, 0.0004%-0.0006%, 0.0005%-0.0007%, 0.0006%-0.0008%, 0.0007%-0.0009%, 0.0008%-0.001%, 0.0009%-0.0012%, 0.001%-0.0014%, 0.0012%-0.0016%, 0.0014%-0.0018%, 0.0016%-0.002%, 0.0018%-0.0023%, 0.002%-0.0026%, 0.0023%-0.003%, 0.0026%-0.0035%, 0.003%-0.004%, 0.0035%-0.0045%, 0.004%-0.005%, 0.0045%-0.006%, 0.005%-0.007%, 0.006%-0.008%, 0.007%-0.009%, 0.008%-0.01%, 0.009%-0.012%, 0.01%-0.014%, 0.012%-0.016%, 0.014%-0.018%, 0.016%-0.02%, 0.018%-0.023%, 0.02%-0.026%, or 0.023%-0.03%, by weight of iron (Fe) bound to the exogenous heme-containing protein, including all ranges and subranges in between.

In some embodiments, the hybrid meat substitute product comprises between 0.0003%-0.0006%, 0.0004%-0.0007%, 0.0005%-0.0008%, 0.0006%-0.0009%, 0.0007%-0.001%, 0.0008%-0.0012%, 0.0009%-0.0014%, 0.001%-0.0016%, 0.0012%-0.0018%, 0.0014%-0.002%, 0.0016%-0.0023%, 0.0018%-0.0026%, 0.002%-0.003%, 0.0023%-0.0035%, 0.0026%-0.004%, 0.003%-0.0045%, 0.0035%-0.005%, 0.004%-0.006%, 0.0045%-0.007%, 0.005%-0.008%, 0.006%-0.009%, 0.007%-0.01%, 0.008%-0.012%, 0.009%-0.014%, 0.01%-0.016%, 0.012%-0.018%, 0.014%-0.02%, 0.016%-0.023%, 0.018%-0.026%, or 0.02%-0.03%, by weight of iron (Fe) bound to the exogenous heme-containing protein, including all ranges and subranges in between.

In some embodiments, the hybrid meat substitute product comprises between 0.0003%-0.0007%, 0.0004%-0.0008%, 0.0005%-0.0009%, 0.0006%-0.001%, 0.0007%-0.0012%, 0.0008%-0.0014%, 0.0009%-0.0016%, 0.001%-0.0018%, 0.0012%-0.002%, 0.0014%-0.0023%, 0.0016%-0.0026%, 0.0018%-0.003%, 0.002%-0.0035%, 0.0023%-0.004%, 0.0026%-0.0045%, 0.003%-0.005%, 0.0035%-0.006%, 0.004%-0.007%, 0.0045%-0.008%, 0.005%-0.009%, 0.006%-0.01%, 0.007%-0.012%, 0.008%-0.014%, 0.009%-0.016%, 0.01%-0.018%, 0.012%-0.02%, 0.014%-0.023%, 0.016%-0.026%, or 0.018%-0.03%, by weight of iron (Fe) bound to the exogenous heme-containing protein, including all ranges and subranges in between.

In some embodiments, the hybrid meat substitute product comprises between 0.0003%-0.0008%, 0.0004%-0.0009%, 0.0005%-0.001%, 0.0006%-0.0012%, 0.0007%-0.0014%, 0.0008%-0.0016%, 0.0009%-0.0018%, 0.001%-0.002%, 0.0012%-0.0023%, 0.0014%-0.0026%, 0.0016%-0.003%, 0.0018%-0.0035%, 0.002%-0.004%, 0.0023%-0.0045%, 0.0026%-0.005%, 0.003%-0.006%, 0.0035%-0.007%, 0.004%-0.008%, 0.0045%-0.009%, 0.005%-0.01%, 0.006%-0.012%, 0.007%-0.014%, 0.008%-0.016%, 0.009%-0.018%, 0.01%-0.02%, 0.012%-0.023%, 0.014%-0.026%, or 0.016%-0.03%, by weight of iron (Fe) bound to the exogenous heme-containing protein, including all ranges and subranges in between.

In some embodiments, the hybrid meat substitute product comprises between 0.0015-0.006% by weight of iron (Fe) bound to the exogenous heme-containing protein.

In some embodiments, the hybrid meat substitute product comprises between 0.0015-0.0045% by weight of iron (Fe) bound to the exogenous heme-containing protein.

In some embodiments, the hybrid meat substitute product comprises between 0.003-0.006% by weight of iron (Fe) bound to the exogenous heme-containing protein.

In some embodiments, the hybrid meat substitute product comprises between 0.0003-0.03% by weight of iron (Fe) bound to the total heme-containing protein.

In some embodiments, the hybrid meat substitute product comprises about 0.0003%, 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, 0.026%, or 0.03% by weight of iron (Fe) bound to the total heme-containing protein, including all ranges and subranges therebetween.

In some embodiments, the hybrid meat substitute product comprises at least 0.0003%, 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, or 0.026%, by weight of iron (Fe) bound to the total heme-containing protein, including all ranges and subranges in between.

In some embodiments, the hybrid meat substitute product comprises no more than 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, 0.026%, or 0.03% by weight of iron (Fe) bound to the total heme-containing protein, including all ranges and subranges in between.

In some embodiments, the hybrid meat substitute product comprises between 0.0003%-0.0004%, 0.0004%-0.0005%, 0.0005%-0.0006%, 0.0006%-0.0007%, 0.0007%-0.0008%, 0.0008%-0.0009%, 0.0009%-0.001%, 0.001%-0.0012%, 0.0012%-0.0014%, 0.0014%-0.0016%, 0.0016%-0.0018%, 0.0018%-0.002%, 0.002%-0.0023%, 0.0023%-0.0026%, 0.0026%-0.003%, 0.003%-0.0035%, 0.0035%-0.004%, 0.004%-0.0045%, 0.0045%-0.005%, 0.005%-0.006%, 0.006%-0.007%, 0.007%-0.008%, 0.008%-0.009%, 0.009%-0.01%, 0.01%-0.012%, 0.012%-0.014%, 0.014%-0.016%, 0.016%-0.018%, 0.018%-0.02%, 0.02%-0.023%, 0.023%-0.026%, or 0.026%-0.03%, by weight of iron (Fe) bound to the total heme-containing protein, including all ranges and subranges in between.

In some embodiments, the hybrid meat substitute product comprises between 0.0003%-0.0005%, 0.0004%-0.0006%, 0.0005%-0.0007%, 0.0006%-0.0008%, 0.0007%-0.0009%, 0.0008%-0.001%, 0.0009%-0.0012%, 0.001%-0.0014%, 0.0012%-0.0016%, 0.0014%-0.0018%, 0.0016%-0.002%, 0.0018%-0.0023%, 0.002%-0.0026%, 0.0023%-0.003%, 0.0026%-0.0035%, 0.003%-0.004%, 0.0035%-0.0045%, 0.004%-0.005%, 0.0045%-0.006%, 0.005%-0.007%, 0.006%-0.008%, 0.007%-0.009%, 0.008%-0.01%, 0.009%-0.012%, 0.01%-0.014%, 0.012%-0.016%, 0.014%-0.018%, 0.016%-0.02%, 0.018%-0.023%, 0.02%-0.026%, or 0.023%-0.03%, by weight of iron (Fe) bound to the total heme-containing protein, including all ranges and subranges in between.

In some embodiments, the hybrid meat substitute product comprises between 0.0003%-0.0006%, 0.0004%-0.0007%, 0.0005%-0.0008%, 0.0006%-0.0009%, 0.0007%-0.001%, 0.0008%-0.0012%, 0.0009%-0.0014%, 0.001%-0.0016%, 0.0012%-0.0018%, 0.0014%-0.002%, 0.0016%-0.0023%, 0.0018%-0.0026%, 0.002%-0.003%, 0.0023%-0.0035%, 0.0026%-0.004%, 0.003%-0.0045%, 0.0035%-0.005%, 0.004%-0.006%, 0.0045%-0.007%, 0.005%-0.008%, 0.006%-0.009%, 0.007%-0.01%, 0.008%-0.012%, 0.009%-0.014%, 0.01%-0.016%, 0.012%-0.018%, 0.014%-0.02%, 0.016%-0.023%, 0.018%-0.026%, or 0.02%-0.03%, by weight of iron (Fe) bound to the total heme-containing protein, including all ranges and subranges in between.

In some embodiments, the hybrid meat substitute product comprises between 0.0003%-0.0007%, 0.0004%-0.0008%, 0.0005%-0.0009%, 0.0006%-0.001%, 0.0007%-0.0012%, 0.0008%-0.0014%, 0.0009%-0.0016%, 0.001%-0.0018%, 0.0012%-0.002%, 0.0014%-0.0023%, 0.0016%-0.0026%, 0.0018%-0.003%, 0.002%-0.0035%, 0.0023%-0.004%, 0.0026%-0.0045%, 0.003%-0.005%, 0.0035%-0.006%, 0.004%-0.007%, 0.0045%-0.008%, 0.005%-0.009%, 0.006%-0.01%, 0.007%-0.012%, 0.008%-0.014%, 0.009%-0.016%, 0.01%-0.018%, 0.012%-0.02%, 0.014%-0.023%, 0.016%-0.026%, or 0.018%-0.03%, by weight of iron (Fe) bound to the total heme-containing protein, including all ranges and subranges in between.

In some embodiments, the hybrid meat substitute product comprises between 0.0003%-0.0008%, 0.0004%-0.0009%, 0.0005%-0.001%, 0.0006%-0.0012%, 0.0007%-0.0014%, 0.0008%-0.0016%, 0.0009%-0.0018%, 0.001%-0.002%, 0.0012%-0.0023%, 0.0014%-0.0026%, 0.0016%-0.003%, 0.0018%-0.0035%, 0.002%-0.004%, 0.0023%-0.0045%, 0.0026%-0.005%, 0.003%-0.006%, 0.0035%-0.007%, 0.004%-0.008%, 0.0045%-0.009%, 0.005%-0.01%, 0.006%-0.012%, 0.007%-0.014%, 0.008%-0.016%, 0.009%-0.018%, 0.01%-0.02%, 0.012%-0.023%, 0.014%-0.026%, or 0.016%-0.03%, by weight of iron (Fe) bound to the total heme-containing protein, including all ranges and subranges in between.

In some embodiments, the hybrid meat substitute product comprises between 0.0015-0.006% by weight of iron (Fe) bound to the total heme-containing protein.

In some embodiments, the hybrid meat substitute product comprises between 0.0015-0.0045% by weight of iron (Fe) bound to the total heme-containing protein.

In some embodiments, the hybrid meat substitute product comprises between 0.003-0.006% by weight of iron (Fe) bound to the total heme-containing protein.

Animal Cells

In one aspect, the present disclosure provides hybrid meat substitute product comprising animal cells.

In some embodiments, the animal cells are in a meat structure. In some embodiments, the animal cells are in bovine meat (beef meat), porcine meat, ovine meat, chicken meat, turkey meat, or meat from an aquatic animal species. In some embodiments, the animal cells are in bovine meat (beef meat). In some embodiments, the meat structure comprises a connective tissue and/or a blood vessel. In some embodiments the meat structure is harvested from an animal. In some embodiments the meat structure is produced in culture (is cultivated meat).

In some embodiments, the animal cells are not in a meat structure. In some embodiments, the animal cells are cultivated. In some embodiments, the animal cells are obtained from suspension culture.

In some embodiments, the animal cells comprise, or are derived from the group consisting of skeletal muscle cells, myoblasts, myogenic cells, fibroblasts, mesenchymal stem cells, endothelial cells, cardiomyocytes, bone marrow derived cells, chondrocytes, or other cell types found in organ meat such as heart, kidney, or liver. In some embodiments, the animal cells comprise, or are derived from, skeletal muscle cells, myoblasts, myogenic cells, fibroblasts, mesenchymal stem cells, endothelial cells, or cardiomyocytes. In some embodiments, the animal cells that are derived from a metazoan cell has the same cell type as the metazoan cell.

In some embodiments, the animal cells are myoblasts. In some embodiments, myoblast may be characterized by the expression of genes including PAX7, MYOD, MYF4, MYF5, and/or MYOG. During embryonic muscle development, muscle progenitor cells enter the myogenic lineage by first expressing Myf5, followed by MyoD. Myoblasts expressing MyoD/Myf5 then differentiate and fuse with myoblasts to form multinucleated myotubes. MYOG is expressed in myoblasts to promote differentiation. PAX7 is also a MRF expressed in satellite cells in postnatal skeletal muscle. In addition, mesenchymal stem cell (MSC) markers (CD105, CD73, CD166, CD146, and/or CD140a & b) may be used to characterize skeletal muscle stem cells. Further description of myogenic cells characterization can be found in Dmitrieva et al., Stem Cells Int. 2019 Jan. 3; 2019: 5690345; Fu et al., Animal. 2018 May; 12(5):990-997; Yin et al., Physiol Rev. 2013 January; 93(1):23-67; Arye and Levenberg, Front. Sustain. Food Syst., 18 Jun. 2019 (3) 46; Gonzalez et al., J Anim Sci. 2020 May 1; 98(5):skaa081; Choi et al., Compr Rev Food Sci Food Saf. 2021 January; 20(1):429-457; Coles et al., PLoS One. 2015; 10(4): e0124468; Christov et al., Mol Biol Cell. 2007 April; 18(4):1397-409; Ding et al., Sci Rep. 2018; 8: 10808; each of which is incorporated by reference herein in its entirety.

In some embodiments, the animal cells are not hepatocytes.

In some embodiments, the animal cells are derived from a stem cell. In some embodiments, the stem cell is a primary stem cell, an embryonic stem cell, a self-renewing stem cell, or an induced pluripotent stem cell.

In some embodiments, the animal cells are somatic cells. In some embodiments, the animal cells are not somatic cells.

In some embodiments, the animal cells are myogenic cells. In some embodiments, the animal cells are natively myogenic (e.g., are myogenic cells such as myoblasts, myocytes, satellite cells, side population cells, muscle derived stem cells, mesenchymal stem cells, myogenic pericytes, and mesoangioblasts that are cultured in the cultivation infrastructure). In some embodiments, the animal cells are not natively myogenic (e.g., are non-myogenic cells such as fibroblasts, preadipocytes, or non-myogenic stem cells that are cultured to become myogenic cells in the cultivation process).

In some embodiments, the animal cells have a skeletal muscle lineage. Cells of the skeletal muscle lineage include myoblasts, myocytes, and skeletal muscle progenitor cells, also called myogenic progenitors, that include satellite cells, side population cells, muscle derived stem cells, mesenchymal stem cells, myogenic pericytes, and mesoangioblasts. In some embodiments, the animal cells have a subcutaneous adipose tissue lineage. In some embodiments, the animal cells have a connective tissue lineage.

In some embodiments, the animal cells are derived from a myoblast cell line. In some embodiments, the animal cells are derived from a bovine myoblast cell line. In some embodiments, the animal cells are derived from a chicken myoblast cell line. In some embodiments, the animal cells are derived from a primary bovine myoblast cell line. In some embodiments, the animal cells are derived from a primary chicken myoblast cell line.

In some embodiments, the animal cells are derived from a fibroblast cell line. In some embodiments, the animal cells are derived from a bovine fibroblast cell line. In some embodiments, the animal cells are derived from a chicken fibroblast cell line. In some embodiments, the animal cells are derived from a primary bovine fibroblast cell line. In some embodiments, the animal cells are derived from a primary chicken fibroblast cell line.

In some embodiments, the animal cells of the present disclosure are not fully differentiated and are not in a meat-like structure. For example, in some embodiments, the animal cells have not formed muscle fibers. In some embodiments, the animal cells have not formed myotubes. In some embodiments, the animal cells are less than fully differentiated. In some embodiments, the animal cells are in suspension culture. The present inventors have discovered that animal cells in the presently disclosed hybrid meat substitute products do not have to be fully differentiated or form meat-like structures in order to mimic the experience of a fully meat product. Without wishing to be bound by any one theory, it is contemplated that the plant-based meat dough can mimic the meat-like texture, lessening the importance of texture of the animal cells. In some embodiments, animal cells are primarily provided for flavor, visual, and olfactory factors. This is an advantage of the presently disclosed hybrid meat substitute products over prior art cultivated meat products, because it obviates the need to go through expensive treatments to fully differentiate culture cells, or form meat-like structures.

It was previously not possible to use cultivated cells, and especially non-fully differentiated cultivated cells in hybrid meat products, because such cells accumulate extremely low levels of heme-containing proteins and the resulting product would fail to mimic meat products. The present disclosure solves this problem by supplementing the hybrid meat substitute product with exogenous heme-containing protein, which not only makes up for the deficiencies of the animal cells, but also over compensates for the fractional amount of animal cells in the meat substitute product. That is, in some embodiments, the present disclosure supplements exogenous heme-containing protein until the hybrid meat substitute product comprises a total heme containing protein content comparable to that of a full harvested meat equivalent product.

In some embodiments, the animal cells are derived from a preadipocyte cell line. In some embodiments, the animal cells are derived from a bovine preadipocyte cell line. In some embodiments, the animal cells are derived from a chicken preadipocyte cell line. In some embodiments, the animal cells are derived from a primary bovine preadipocyte cell line. In some embodiments, the animal cells are derived from a primary chicken preadipocyte cell line.

In some embodiments, the animal cells are derived from a non-immortalized cell line.

In some embodiments, the animal cells are derived from an immortalized cell line. In some embodiments, the disclosure provides methods for immortalizing primary cells isolated from an animal to increase the biomass of cultured cells generated or created from the isolated primary cells.

In some embodiments, the animal cells are substantially undifferentiated—for example, more than 70%, more than 75%, more than 80%, more than 85%, more than 90%, more than 95%, or 100% of the cell population is undifferentiated, including all ranges and subranges therebetween. In some embodiments, more than 90% of the cell population is undifferentiated.

In some embodiments, the animal cells are at least partially undifferentiated—for example, more than 30%, more than 35%, more than 40%, more than 45%, more than 50%, more than 55%, more than 60%, or more than 65%, of the cell population is undifferentiated, including all ranges and subranges therebetween. In some embodiments, 30%-70% of the cell population is undifferentiated.

In some embodiments, the animal cells are substantially differentiated—for example, more than 70%, more than 75%, more than 80%, more than 85%, more than 90%, more than 95%, or 100% (including all ranges and subranges therebetween) of the cell population is differentiated. In some embodiments, more than 90% of the cell population is differentiated.

In some embodiments, the present disclosure provides differentiated cells. In some embodiments, the animal cells are myoblasts or multinucleated myotubes differentiated from myogenic cells. In some embodiments, the differentiated cells are fibroblasts or adipogenic cells, mesenchymal stem cells, bone marrow derived cells, cardiomyocytes, or other cell types found in organ meat.

In some embodiments, differentiation comprises withdrawal of the culture medium that supports the viability, survival, growth or expansion of the cell population. Withdrawal may comprise physical removal of the culture medium or altering the composition of the culture medium, for example, by addition of components that would facilitate differentiation of the cell population or by depletion of components that support proliferation of the cell population.

In some embodiments, differentiation is induced by changes in cell density. In some embodiments, differentiation is induced by changes in availability of one or more nutrient factors and/or growth factor. In some embodiments, differentiation is induced by upregulating the expression of myocyte specific genes.

In some embodiments, the animal cells are genetically modified. In some embodiments, the genetically modified cells have one or more of the following characteristics: 1) capability of being adapted to suspension culture; 2) stability in suspension culture for an extended period of time; 3) capability of reaching a higher maximum viable cell density; 4) enhanced proliferation rate/mitotic potential; 5) reduced tendency to form cell aggregates; 6) resistance to apoptosis (e.g., anoikis); 7) tolerance of cell medium with reduced or no serum/growth factors (which otherwise would typically induce apoptosis); and/or 8) tolerance of industrial culture process. These characteristics are beneficial for cell culture in adherent and/or suspended states. In some embodiments, such characteristics are especially beneficial for industrial-scale production of myoblast cells in suspension culture.

It has been discovered that cells may be directed to proliferate beyond a finite lifespan by manipulating the cell cycle and maintaining telomere length. Inserting certain genes that regulate the cell cycle into the genome of cells provides a method of expanding the proliferative potential of cells and immortalizing cells. Inserted genes may code for proteins that promote progression of the cell cycle to proliferate the cell line, extend the lifespan of the cell or prevent senescence. Genetic amendments for increased or indefinite progression of the cell cycle include those that initiate telomerase reverse transcriptase activation, suppress p53 and retinoblastoma protein function, and activate Ras or c-Myc proto-oncogenes. In some embodiments, the disclosure provides methods for immortalizing or extending the proliferative capacity of cells to achieve cell proliferation by inserting immortalization genes, cell cycle regulator genes, genes that enhance cell cycle progression or genes that prevent senescence into a genome of a cell. Thereafter, the proliferative capacity may be decreased, after sufficient production has occurred, by excising the inserted genes, for example, as disclosed in WO2020/237021. Such immortalized cell lines offer significant advantage for industrial application (e.g., production of a large quantity of cells for preparing meat-like food products) as they can be used repeatedly for production during long campaigns and optimized for large scale culturing conditions with minimal batch-to-batch variation.

In some embodiments, the disclosure utilizes proteins that can deregulate the skeletal muscle cell cycle to increase the total number of cell divisions possible, a strategy that immortalizes a cell type that has an otherwise limited number of mitotic cell divisions in vitro.

In some embodiments, the animal cells do not comprise a heterologous antibiotic resistance gene.

In some embodiments, the animal cells of the disclosure may be further engineered to have improved meat-like properties; for example, the animal cells may be modified to overexpress a protein to improve the color or taste of the hybrid meat substitute product. In some embodiments, the animal cells may be modified in a way that generates or enhances the taste and smell of beef, bacon, pork, lamb, goat, turkey, duck, deer, yak, bison, chicken, or other desirable meat flavor in the food ingredient derived from such cells.

The animal cells may be from a wide variety of animal species, including without limitation livestock, poultry, wild animals, aquatic species, arthropod species, or other animals consumed by humans. Livestock includes without limitation cows, pigs, sheep, or goats. Poultry includes without limitation turkeys, chickens, or ducks. Other animals include without limitation deer. Aquatic species include fish but may also include other aquatic species. The cells and methods described herein are not limited to any particular species disclosed herein and contemplate all metazoan cell lines that can be used to manufacture animal cells.

In some embodiments, the animal cells are selected from the group consisting of bovine cells, porcine cells, ovine cells, chicken cells, turkey cells, and cells from an aquatic animal species. In some embodiments, the animal cells are bovine cells. In some embodiments, the animal cells are cow cells.

In some embodiments, the animal cells have a species identity of *Bos taurus, Sus scrofa, Capra aegagrus, Capra hircus* or *Ovis aries*. In some embodiments, the animal cells have a species identity of *Bos taurus, Bos indicus*, or a hybrid thereof (e.g., *Bos taurus* x *indicus*). In some embodiments, the animal cells are poultry cells. In some embodiments, the animal cells have a species identity of *Gallus gallus* (e.g., *Gallus gallus domesticus*), *Meleagris gallopavo, Anas platyrhynchos*, or *Coturnix coturnix*. In some embodiments, the animal cells are from an aquatic animal (e.g., traditional seafood and freshwater animals). In some embodiments, the animal cells have a species identity of *Salmo salar, Thunnus thynnus, Gadus morhua, Homarus americanus* or *Litopenaeus setiferus*.

In some embodiments, the hybrid meat substitute product comprises between 0.1-40% animal cells by weight. In some embodiments, the hybrid meat substitute product comprises about 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%, animal cells by weight, including all ranges and subranges therebetween. In some embodiments the weight of animal cells is calculated based on culture weight, of cells immediately after they are separated from their culture medium (e.g., after media separation from their suspension culture, or their equivalent).

In some embodiments, the hybrid meat substitute product comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, or 39%, animal cells by weight, including all ranges and subranges in between. In some embodiments, the hybrid meat substitute product comprises at least 2.5% animal cells by weight.

In some embodiments, the hybrid meat substitute product comprises no more than 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40%, animal cells by weight, including all ranges and subranges in between.

In some embodiments, the hybrid meat substitute product comprises between 0.1-0.5%, 0.5-1%, 1-2%, 2-3%, 3-4%, 4-5%, 5-6%, 6-7%, 7-8%, 8-9%, 9-10%, 10-12%, 12-15%, 15-20%, 20-25%, 25-30%, 30-35%, or 35-40%, animal cells by weight, including all ranges and subranges in between.

In some embodiments, the hybrid meat substitute product comprises between 0.1-1%, 0.5-2%, 1-3%, 2-4%, 3-5%, 4-6%, 5-7%, 6-8%, 7-9%, 8-10%, 9-12%, 10-15%, 12-20%, 15-25%, 20-30%, 25-35%, or 30-40%, animal cells by weight, including all ranges and subranges in between.

In some embodiments, the hybrid meat substitute product comprises between 0.1-2%, 0.5-3%, 1-4%, 2-5%, 3-6%, 4-7%, 5-8%, 6-9%, 7-10%, 8-12%, 9-15%, 10-20%, 12-25%, 15-30%, 20-35%, or 25-40%, animal cells by weight, including all ranges and subranges in between.

In some embodiments, the hybrid meat substitute product comprises between 0.1-3%, 0.5-4%, 1-5%, 2-6%, 3-7%, 4-8%, 5-9%, 6-10%, 7-12%, 8-15%, 9-20%, 10-25%, 12-30%, 15-35%, or 20-40%, animal cells by weight, including all ranges and subranges in between.

In some embodiments, the hybrid meat substitute product comprises between 3-10% animal cells by weight. In some embodiments, the hybrid meat substitute product comprises between 4-6%, 3-7%, or 2-8%, animal cells by weight, including all ranges and subranges in between. In some embodiments, the hybrid meat substitute product comprises between 9-11%, 8-12%, or 7-13%, animal cells by weight, including all ranges and subranges in between.

Combination of Animal Cells and Heme-Containing Protein

In some embodiments, the hybrid meat substitute product comprises animal cells and exogenous heme-containing protein at an amount according to one of the combinations listed in Table 1A below.

TABLE 1A

Combinations of Exogenous Heme-Containing Protein and Animal Cells

| Combination No. | Exogenous Heme-Containing Protein (w/w) | Animal Cells (w/w) |
|---|---|---|
| #1 | at least 0.25% | 2-5% |
| #2 | at least 0.4% | 2-5% |
| #3 | at least 0.5% | 2-5% |
| #4 | at least 0.7% | 2-5% |
| #5 | at least 1.0% | 2-5% |
| #6 | at least 1.5% | 2-5% |
| #7 | at least 2% | 2-5% |
| #8 | 0.25-0.5% | 2-5% |
| #9 | 0.5-1% | 2-5% |
| #10 | 0.5-1.5% | 2-5% |
| #11 | 0.5-2% | 2-5% |
| #12 | 0.5-5% | 2-5% |
| #13 | 1-1.5% | 2-5% |
| #14 | 1-2% | 2-5% |
| #15 | 1-5% | 2-5% |
| #16 | 1.5-2% | 2-5% |
| #17 | 1.5-5% | 2-5% |
| #18 | 2-5% | 2-5% |
| #19 | at least 0.25% | 2-10% |
| #20 | at least 0.4% | 2-10% |
| #21 | at least 0.5% | 2-10% |
| #22 | at least 0.7% | 2-10% |
| #23 | at least 1.0% | 2-10% |
| #24 | at least 1.5% | 2-10% |
| #25 | at least 2% | 2-10% |
| #26 | 0.25-0.5% | 2-10% |
| #27 | 0.5-1% | 2-10% |

TABLE 1A-continued

Combinations of Exogenous Heme-Containing Protein and Animal Cells

| Combination No. | Exogenous Heme-Containing Protein (w/w) | Animal Cells (w/w) |
|---|---|---|
| #28 | 0.5-1.5% | 2-10% |
| #29 | 0.5-2% | 2-10% |
| #30 | 0.5-5% | 2-10% |
| #31 | 1-1.5% | 2-10% |
| #32 | 1-2% | 2-10% |
| #33 | 1-5% | 2-10% |
| #34 | 1.5-2% | 2-10% |
| #35 | 1.5-5% | 2-10% |
| #36 | 2-5% | 2-10% |
| #37 | at least 0.25% | 2-20% |
| #38 | at least 0.4% | 2-20% |
| #39 | at least 0.5% | 2-20% |
| #40 | at least 0.7% | 2-20% |
| #41 | at least 1.0% | 2-20% |
| #42 | at least 1.5% | 2-20% |
| #43 | at least 2% | 2-20% |
| #44 | 0.25-0.5% | 2-20% |
| #45 | 0.5-1% | 2-20% |
| #46 | 0.5-1.5% | 2-20% |
| #47 | 0.5-2% | 2-20% |
| #48 | 0.5-5% | 2-20% |
| #49 | 1-1.5% | 2-20% |
| #50 | 1-2% | 2-20% |
| #51 | 1-5% | 2-20% |
| #52 | 1.5-2% | 2-20% |
| #53 | 1.5-5% | 2-20% |
| #54 | 2-5% | 2-20% |
| #55 | at least 0.25% | 5-10% |
| #56 | at least 0.4% | 5-10% |
| #57 | at least 0.5% | 5-10% |
| #58 | at least 0.7% | 5-10% |
| #59 | at least 1.0% | 5-10% |
| #60 | at least 1.5% | 5-10% |
| #61 | at least 2% | 5-10% |
| #62 | 0.25-0.5% | 5-10% |
| #63 | 0.5-1% | 5-10% |
| #64 | 0.5-1.5% | 5-10% |
| #65 | 0.5-2% | 5-10% |
| #66 | 0.5-5% | 5-10% |
| #67 | 1-1.5% | 5-10% |
| #68 | 1-2% | 5-10% |
| #69 | 1-5% | 5-10% |
| #70 | 1.5-2% | 5-10% |
| #71 | 1.5-5% | 5-10% |
| #72 | 2-5% | 5-10% |
| #73 | at least 0.25% | 5-20% |
| #74 | at least 0.4% | 5-20% |
| #75 | at least 0.5% | 5-20% |
| #76 | at least 0.7% | 5-20% |
| #77 | at least 1.0% | 5-20% |
| #78 | at least 1.5% | 5-20% |
| #79 | at least 2% | 5-20% |
| #80 | 0.25-0.5% | 5-20% |
| #81 | 0.5-1% | 5-20% |
| #82 | 0.5-1.5% | 5-20% |
| #83 | 0.5-2% | 5-20% |
| #84 | 0.5-5% | 5-20% |
| #85 | 1-1.5% | 5-20% |
| #86 | 1-2% | 5-20% |
| #87 | 1-5% | 5-20% |
| #88 | 1.5-2% | 5-20% |
| #89 | 1.5-5% | 5-20% |
| #90 | 2-5% | 5-20% |
| #91 | at least 0.25% | 10-20% |
| #92 | at least 0.4% | 10-20% |
| #93 | at least 0.5% | 10-20% |
| #94 | at least 0.7% | 10-20% |
| #95 | at least 1.0% | 10-20% |
| #96 | at least 1.5% | 10-20% |
| #97 | at least 2% | 10-20% |
| #98 | 0.25-0.5% | 10-20% |
| #99 | 0.5-1% | 10-20% |
| #100 | 0.5-1.5% | 10-20% |
| #101 | 0.5-2% | 10-20% |
| #102 | 0.5-5% | 10-20% |
| #103 | 1-1.5% | 10-20% |
| #104 | 1-2% | 10-20% |
| #105 | 1-5% | 10-20% |
| #106 | 1.5-2% | 10-20% |
| #107 | 1.5-5% | 10-20% |
| #108 | 2-5% | 10-20% |
| #109 | at least 0.25% | 10-30% |
| #110 | at least 0.4% | 10-30% |
| #111 | at least 0.5% | 10-30% |
| #112 | at least 0.7% | 10-30% |
| #113 | at least 1.0% | 10-30% |
| #114 | at least 1.5% | 10-30% |
| #115 | at least 2% | 10-30% |
| #116 | 0.25-0.5% | 10-30% |
| #117 | 0.5-1% | 10-30% |
| #118 | 0.5-1.5% | 10-30% |
| #119 | 0.5-2% | 10-30% |
| #120 | 0.5-5% | 10-30% |
| #121 | 1-1.5% | 10-30% |
| #122 | 1-2% | 10-30% |
| #123 | 1-5% | 10-30% |
| #124 | 1.5-2% | 10-30% |
| #125 | 1.5-5% | 10-30% |
| #126 | 2-5% | 10-30% |
| #127 | at least 0.25% | 15-30% |
| #128 | at least 0.4% | 15-30% |
| #129 | at least 0.5% | 15-30% |
| #130 | at least 0.7% | 15-30% |
| #131 | at least 1.0% | 15-30% |
| #132 | at least 1.5% | 15-30% |
| #133 | at least 2% | 15-30% |
| #134 | 0.25-0.5% | 15-30% |
| #135 | 0.5-1% | 15-30% |
| #136 | 0.5-1.5% | 15-30% |
| #137 | 0.5-2% | 15-30% |
| #138 | 0.5-5% | 15-30% |
| #139 | 1-1.5% | 15-30% |
| #140 | 1-2% | 15-30% |
| #141 | 1-5% | 15-30% |
| #142 | 1.5-2% | 15-30% |
| #143 | 1.5-5% | 15-30% |
| #144 | 2-5% | 15-30% |
| #145 | at least 0.25% | 20-30% |
| #146 | at least 0.4% | 20-30% |
| #147 | at least 0.5% | 20-30% |
| #148 | at least 0.7% | 20-30% |
| #149 | at least 1.0% | 20-30% |
| #150 | at least 1.5% | 20-30% |
| #151 | at least 2% | 20-30% |
| #152 | 0.25-0.5% | 20-30% |
| #153 | 0.5-1% | 20-30% |
| #154 | 0.5-1.5% | 20-30% |
| #155 | 0.5-2% | 20-30% |
| #156 | 0.5-5% | 20-30% |
| #157 | 1-1.5% | 20-30% |
| #158 | 1-2% | 20-30% |
| #159 | 1-5% | 20-30% |
| #160 | 1.5-2% | 20-30% |
| #161 | 1.5-5% | 20-30% |
| #162 | 2-5% | 20-30% |

In some embodiments, the hybrid meat substitute product comprises animal cells and total heme-containing protein at an amount according to one of the combinations listed in Table 1B below.

TABLE 1B

Combinations of Total Heme-Containing Protein and Animal Cells

| Combination No. | Total Heme-Containing Protein (w/w) | Animal Cells (w/w) |
|---|---|---|
| #1 | at least 0.25% | 2-5% |
| #2 | at least 0.4% | 2-5% |
| #3 | at least 0.5% | 2-5% |
| #4 | at least 0.7% | 2-5% |
| #5 | at least 1.0% | 2-5% |
| #6 | at least 1.5% | 2-5% |
| #7 | at least 2% | 2-5% |
| #8 | 0.25-0.5% | 2-5% |
| #9 | 0.5-1% | 2-5% |
| #10 | 0.5-1.5% | 2-5% |
| #11 | 0.5-2% | 2-5% |
| #12 | 0.5-5% | 2-5% |
| #13 | 1-1.5% | 2-5% |
| #14 | 1-2% | 2-5% |
| #15 | 1-5% | 2-5% |
| #16 | 1.5-2% | 2-5% |
| #17 | 1.5-5% | 2-5% |
| #18 | 2-5% | 2-5% |
| #19 | at least 0.25% | 2-10% |
| #20 | at least 0.4% | 2-10% |
| #21 | at least 0.5% | 2-10% |
| #22 | at least 0.7% | 2-10% |
| #23 | at least 1.0% | 2-10% |
| #24 | at least 1.5% | 2-10% |
| #25 | at least 2% | 2-10% |
| #26 | 0.25-0.5% | 2-10% |
| #27 | 0.5-1% | 2-10% |
| #28 | 0.5-1.5% | 2-10% |
| #29 | 0.5-2% | 2-10% |
| #30 | 0.5-5% | 2-10% |
| #31 | 1-1.5% | 2-10% |
| #32 | 1-2% | 2-10% |
| #33 | 1-5% | 2-10% |
| #34 | 1.5-2% | 2-10% |
| #35 | 1.5-5% | 2-10% |
| #36 | 2-5% | 2-10% |
| #37 | at least 0.25% | 2-20% |
| #38 | at least 0.4% | 2-20% |
| #39 | at least 0.5% | 2-20% |
| #40 | at least 0.7% | 2-20% |
| #41 | at least 1.0% | 2-20% |
| #42 | at least 1.5% | 2-20% |
| #43 | at least 2% | 2-20% |
| #44 | 0.25-0.5% | 2-20% |
| #45 | 0.5-1% | 2-20% |
| #46 | 0.5-1.5% | 2-20% |
| #47 | 0.5-2% | 2-20% |
| #48 | 0.5-5% | 2-20% |
| #49 | 1-1.5% | 2-20% |
| #50 | 1-2% | 2-20% |
| #51 | 1-5% | 2-20% |
| #52 | 1.5-2% | 2-20% |
| #53 | 1.5-5% | 2-20% |
| #54 | 2-5% | 2-20% |
| #55 | at least 0.25% | 5-10% |
| #56 | at least 0.4% | 5-10% |
| #57 | at least 0.5% | 5-10% |
| #58 | at least 0.7% | 5-10% |
| #59 | at least 1.0% | 5-10% |
| #60 | at least 1.5% | 5-10% |
| #61 | at least 2% | 5-10% |
| #62 | 0.25-0.5% | 5-10% |
| #63 | 0.5-1% | 5-10% |
| #64 | 0.5-1.5% | 5-10% |
| #65 | 0.5-2% | 5-10% |
| #66 | 0.5-5% | 5-10% |
| #67 | 1-1.5% | 5-10% |
| #68 | 1-2% | 5-10% |
| #69 | 1-5% | 5-10% |
| #70 | 1.5-2% | 5-10% |
| #71 | 1.5-5% | 5-10% |
| #72 | 2-5% | 5-10% |
| #73 | at least 0.25% | 5-20% |
| #74 | at least 0.4% | 5-20% |
| #75 | at least 0.5% | 5-20% |
| #76 | at least 0.7% | 5-20% |
| #77 | at least 1.0% | 5-20% |
| #78 | at least 1.5% | 5-20% |
| #79 | at least 2% | 5-20% |
| #80 | 0.25-0.5% | 5-20% |
| #81 | 0.5-1% | 5-20% |
| #82 | 0.5-1.5% | 5-20% |
| #83 | 0.5-2% | 5-20% |
| #84 | 0.5-5% | 5-20% |
| #85 | 1-1.5% | 5-20% |
| #86 | 1-2% | 5-20% |
| #87 | 1-5% | 5-20% |
| #88 | 1.5-2% | 5-20% |
| #89 | 1.5-5% | 5-20% |
| #90 | 2-5% | 5-20% |
| #91 | at least 0.25% | 10-20% |
| #92 | at least 0.4% | 10-20% |
| #93 | at least 0.5% | 10-20% |
| #94 | at least 0.7% | 10-20% |
| #95 | at least 1.0% | 10-20% |
| #96 | at least 1.5% | 10-20% |
| #97 | at least 2% | 10-20% |
| #98 | 0.25-0.5% | 10-20% |
| #99 | 0.5-1% | 10-20% |
| #100 | 0.5-1.5% | 10-20% |
| #101 | 0.5-2% | 10-20% |
| #102 | 0.5-5% | 10-20% |
| #103 | 1-1.5% | 10-20% |
| #104 | 1-2% | 10-20% |
| #105 | 1-5% | 10-20% |
| #106 | 1.5-2% | 10-20% |
| #107 | 1.5-5% | 10-20% |
| #108 | 2-5% | 10-20% |
| #109 | at least 0.25% | 10-30% |
| #110 | at least 0.4% | 10-30% |
| #111 | at least 0.5% | 10-30% |
| #112 | at least 0.7% | 10-30% |
| #113 | at least 1.0% | 10-30% |
| #114 | at least 1.5% | 10-30% |
| #115 | at least 2% | 10-30% |
| #116 | 0.25-0.5% | 10-30% |
| #117 | 0.5-1% | 10-30% |
| #118 | 0.5-1.5% | 10-30% |
| #119 | 0.5-2% | 10-30% |
| #120 | 0.5-5% | 10-30% |
| #121 | 1-1.5% | 10-30% |
| #122 | 1-2% | 10-30% |
| #123 | 1-5% | 10-30% |
| #124 | 1.5-2% | 10-30% |
| #125 | 1.5-5% | 10-30% |
| #126 | 2-5% | 10-30% |
| #127 | at least 0.25% | 15-30% |
| #128 | at least 0.4% | 15-30% |
| #129 | at least 0.5% | 15-30% |
| #130 | at least 0.7% | 15-30% |
| #131 | at least 1.0% | 15-30% |
| #132 | at least 1.5% | 15-30% |
| #133 | at least 2% | 15-30% |
| #134 | 0.25-0.5% | 15-30% |
| #135 | 0.5-1% | 15-30% |
| #136 | 0.5-1.5% | 15-30% |
| #137 | 0.5-2% | 15-30% |
| #138 | 0.5-5% | 15-30% |
| #139 | 1-1.5% | 15-30% |
| #140 | 1-2% | 15-30% |
| #141 | 1-5% | 15-30% |
| #142 | 1.5-2% | 15-30% |
| #143 | 1.5-5% | 15-30% |
| #144 | 2-5% | 15-30% |
| #145 | at least 0.25% | 20-30% |
| #146 | at least 0.4% | 20-30% |

TABLE 1B-continued

Combinations of Total Heme-Containing Protein and Animal Cells

| Combination No. | Total Heme-Containing Protein (w/w) | Animal Cells (w/w) |
|---|---|---|
| #147 | at least 0.5% | 20-30% |
| #148 | at least 0.7% | 20-30% |
| #149 | at least 1.0% | 20-30% |
| #150 | at least 1.5% | 20-30% |
| #151 | at least 2% | 20-30% |
| #152 | 0.25-0.5% | 20-30% |
| #153 | 0.5-1% | 20-30% |
| #154 | 0.5-1.5% | 20-30% |
| #155 | 0.5-2% | 20-30% |
| #156 | 0.5-5% | 20-30% |
| #157 | 1-1.5% | 20-30% |
| #158 | 1-2% | 20-30% |
| #159 | 1-5% | 20-30% |
| #160 | 1.5-2% | 20-30% |
| #161 | 1.5-5% | 20-30% |
| #162 | 2-5% | 20-30% |

Animal Fat

In one aspect, the present disclosure provides hybrid meat substitute product comprising animal fat.

In some embodiments, the animal fat of the present disclosure is harvested from one or more animals. In some embodiments, the animal fat is commercially sourced, such as butterfat, lard, tallow.

In some embodiments, the animal fat is processed and is separated from cell tissue. In some embodiments, animal fat is provided in the form of animal fat cells (e.g., adipocytes). In some embodiments, the animal fat is from cultivated cells.

In some embodiments, animal fat comprises fat-containing cells. In some embodiments, weight of the animal fat comprises weight of the cells that contain the fat. In the context of this disclosure (and in particular in the claims and further numbered embodiments), "animal fat cells" or "fat cells" provide the animal fat, and are distinct from "animal cells" or "animal muscle cells", which instead provide meat-like flavor. Persons having skill in the art will recognize however, that much of the discussion of animal cells in the sections of this document will also apply to animal fat cells (e.g., the "*Cell Cultivation for Meat Substitute Product*" section).

In some embodiments, the animal fat is obtained from cultivated fat cells. In some embodiments, the hybrid meat substitute product comprises the cultivated fat cells comprising the animal fat.

In some embodiments, the cultivated fat cells comprise, or are derived from, fibroblasts, mesenchymal stem cells, endothelial cells, adipose progenitor cells, preadipocytes, or adipocytes. In some embodiments, the fat cells are derived from fibroblasts. In some embodiments, the fat cells are adipose progenitor cells. In some embodiments, the fat cells are preadipocytes. In some embodiments, the fat cells are adipocytes. Generation and culturing of fat cells are described, for example, in Fernyhough et al., *Cytotechnology.* 2004 October; 46(2-3):163-72; Yin et al., *Biotechnol Lett.* 2010 February; 32(2):195-202; Nobuscue et al., *Cell Tissue Res.* 2008 June; 332(3):435-46; Liu et al., *Comp Biochem Physiol A Mol Integr Physiol.* 2009 September; 154(1):135-41; Wei et al., *Adipocyte.* 2013 Jul. 1; 2(3): 148-159; Gerlach et al., *Tissue Eng Part C Methods.* 2012 January; 18(1): 54-61; and Shang et al., *Biosci Rep.* 2014; 34(1): e00093, each of which is hereby incorporated in its entirety for all purposes.

In some embodiments, the fat cells are bovine cells, porcine cells, ovine cells, chicken cells, turkey cells, or cells from an aquatic animal species. In some embodiments, the fat cells are bovine cells.

In some embodiments, the fat cells are derived from a fibroblast cell line. In some embodiments, the fat cells are derived from a bovine fibroblast cell line. In some embodiments, fat cells are derived from a chicken fibroblast cell line. In some embodiments, the fat cells are derived from a primary bovine fibroblast cell line. In some embodiments, the fat cells are derived from a primary chicken fibroblast cell line.

In some embodiments, the fat cells are derived from a preadipocyte cell line. In some embodiments, the fat cells are derived from a bovine preadipocyte cell line (e.g., a cow preadipocyte cell line). In some embodiments, fat cells are derived from a chicken preadipocyte cell line. In some embodiments, the fat cells are derived from a primary bovine preadipocyte cell line. In some embodiments, the fat cells are derived from a primary chicken preadipocyte cell line.

In some embodiments, the fat cells are derived from an adipocyte cell line. In some embodiments, the fat cells are derived from a bovine adipocyte cell line. In some embodiments, fat cells are derived from a chicken adipocyte cell line. In some embodiments, the fat cells are derived from a primary bovine adipocyte cell line. In some embodiments, the fat cells are derived from a primary chicken adipocyte cell line.

In some embodiments, the cultivated fat cells are obtained from suspension culture.

In some embodiments, the fat cells are genetically modified. In some embodiments, the genetically modified cells have one or more of the following characteristics: 1) capability of being adapted to suspension culture; 2) stability in suspension culture for an extended period of time; 3) capability of reaching a higher maximum viable cell density; 4) enhanced proliferation rate/mitotic potential; 5) reduced tendency to form cell aggregates; 6) resistance to apoptosis (e.g., anoikis); 7) tolerance of cell medium with reduced or no serum/growth factors (which otherwise would typically induce apoptosis); and/or 8) tolerance of industrial culture process. These characteristics are beneficial for cell culture in adherent and/or suspended states. In some embodiments, such characteristics are especially beneficial for industrial-scale production of fat cells in suspension culture.

In some embodiments, the fat cells are somatic cells. In some embodiments, the fat cells are not somatic cells.

In some embodiments, the fat cells are derived from a non-immortalized cell line.

In some embodiments, the fat cells are from an immortalized cell line. In some embodiments, the disclosure provides methods for immortalizing primary cells isolated from an animal to increase the biomass of cultured cells generated or created from the isolated primary cells.

It has been discovered that cells may be directed to proliferate beyond a finite lifespan by manipulating the cell cycle and maintaining telomere length. Inserting certain genes that regulate the cell cycle into the genome of cells provides a method of expanding the proliferative potential of cells and immortalizing cells. Inserted genes may code for proteins that promote progression of the cell cycle to proliferate the cell line, extend the lifespan of the cell or prevent senescence. Genetic amendments for increased or indefinite progression of the cell cycle include those that initiate telomerase reverse transcriptase activation, suppress p53 and retinoblastoma protein function, and activate Ras or c-Myc proto-oncogenes. In some embodiments, the disclosure provides methods for immortalizing or extending the proliferative capacity of cells to achieve cell proliferation by inserting immortalization genes, cell cycle regulator genes, genes that enhance cell cycle progression or genes that prevent senescence into a genome of a cell. Thereafter, the proliferative capacity may be decreased, after sufficient production has occurred, by excising the inserted genes, for example, as disclosed in WO2020/237021. Such immortalized cell lines offer significant advantage for industrial application (e.g., production of a large quantity of cells for preparing meat-like food products) as they can be used repeatedly for production during long campaigns and optimized for large scale culturing conditions with minimal batch-to-batch variation.

In some embodiments, the fat cells do not comprise a heterologous antibiotic resistance gene.

The animal fat may be from a wide variety of animal species, including without limitation livestock, poultry, wild animals, aquatic species, arthropod species, or other animals consumed by humans. Livestock includes without limitation cows, pigs, sheep, or goats. Poultry includes without limitation turkeys, chickens, or ducks. Other animals include without limitation deer. Aquatic species include fish but may also include other aquatic species. The source of the animal fat described herein are not limited to any particular species disclosed herein and contemplate all metazoan species.

In some embodiments, the animal fat is from a *Bos taurus, Sus scrofa, Capra aegagrus, Capra hircus* or *Ovis aries* source. In some embodiments, the animal fat is from a species of *Bos taurus, Bos indicus*, or a hybrid thereof (e.g., *Bos taurus* x *indicus*). In some embodiments, the animal fat is originated from poultry. In some embodiments, the animal fat is originated from the species of *Gallus gallus* (e.g., *Gallus gallus domesticus*), *Meleagris gallopavo, Anas platyrhynchos*, or *Coturnix coturnix*. In some embodiments, the animal fat is originated from the species of an aquatic animal (e.g., traditional seafood and freshwater animals). In some embodiments, the animal fat is originated from the species of *Salmo salar, Thunnus thynnus, Gadus morhua, Homarus americanus* or *Litopenaeus setiferus*.

In some embodiments, the fat cells are selected from the group consisting of bovine cells, porcine cells, ovine cells, chicken cells, turkey cells, and cells from an aquatic animal species. In some embodiments, the fat cells are bovine cells. In some embodiments, the fat cells are cow cells.

In some embodiments, the hybrid meat substitute product comprises between 0.1-30% animal fat by weight. In some embodiments the weight of animal fat (when contained within animal fat cells) is calculated based on culture weight of cells (e.g., adipocytes) immediately after they are separated from their culture medium (e.g., after media separation from their suspension culture, or their equivalent).

In some embodiments, the hybrid meat substitute product comprises about 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, animal fat by weight, including all ranges and subranges therebetween. In some embodiments, the hybrid meat substitute product comprises about 15% animal fat by weight.

In some embodiments, the hybrid meat substitute product comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, animal fat by weight, including all ranges and subranges in between. In some embodiments, the hybrid meat substitute product comprises at least 2.5% animal fat by weight.

In some embodiments, the hybrid meat substitute product comprises no more than 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, animal fat by weight, including all ranges and subranges in between.

In some embodiments, the hybrid meat substitute product comprises between 0.1-0.5%, 0.5-1%, 1-2%, 2-3%, 3-4%, 4-5%, 5-6%, 6-7%, 7-8%, 8-9%, 9-10%, 10-12%, 12-15%, 15-20%, 20-25%, or 25-30%, animal fat by weight, including all ranges and subranges in between.

In some embodiments, the hybrid meat substitute product comprises between 0.1-1%, 0.5-2%, 1-3%, 2-4%, 3-5%, 4-6%, 5-7%, 6-8%, 7-9%, 8-10%, 9-12%, 10-15%, 12-20%, 15-25%, or 20-30%, animal fat by weight, including all ranges and subranges in between.

In some embodiments, the hybrid meat substitute product comprises between 0.1-2%, 0.5-3%, 1-4%, 2-5%, 3-6%, 4-7%, 5-8%, 6-9%, 7-10%, 8-12%, 9-15%, 10-20%, 12-25%, or 15-30%, animal fat by weight, including all ranges and subranges in between.

In some embodiments, the hybrid meat substitute product comprises between 5-15% animal fat by weight. In some embodiments, the hybrid meat substitute product comprises between 4-6%, 3-7%, or 2-8%, animal fat by weight, including all ranges and subranges in between. In some embodiments, the hybrid meat substitute product comprises between 9-11%, 8-12%, or 7-13%, animal fat by weight, including all ranges and subranges in between.

In some embodiments, the hybrid meat substitute product comprises between 5-30% animal fat by weight. In some embodiments, the hybrid meat substitute product comprises between 7-25%, 10-20%, or 12-18%, animal fat by weight, including all ranges and subranges in between. In some embodiments, the hybrid meat substitute product comprises between 10-30%, 12-25%, or 17-23%, animal fat by weight, including all ranges and subranges in between.

Combination of Animal Fat and Heme-Containing Protein

In some embodiments, the hybrid meat substitute product comprises animal fat and exogenous heme-containing protein at an amount according to one of the combinations listed in Table 2A below.

TABLE 2A

Combinations of Exogenous Heme-Containing Protein and Animal Fat

| Combination No. | Exogenous Heme-Containing Protein (w/w) | Animal Fat (w/w) |
| --- | --- | --- |
| #1 | at least 0.25% | 2-5% |
| #2 | at least 0.4% | 2-5% |
| #3 | at least 0.5% | 2-5% |
| #4 | at least 0.7% | 2-5% |
| #5 | at least 1.0% | 2-5% |
| #6 | at least 1.5% | 2-5% |
| #7 | at least 2% | 2-5% |
| #8 | 0.25-0.5% | 2-5% |
| #9 | 0.5-1% | 2-5% |
| #10 | 0.5-1.5% | 2-5% |
| #11 | 0.5-2% | 2-5% |
| #12 | 0.5-5% | 2-5% |
| #13 | 1-1.5% | 2-5% |
| #14 | 1-2% | 2-5% |
| #15 | 1-5% | 2-5% |

TABLE 2A-continued

Combinations of Exogenous Heme-Containing Protein and Animal Fat

| Combination No. | Exogenous Heme-Containing Protein (w/w) | Animal Fat (w/w) |
|---|---|---|
| #16 | 1.5-2% | 2-5% |
| #17 | 1.5-5% | 2-5% |
| #18 | 2-5% | 2-5% |
| #19 | at least 0.25% | 2-10% |
| #20 | at least 0.4% | 2-10% |
| #21 | at least 0.5% | 2-10% |
| #22 | at least 0.7% | 2-10% |
| #23 | at least 1.0% | 2-10% |
| #24 | at least 1.5% | 2-10% |
| #25 | at least 2% | 2-10% |
| #26 | 0.25-0.5% | 2-10% |
| #27 | 0.5-1% | 2-10% |
| #28 | 0.5-1.5% | 2-10% |
| #29 | 0.5-2% | 2-10% |
| #30 | 0.5-5% | 2-10% |
| #31 | 1-1.5% | 2-10% |
| #32 | 1-2% | 2-10% |
| #33 | 1-5% | 2-10% |
| #34 | 1.5-2% | 2-10% |
| #35 | 1.5-5% | 2-10% |
| #36 | 2-5% | 2-10% |
| #37 | at least 0.25% | 2-20% |
| #38 | at least 0.4% | 2-20% |
| #39 | at least 0.5% | 2-20% |
| #40 | at least 0.7% | 2-20% |
| #41 | at least 1.0% | 2-20% |
| #42 | at least 1.5% | 2-20% |
| #43 | at least 2% | 2-20% |
| #44 | 0.25-0.5% | 2-20% |
| #45 | 0.5-1% | 2-20% |
| #46 | 0.5-1.5% | 2-20% |
| #47 | 0.5-2% | 2-20% |
| #48 | 0.5-5% | 2-20% |
| #49 | 1-1.5% | 2-20% |
| #50 | 1-2% | 2-20% |
| #51 | 1-5% | 2-20% |
| #52 | 1.5-2% | 2-20% |
| #53 | 1.5-5% | 2-20% |
| #54 | 2-5% | 2-20% |
| #55 | at least 0.25% | 5-10% |
| #56 | at least 0.4% | 5-10% |
| #57 | at least 0.5% | 5-10% |
| #58 | at least 0.7% | 5-10% |
| #59 | at least 1.0% | 5-10% |
| #60 | at least 1.5% | 5-10% |
| #61 | at least 2% | 5-10% |
| #62 | 0.25-0.5% | 5-10% |
| #63 | 0.5-1% | 5-10% |
| #64 | 0.5-1.5% | 5-10% |
| #65 | 0.5-2% | 5-10% |
| #66 | 0.5-5% | 5-10% |
| #67 | 1-1.5% | 5-10% |
| #68 | 1-2% | 5-10% |
| #69 | 1-5% | 5-10% |
| #70 | 1.5-2% | 5-10% |
| #71 | 1.5-5% | 5-10% |
| #72 | 2-5% | 5-10% |
| #73 | at least 0.25% | 5-20% |
| #74 | at least 0.4% | 5-20% |
| #75 | at least 0.5% | 5-20% |
| #76 | at least 0.7% | 5-20% |
| #77 | at least 1.0% | 5-20% |
| #78 | at least 1.5% | 5-20% |
| #79 | at least 2% | 5-20% |
| #80 | 0.25-0.5% | 5-20% |
| #81 | 0.5-1% | 5-20% |
| #82 | 0.5-1.5% | 5-20% |
| #83 | 0.5-2% | 5-20% |
| #84 | 0.5-5% | 5-20% |
| #85 | 1-1.5% | 5-20% |
| #86 | 1-2% | 5-20% |
| #87 | 1-5% | 5-20% |
| #88 | 1.5-2% | 5-20% |
| #89 | 1.5-5% | 5-20% |
| #90 | 2-5% | 5-20% |
| #91 | at least 0.25% | 10-20% |
| #92 | at least 0.4% | 10-20% |
| #93 | at least 0.5% | 10-20% |
| #94 | at least 0.7% | 10-20% |
| #95 | at least 1.0% | 10-20% |
| #96 | at least 1.5% | 10-20% |
| #97 | at least 2% | 10-20% |
| #98 | 0.25-0.5% | 10-20% |
| #99 | 0.5-1% | 10-20% |
| #100 | 0.5-1.5% | 10-20% |
| #101 | 0.5-2% | 10-20% |
| #102 | 0.5-5% | 10-20% |
| #103 | 1-1.5% | 10-20% |
| #104 | 1-2% | 10-20% |
| #105 | 1-5% | 10-20% |
| #106 | 1.5-2% | 10-20% |
| #107 | 1.5-5% | 10-20% |
| #108 | 2-5% | 10-20% |
| #109 | at least 0.25% | 10-30% |
| #110 | at least 0.4% | 10-30% |
| #111 | at least 0.5% | 10-30% |
| #112 | at least 0.7% | 10-30% |
| #113 | at least 1.0% | 10-30% |
| #114 | at least 1.5% | 10-30% |
| #115 | at least 2% | 10-30% |
| #116 | 0.25-0.5% | 10-30% |
| #117 | 0.5-1% | 10-30% |
| #118 | 0.5-1.5% | 10-30% |
| #119 | 0.5-2% | 10-30% |
| #120 | 0.5-5% | 10-30% |
| #121 | 1-1.5% | 10-30% |
| #122 | 1-2% | 10-30% |
| #123 | 1-5% | 10-30% |
| #124 | 1.5-2% | 10-30% |
| #125 | 1.5-5% | 10-30% |
| #126 | 2-5% | 10-30% |
| #127 | at least 0.25% | 15-30% |
| #128 | at least 0.4% | 15-30% |
| #129 | at least 0.5% | 15-30% |
| #130 | at least 0.7% | 15-30% |
| #131 | at least 1.0% | 15-30% |
| #132 | at least 1.5% | 15-30% |
| #133 | at least 2% | 15-30% |
| #134 | 0.25-0.5% | 15-30% |
| #135 | 0.5-1% | 15-30% |
| #136 | 0.5-1.5% | 15-30% |
| #137 | 0.5-2% | 15-30% |
| #138 | 0.5-5% | 15-30% |
| #139 | 1-1.5% | 15-30% |
| #140 | 1-2% | 15-30% |
| #141 | 1-5% | 15-30% |
| #142 | 1.5-2% | 15-30% |
| #143 | 1.5-5% | 15-30% |
| #144 | 2-5% | 15-30% |
| #145 | at least 0.25% | 20-30% |
| #146 | at least 0.4% | 20-30% |
| #147 | at least 0.5% | 20-30% |
| #148 | at least 0.7% | 20-30% |
| #149 | at least 1.0% | 20-30% |
| #150 | at least 1.5% | 20-30% |
| #151 | at least 2% | 20-30% |
| #152 | 0.25-0.5% | 20-30% |
| #153 | 0.5-1% | 20-30% |
| #154 | 0.5-1.5% | 20-30% |
| #155 | 0.5-2% | 20-30% |
| #156 | 0.5-5% | 20-30% |
| #157 | 1-1.5% | 20-30% |
| #158 | 1-2% | 20-30% |
| #159 | 1-5% | 20-30% |

TABLE 2A-continued

Combinations of Exogenous Heme-Containing Protein and Animal Fat

| Combination No. | Exogenous Heme-Containing Protein (w/w) | Animal Fat (w/w) |
|---|---|---|
| #160 | 1.5-2% | 20-30% |
| #161 | 1.5-5% | 20-30% |
| #162 | 2-5% | 20-30% |

In some embodiments, the hybrid meat substitute product comprises animal fat and total heme-containing protein at an amount according to one of the combinations listed in Table 2B below.

TABLE 2B

Combinations of Total Heme-Containing Protein and Animal Fat

| Combination No. | Total Heme-Containing Protein (w/w) | Animal Fat (w/w) |
|---|---|---|
| #1 | at least 0.25% | 2-5% |
| #2 | at least 0.4% | 2-5% |
| #3 | at least 0.5% | 2-5% |
| #4 | at least 0.7% | 2-5% |
| #5 | at least 1.0% | 2-5% |
| #6 | at least 1.5% | 2-5% |
| #7 | at least 2% | 2-5% |
| #8 | 0.25-0.5% | 2-5% |
| #9 | 0.5-1% | 2-5% |
| #10 | 0.5-1.5% | 2-5% |
| #11 | 0.5-2% | 2-5% |
| #12 | 0.5-5% | 2-5% |
| #13 | 1-1.5% | 2-5% |
| #14 | 1-2% | 2-5% |
| #15 | 1-5% | 2-5% |
| #16 | 1.5-2% | 2-5% |
| #17 | 1.5-5% | 2-5% |
| #18 | 2-5% | 2-5% |
| #19 | at least 0.25% | 2-10% |
| #20 | at least 0.4% | 2-10% |
| #21 | at least 0.5% | 2-10% |
| #22 | at least 0.7% | 2-10% |
| #23 | at least 1.0% | 2-10% |
| #24 | at least 1.5% | 2-10% |
| #25 | at least 2% | 2-10% |
| #26 | 0.25-0.5% | 2-10% |
| #27 | 0.5-1% | 2-10% |
| #28 | 0.5-1.5% | 2-10% |
| #29 | 0.5-2% | 2-10% |
| #30 | 0.5-5% | 2-10% |
| #31 | 1-1.5% | 2-10% |
| #32 | 1-2% | 2-10% |
| #33 | 1-5% | 2-10% |
| #34 | 1.5-2% | 2-10% |
| #35 | 1.5-5% | 2-10% |
| #36 | 2-5% | 2-10% |
| #37 | at least 0.25% | 2-20% |
| #38 | at least 0.4% | 2-20% |
| #39 | at least 0.5% | 2-20% |
| #40 | at least 0.7% | 2-20% |
| #41 | at least 1.0% | 2-20% |
| #42 | at least 1.5% | 2-20% |
| #43 | at least 2% | 2-20% |
| #44 | 0.25-0.5% | 2-20% |
| #45 | 0.5-1% | 2-20% |
| #46 | 0.5-1.5% | 2-20% |
| #47 | 0.5-2% | 2-20% |
| #48 | 0.5-5% | 2-20% |
| #49 | 1-1.5% | 2-20% |
| #50 | 1-2% | 2-20% |
| #51 | 1-5% | 2-20% |
| #52 | 1.5-2% | 2-20% |
| #53 | 1.5-5% | 2-20% |
| #54 | 2-5% | 2-20% |
| #55 | at least 0.25% | 5-10% |
| #56 | at least 0.4% | 5-10% |
| #57 | at least 0.5% | 5-10% |
| #58 | at least 0.7% | 5-10% |
| #59 | at least 1.0% | 5-10% |
| #60 | at least 1.5% | 5-10% |
| #61 | at least 2% | 5-10% |
| #62 | 0.25-0.5% | 5-10% |
| #63 | 0.5-1% | 5-10% |
| #64 | 0.5-1.5% | 5-10% |
| #65 | 0.5-2% | 5-10% |
| #66 | 0.5-5% | 5-10% |
| #67 | 1-1.5% | 5-10% |
| #68 | 1-2% | 5-10% |
| #69 | 1-5% | 5-10% |
| #70 | 1.5-2% | 5-10% |
| #71 | 1.5-5% | 5-10% |
| #72 | 2-5% | 5-10% |
| #73 | at least 0.25% | 5-20% |
| #74 | at least 0.4% | 5-20% |
| #75 | at least 0.5% | 5-20% |
| #76 | at least 0.7% | 5-20% |
| #77 | at least 1.0% | 5-20% |
| #78 | at least 1.5% | 5-20% |
| #79 | at least 2% | 5-20% |
| #80 | 0.25-0.5% | 5-20% |
| #81 | 0.5-1% | 5-20% |
| #82 | 0.5-1.5% | 5-20% |
| #83 | 0.5-2% | 5-20% |
| #84 | 0.5-5% | 5-20% |
| #85 | 1-1.5% | 5-20% |
| #86 | 1-2% | 5-20% |
| #87 | 1-5% | 5-20% |
| #88 | 1.5-2% | 5-20% |
| #89 | 1.5-5% | 5-20% |
| #90 | 2-5% | 5-20% |
| #91 | at least 0.25% | 10-20% |
| #92 | at least 0.4% | 10-20% |
| #93 | at least 0.5% | 10-20% |
| #94 | at least 0.7% | 10-20% |
| #95 | at least 1.0% | 10-20% |
| #96 | at least 1.5% | 10-20% |
| #97 | at least 2% | 10-20% |
| #98 | 0.25-0.5% | 10-20% |
| #99 | 0.5-1% | 10-20% |
| #100 | 0.5-1.5% | 10-20% |
| #101 | 0.5-2% | 10-20% |
| #102 | 0.5-5% | 10-20% |
| #103 | 1-1.5% | 10-20% |
| #104 | 1-2% | 10-20% |
| #105 | 1-5% | 10-20% |
| #106 | 1.5-2% | 10-20% |
| #107 | 1.5-5% | 10-20% |
| #108 | 2-5% | 10-20% |
| #109 | at least 0.25% | 10-30% |
| #110 | at least 0.4% | 10-30% |
| #111 | at least 0.5% | 10-30% |
| #112 | at least 0.7% | 10-30% |
| #113 | at least 1.0% | 10-30% |
| #114 | at least 1.5% | 10-30% |
| #115 | at least 2% | 10-30% |
| #116 | 0.25-0.5% | 10-30% |
| #117 | 0.5-1% | 10-30% |
| #118 | 0.5-1.5% | 10-30% |
| #119 | 0.5-2% | 10-30% |
| #120 | 0.5-5% | 10-30% |
| #121 | 1-1.5% | 10-30% |
| #122 | 1-2% | 10-30% |
| #123 | 1-5% | 10-30% |
| #124 | 1.5-2% | 10-30% |
| #125 | 1.5-5% | 10-30% |
| #126 | 2-5% | 10-30% |

TABLE 2B-continued

Combinations of Total Heme-Containing Protein and Animal Fat

| Combination No. | Total Heme-Containing Protein (w/w) | Animal Fat (w/w) |
| --- | --- | --- |
| #127 | at least 0.25% | 15-30% |
| #128 | at least 0.4% | 15-30% |
| #129 | at least 0.5% | 15-30% |
| #130 | at least 0.7% | 15-30% |
| #131 | at least 1.0% | 15-30% |
| #132 | at least 1.5% | 15-30% |
| #133 | at least 2% | 15-30% |
| #134 | 0.25-0.5% | 15-30% |
| #135 | 0.5-1% | 15-30% |
| #136 | 0.5-1.5% | 15-30% |
| #137 | 0.5-2% | 15-30% |
| #138 | 0.5-5% | 15-30% |
| #139 | 1-1.5% | 15-30% |
| #140 | 1-2% | 15-30% |
| #141 | 1-5% | 15-30% |
| #142 | 1.5-2% | 15-30% |
| #143 | 1.5-5% | 15-30% |
| #144 | 2-5% | 15-30% |
| #145 | at least 0.25% | 20-30% |
| #146 | at least 0.4% | 20-30% |
| #147 | at least 0.5% | 20-30% |
| #148 | at least 0.7% | 20-30% |
| #149 | at least 1.0% | 20-30% |
| #150 | at least 1.5% | 20-30% |
| #151 | at least 2% | 20-30% |
| #152 | 0.25-0.5% | 20-30% |
| #153 | 0.5-1% | 20-30% |
| #154 | 0.5-1.5% | 20-30% |
| #155 | 0.5-2% | 20-30% |
| #156 | 0.5-5% | 20-30% |
| #157 | 1-1.5% | 20-30% |
| #158 | 1-2% | 20-30% |
| #159 | 1-5% | 20-30% |
| #160 | 1.5-2% | 20-30% |
| #161 | 1.5-5% | 20-30% |
| #162 | 2-5% | 20-30% |

Cell Cultivation for Meat Substitute Product

In one aspect, the present disclosure provides cells (animal cells and/or fat cells) that are cultivated in vitro. In some embodiments, the cells are cultivated in a suspension culture.

In some embodiments, the cells are cultivated in a cultivation infrastructure. A "cultivation infrastructure" refers to the environment in which the cell population (i.e., cellular biomass) are cultured. A cultivation infrastructure may be a tube, a cylinder, a flask, a petri-dish, a multi-well plate, a dish, a vat, an incubator, a bioreactor, an industrial fermenter and the like. A cultivation infrastructure may be a culture medium in which metazoan cells are cultured.

A cultivation infrastructure can be of any scale, and support any volume of cell population and culturing reagents. In some embodiments, the scale of the cultivation infrastructure ranges from about 10 μL to about 100,000 L. In some embodiments, the cultivation infrastructure is about 10 μL, about 100 μL, about 1 mL, about 10 mL, about 100 mL, about 1 L, about 10 L, about 100 L, about 1000 L, about 10,000 L, or even about 100,000 L, including all ranges and subranges therebetween.

A cultivation infrastructure may be sculpted into different sizes, shapes, and forms, as desired, to provide the shape and form for the cells to grow and resemble different types of tissues such as steak, tenderloin, shank, chicken breast, drumstick, lamb chops, fish fillet, lobster tail, etc. The cultivation infrastructure may be made from natural or synthetic biomaterials that are non-toxic so that they may not be harmful if ingested. Natural biomaterials may include, for example, collagen, fibronectin, laminin, or other extracellular matrices. Synthetic biomaterials may include, for example, hydroxyapatite, alginate, polyglycolic acid, polylactic acid, or their copolymers. The cultivation infrastructure may be formed as a solid or semisolid support.

In some embodiments, the cultivation infrastructure comprises a substrate. A cultivation infrastructure may comprise a permeable substrate (e.g., permeable to physiological solutions) or an impermeable substrate (e.g., impermeable to physiological solutions). In some embodiments, the cultivation infrastructure comprises a primary substrate, which can be a flat, concave, or convex substrate. In some embodiments, the cultivation infrastructure further comprises a secondary substrate, either introduced, or autologous, to direct cellular growth between the substrates, e.g. to direct attachment, proliferation and hypertrophy of cells on a plane perpendicular to the primary substrate. In some embodiments, the cultivation infrastructure comprises a hydrogel, a liquid cell culture medium, or soft agar. In some embodiments, the cultivation infrastructure does not comprise a substrate to which cells can adhere. In some embodiments, the cultivation infrastructure does not comprise an exogenously added scaffold (e.g., for promoting self-assembly of a three-dimensional cellular biomass. In some embodiments, the cultivation infrastructure does not comprise exogenous scaffolds such as a hydrogel or soft agar.

The cells may grow in the cultivation infrastructure as adherent, non-adherent, or suspension cell culture. In some embodiments, the cells comprise primarily adherent cells (e.g., those cells that adhere to a substrate) in the cultivation infrastructure. In some embodiments, the cells comprise primarily non-adherent cells (e.g., those cells that do not adhere to a substrate) in the cultivation infrastructure. In some embodiments, the cells comprise both adherent and non-adherent cells in the cultivation infrastructure. In some embodiments, the cells are in suspension culture, e.g. as a self-adhering biomass, or single-cell suspension in a liquid medium in the cultivation infrastructure. In some embodiments, while the cultivation infrastructure itself may have a three-dimensional structure or shape, the cells cultured in the cultivation infrastructure may form a monolayer of cells. In some embodiments, the cells cultivated in a cultivation infrastructure may self-assemble to form three-dimensional cellular biomass. In some embodiments, the culturing of cells in the cultivation infrastructure can induce the production of extracellular matrix (ECM) that may act as an autologous scaffold to direct three-dimensional cellular growth, e.g. to direct attachment, proliferation and hypertrophy of cells on a plane perpendicular to the substrate.

In some embodiments, the cultivation infrastructure is a bioreactor system. In some embodiments, the cells are grown in bioreactor systems in a single cell suspension, in cell aggregates, on microcarriers, or undergo a biofabrication step where they are synthesized together into tissue. In some embodiments, the cells are cultivated in a suspension culture. In some embodiment, the bioreactor system is a fed batch bioreactor. In some embodiments, the bioreactor system has a scale of at least 500-liter, at least 1,000-liter, at least 2,000-liter, at least 5,000-liter, at least 10,000-liter, at least 20,000-liter, or at least 50,000-liter. In some embodiments, the bioreactor system has a scale of at least 20,000-liter.

A bioreactor system is typically scalable for large-scale cell culture and is optimized for biomass production. The bioreactor system comprises a stirring element for agitation of the contents of the reactor chamber which helps to keep the cells in suspension. A temperature jacket provides temperature control to these cells. Oftentimes, the bioreactor system comprises at least one sensor for monitoring the reactor chamber. The at least one sensor is usually in communication with a control unit (e.g. a computer). Compressed air, Oxygen may be sterilely introduced (sparged) into the bioreactor to control dissolved oxygen content. Carbon dioxide and a suitable base may be introduced in the reactor to control pH. Fresh medium may be added into the bioreactor via at least one input port. Fresh medium is sometimes maintenance medium, differentiation medium, steatotic medium, proliferation medium, or any other medium formulation disclosed herein.

The cells may be grown until they reach a desired biomass. The desired biomass may be a biomass reached once the cells are no longer able to proliferate or may be the maximum biomass the cells can reach in a given culture size and culture conditions. In some embodiments, the maximum biomass is reached when the cells reach the maximum viable cell density.

In some embodiments, the cellular biomass is cultivated as a single-cell suspension culture. In some embodiments, the cellular biomass is cultivated in a suspension culture and forms self-adherent aggregates. A self-adherent aggregate refers to masses of viable cells suspended in a physiological liquid medium (e.g. suspension culture) aggregated due to, for example, their (1) adherence to each other (e.g. cadherin cell adhesion) (2) adherence to a basement membrane or other extracellular matrix secreted by the cells (e.g. integrin cell adhesion) or (3) a combination of both.

Additional description of in vitro cultivation of cells for meat substitute products can be found in Allan et al., *Front. Sustain. Food Syst.*, June 2019, Vol. 3, Article 44; Moritz et al., *Journal of Integrative Agriculture*, Vol 14, Issue 2, 2015, 14(2): 208-216; and Zhang et al., *Trends in food science & technology*, 2020 v.97 pp. 443-450, each of which is hereby incorporated by reference in its entirety.

Plant-Based Meat Dough

In some embodiments, the hybrid meat substitute product comprises a plant-based meat dough that comprises proteins, lipids, carbohydrates, cells, or other ingredients derived from one or more plant or modified plant sources. In some embodiments, the hybrid meat substitute product (or the plant-based meat dough more specifically) comprises plant-based protein or product. Examples of suitable plants include but are not limited to spermatophytes (spermatophyta), acrogymnospermae, angiosperms (magnoliophyta), ginkgoidae, pinidae, mesangiospermae, cycads, Ginkgo, conifers, gnetophytes, *Ginkgo biloba*, cypress, junipers, thuja, cedarwood, pines, angelica, caraway, coriander, cumin, fennel, parsley, dill, dandelion, helichrysum, marigold, mugwort, safflower, chamomile, lettuce, wormwood, calendula, citronella, sages, thyme, chia seed, mustard, olive, coffee, capsicum, eggplant, paprika, cranberry, kiwi, vegetable plants (e.g., carrot, celery), tagetes, tansy, tarragon, sunflower, wintergreen, basil, hyssop, lavender, lemon verbena, marjoram, melissa, patchouli, pennyroyoal, peppermint, rosemary, sesame, spearmint, primroses, samara, pepper, pimento, potato, sweet potato, tomato, blueberry, nightshades, petunia, morning glory, lilac, jasmin, honeysuckle, snapdragon, psyllium, wormseed, buckwheat, amaranth, chard, quinoa, spinach, rhubarb, jojoba, cypselea, chlorella, manila, hazelnut, canola, kale, bok choy, rutabaga, frankincense, myrrh, elemi, hemp, pumpkin, squash, curcurbit, manioc, dalbergia, legume plants (e.g., alfalfa, lentils, beans, clovers, peas, fava coceira, frijole bola roja, frijole negro, lespedeza, licorice, lupin, mesquite, carob, soybean, peanut, tamarind, wisteria, cassia, chickpea, garbanzo, fenugreek, green pea, yellow pea, snow pea, yellow pea, lima bean, fava bean), geranium, flax, pomegranate, cotton, okra, neem, fig, mulberry, clove, eucalyptus, tea tree, niaouli, fruiting plants (e.g, apple, apricot, peach, plum, pear, nectarine), strawberry, blackberry, raspberry, cherry, prune, rose, tangerine, citrus (e.g., grapefruit, lemon, lime, orange, bitter orange, mandarin), mango, citrus bergamot, buchu, grape, broccoli, brussels, sprout, camelina, cauliflower, rape, rapeseed (canola), turnip, cabbage, cucumber, watermelon, honeydew melon, zucchini, birch, walnut, cassava, baobab, allspice, almond, breadfruit, sandalwood, macadamia, taro, tuberose, aloe vera, garlic, onion, shallot, vanilla, yucca, vetiver, galangal, barley, corn, *Curcuma aromatica*, galangal, ginger, lemon grass, oat, palm, pineapple, rice, rye, sorghum, triticale, turmeric, yam, bamboo, barley, cajuput, canna, cardamom, maize, oat, wheat, cinnamon, sassafras, *Lindera benzoin*, bay laurel, avocado, ylang-ylang, mace, nutmeg, moringa, horsetail, oregano, cilantro, chervil, chive, aggregate fruits, grain plants, herbal plants, leafy vegetables, non-grain legume plants, nut plants, succulent plants, land plants, water plants, delbergia, millets, drupes, schizocarps, flowering plants, non-flowering plants, cultured plants, wild plants, trees, shrubs, flowers, grasses, herbaceous plants, brushes, lianas, cacti, green algae, tropical plants, subtropical plants, temperate plants, and derivatives and crosses thereof.

In some embodiments, the plant is selected from alfalfa, bamboo, barley, beets, black beans, broccoli, cabbage, canola, carrot, cauliflower, celery, celery root, chickpeas, corn, cotton, cow peas, fava beans, flax, garbanzo beans, green beans, kale, kidney beans, lupin, mung beans, navy beans, northern beans, nuts, oats, parsley, pearl millet, peas, pine nuts, pinto beans, potato, quinoa, red beans, rice, sesame, soy, spelt, sugarbeet, sunflowers, sweet potato, tobacco, wheat, white beans, whole grains, wild rice, zucchini, and a mixture thereof.

Modified plant sources may be obtained from a variety of sources including but not limited to commercial products (e.g., GMO fruits and veggies), commercial cell banks (e.g., ATCC, collaborative sources), or can be generated from natural plants by methods known in the art, including selection, mutation, or gene manipulation. Selection generally involves continuous multiplication and steady increase in dilution rates under selective pressure. Mutation generally involves selection after exposure to mutagenic agents. Gene manipulation generally involves genetic engineering (e.g., gene splicing, insertion of deletions or modifications by homologous recombination) of target genes. A modified plant source may produce a non-native protein, carbohydrate, lipid, or other compound, or produce a non-native amount of a native protein, carbohydrate, lipid, or other compound. In some embodiments, the modified plant source expresses higher or lower levels of a native protein or metabolic pathway compound. In other such embodiments, the modified plant source expresses one or more novel recombinant proteins, RNAs, or metabolic pathway components derived from another plant, algae, microbe, or fungus. In other embodiments, the modified plant source has an increased nutraceutical content compared to its native state. In yet other embodiments, the modified plant source has more favorable growth and production characteristics compared to its native state. In some such embodiments, the modified plant source has an increased specific growth rate compared to its native state. In other such embodiments, the modified plant source can utilize a different carbon source than its native state.

In some embodiments, the plant-based meat dough within the hybrid meat substitute product comprises plant-based proteins. In some embodiments, the plant-based proteins comprise protein isolates (e.g., from potato, soy, pea, lentil, chickpea, lupin, oat, canola, wheat), hydrolyzed protein isolates (e.g., hydrolyzed pea protein isolate, hydrolyzed soy protein isolate), protein concentrates (e.g. from algae, lentil, pea, soy, chickpea, rice, hemp, fava bean, pigeon pea, cowpea, vital wheat gluten), native or relatively folded (i.e., not fully in the native functional state but not fully denatured) proteins (e.g., fava protein, lentil protein, pea protein, chickpea protein, mung bean protein, pigeon pea protein, lupin bean protein, soybean protein, white bean protein, black bean protein, navy bean protein, adzuki bean protein, sunflower seed protein), and/or prolamin proteins (e.g., Zein protein). In some embodiments, the plant-based proteins comprise gluten proteins, pulse proteins, legume proteins, mycoprotein, rice proteins, potato proteins, oat proteins, soy proteins, pea proteins, chickpea proteins, canola proteins, algae proteins, hemp proteins, or a mixture thereof. In some embodiments, the plant-based proteins are isolated proteins, texturized proteins, or mixtures thereof. In some embodiments, the plant-based proteins comprise a ribulose-1,5-bisphosphate carboxylase/oxygenase (RuBisCO), an albumin, a gluten, a conglycinin, or mixtures thereof.

In some embodiments, the hybrid meat substitute product (or the plant-based meat dough more specifically) comprises one or more edible fibrous components (fibers). In some embodiments, the edible fibrous component of the hybrid meat substitute product (or the plant-based meat dough more specifically) comprises plant fibers from carrot, bamboo, pea, broccoli, potato, sweet potato, corn, whole grains, alfalfa, kale, celery, celery root, citrus, parsley, cabbage, zucchini, green beans, kidney beans, black beans, red beans, white beans, beets, cauliflower, nuts, apple, citrus, oats, wheat, or psyllium, or a mixture thereof. In some embodiments, the edible fibrous component comprises an extruded mixture of isolated plant proteins. In some embodiments, the extruded mixture comprises wheat gluten and soy protein isolate, and optionally further comprises a flavoring agent (e.g., a flavoring such as yeast extract, a protein hydrolysate, or an oil; a flavor compound; or a flavor precursor). In some embodiments, the edible fibrous component comprises a solution-spun protein fiber (e.g., a solution-spun protein fiber containing a prolamin such as corn zein, pea prolamin, kafirin, secalin, hordein, avenin, or a mixture thereof).

In some embodiments, the hybrid meat substitute product (or the plant-based meat dough more specifically) comprises one or more types of mushrooms. In some embodiments, the mushrooms are selected from the group consisting of Shiitake mushrooms, porcini mushrooms, white buttons mushroom, brown buttons mushroom, portobello mushrooms, cremini mushrooms, maitake mushrooms, lobster mushrooms, Enoki mushrooms, clamshell mushrooms, other fleshy, spore-bearing fruiting body of fungi, or mixtures thereof. In some embodiments, the mushrooms are pureed.

In some embodiments, the hybrid meat substitute product (e.g., plant-based meat dough) comprises one or more fats. That is, in some embodiments, the hybrid meat substitute products of the present disclosure comprise non-animal fat in the plant-based meat dough, and animal fat. In some embodiments, the fat is a non-animal fat. In some embodiments, the non-animal fat comprise an algal oil, a fungal oil, corn oil, olive oil, soy oil, peanut oil, walnut oil, almond oil, sesame oil, cottonseed oil, rapeseed oil, canola oil, safflower oil, sunflower oil, flax seed oil, palm oil, palm kernel oil, coconut oil, babassu oil, shea butter, mango butter, cocoa butter, wheat germ oil, borage oil, black currant oil, sea-buckhorn oil, macadamia oil, saw palmetto oil, conjugated linoleic oil, arachidonic acid enriched oil, docosahexaenoic acid (DHA) enriched oil, eicosapentaenoic acid (EPA) enriched oil, palm stearic acid, sea-buckhorn berry oil, macadamia oil, saw palmetto oil, rice bran oil, other vegetable oil, or margarine or other hydrogenated fats. In some embodiments, the fat comprises algal oil. In some embodiments, the fat comprises the flavoring agent and/or the isolated plant protein (e.g., a conglycinin protein).

In some embodiments, the hybrid meat substitute product (or the plant-based meat dough before animal cells are added) comprises between 0.1-30% non-animal fat by weight. In some embodiments, the hybrid meat substitute product (or the plant-based meat dough before animal cells are added) comprises about 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, non-animal fat by weight, including all ranges and subranges therebetween. In some embodiments, the hybrid meat substitute product (or the plant-based meat dough, before animal cells are added) comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, non-animal fat by weight, including all ranges and subranges in between. In some embodiments, the hybrid meat substitute product (or the plant-based meat dough before the animal cells are added) comprises no more than 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, non-animal fat by weight, including all ranges and subranges in between. In some embodiments, the hybrid meat substitute product (or the plant-based meat dough before the animal cells are added) comprises between 0.1-0.5%, 0.5-1%, 1-2%, 2-3%, 3-4%, 4-5%, 5-6%, 6-7%, 7-8%, 8-9%, 9-10%, 10-12%, 12-15%, 15-20%, 20-25%, or 25-30%, non-animal fat by weight, including all ranges and subranges in between. In some embodiments, the hybrid meat substitute product (or the plant-based meat dough before the animal cells are added) comprises between 0.1-1%, 0.5-2%, 1-3%, 2-4%, 3-5%, 4-6%, 5-7%, 6-8%, 7-9%, 8-10%, 9-12%, 10-15%, 12-20%, 15-25%, or 20-30%, non-animal fat by weight, including all ranges and subranges in between. In some embodiments, the hybrid meat substitute product (or the plant-based meat dough before the animal cells are added) comprises between 0.1-2%, 0.5-3%, 1-4%, 2-5%, 3-6%, 4-7%, 5-8%, 6-9%, 7-10%, 8-12%, 9-15%, 10-20%, 12-25%, or 15-30%, non-animal fat by weight, including all ranges and subranges in between. In some embodiments, the hybrid meat substitute product (or the plant-based meat dough before the animal cells are added) comprises between 5-10% non-animal fat by weight. In some embodiments, the hybrid meat substitute product (or the plant-based meat dough before the animal cells are added) comprises between 4-6%, 3-7%, or 2-8%, non-animal fat by weight, including all ranges and subranges in between. In some embodiments, the hybrid meat substitute product comprises between 9-11%, 8-12%, or 7-13%, non-animal fat by weight, including all ranges and subranges in between.

In some embodiments, the hybrid meat substitute product of the present disclosure comprises both animal fat, and non-animal fat. Total Fat Content comprises both the animal fat and the non-animal fat content of the hybrid meat substitute product.

In some embodiments, the hybrid meat substitute product comprises one or more binding agents. Traditional veggie meat substitute products utilize methylcellulose as the primary binding agent. In some embodiments, the hybrid meat substitute product of the present disclosure does not use any methylcellulose. In some embodiments, the animal cells of the present disclosure act as a binder for the hybrid meat substitute product. Thus, in some embodiments, the presently disclosed hybrid meat substitute products comprise fewer artificial ingredients.

In some embodiments, the binding agent is provided within the plant-based meat dough. In some embodiments, the binding agent is provided as a separate ingredient. In some embodiments, the binding agent comprises an isolated plant protein (e.g., a RuBisCO, an albumin, a gluten, a conglycinin, or mixtures thereof). In some embodiments, the denaturation temperature of the binding agent is between about 40° C. and about 80° C. In some embodiments, the hybrid meat substitute product comprise at least about 0.01%, between about 0.01% and about 15%, between about 0.1% and about 10%, between about 0.25% and about 7%, between about 0.25% and about 5%, between about 0.5% and about 4.5%, between about 1% and about 4%, between about 1.5% and about 3.5%, between about 2% and about 3%, between about 1% and about 2.5%, between about 2% and about 2.5%, between about 0.5% and about 2%, or between about 5% and about 10% (including all ranges and subranges therebetween) by weight of binding agents.

Examples of suitable binding agents include but are not limited to purees (e.g., bean puree, sweet potato puree, pumpkin puree, applesauce, yam puree, banana puree, plantain puree, date puree, prune puree, fig puree, zucchini puree, carrot puree, coconut puree), native or modified starches (e.g., starches from grains, starches from tuber, potato starch, sweet potato starch, corn starch, waxy corn starch, tapioca starch, tapioca, arrowroot starch, taro starch, pea starch, chickpea starch, rice starch, waxy rice starch, lentil starch, barley starch, sago, sorghum starch, wheat starch, and physical or chemical modifications thereof [including, e.g., pre-gelatinized starch, acetylated starch, phosphate bonded starch, carboxymethylat-ed starch, hydroxypropylated starch]), flours derived from grains or legumes or roots (e.g., from taro, banana, jackfruit, konjac, lentil, fava, lupin bean, pea, bean, rice, wheat, barley, rye, corn, sweet rice, soy, teff, buckwheat, amaranth, chickpea, sorghum, almond, chia seed, flaxseed, potato, tapioca, potato), protein isolates (e.g., from potato, soy, pea, lentil, chickpea, lupin, oat, canola, wheat), hydrolyzed protein isolates (e.g., hydrolyzed pea protein isolate, hydrolyzed soy protein isolate), protein concentrates (e.g. from algae, lentil, pea, soy, chickpea, rice, hemp, fava bean, pigeon pea, cowpea, vital wheat gluten), beta-glucans (e.g., from bacteria (e.g., curdlan), oat, rye, wheat, yeast, barley, algae, mushroom), gums (e.g., xanthan gum, guar gum, locust bean gum, gellan gum, gum arabic, vegetable gum, tara gum, tragacanth gum, konjac gum, fenugreek gum, gum karaya, gellan gum, high-acetyl gellan gum, low-acetyl gellan gum), native or relatively folded (i.e., not fully in the native functional state but not fully denatured) proteins (e.g., fava protein, lentil protein, pea protein, ribulose-1,5-bisphosphate carboxylase/oxygenase [Rubisco], chickpea protein, mung bean protein, pigeon pea protein, lupin bean protein, soybean protein, white bean protein, black bean protein, navy bean protein, adzuki bean protein, sunflower seed protein), polysaccharides and modified polysaccharides (e.g., methylcellulose, hydroxypropyl methylcellulose, carboxymethyl cellulose, maltodextrin, carrageenan and its salts, kelp and kelp extracts, alginic acid and its salts, agar, agarose, agaropectin, pectin, alginate), nut and seed butters (e.g., almond butter, cashew butter, hazelnut butter, macadamia nut butter, peanut butter, pecan butter, pistachio butter, walnut butter, pumpkin seed butter, sesame seed butter, soybean butter, sunflower seed butter), enzymes (e.g., trans-glutaminase, thio-oxidoreductase), prolamin proteins (e.g., Zein protein), gelatin, egg protein, potato flakes, okra, tubers, fibers (e.g., psyllium husk), and derivatives and combinations thereof. In some embodiments, the binding agent comprises egg albumin or collagen.

In some embodiments, the hybrid meat substitute products comprise between about 0.1% and about 4%, between about 0.25% and about 1.5%, between about 0.5% and about 1.25%, between about 0.75% and about 1%, between about 1% and about 1.5%, between about 1.5% and about 2%, between about 2% and about 2.5%, between about 2.5% and about 3%, or between about 3% and about 4% by weight of starch.

Suitable binding agents and suitable amounts of such binding agents can be identified by titrating different binding agents against the cohesiveness, binding, and malleability of uncooked meat-like food products, or against the cohesiveness and binding of cooked meat-like food products. The presence and distribution of carbohydrates used as binders in a meat-like food product provided herein can be determined by methods known in the art, such as, for example, methods that involve microscopic observation using brightfield, fluorescence, or phase contrast microscopy of thin strips of refrigerated meat-like food product stained with a natural or fluorescent dye that selectively stains carbohydrates.

In some embodiments, the binding agent comprises methylcellulose, hydroxypropylmethyl cellulose, guar gum, locust bean gum, xanthan gum, agar, pectin, carrageenan, konjac, alginate, chemically-modified agarose, or mixtures thereof. In some embodiments, the binding agent comprises methylcellulose and/or its derivative. Derivatives of methylcellulose, such as hydroxypropylmethylcellulose (HPMC) and hydroxyethylmethylcellulose (HEMC), are well known in the art (see, e.g., Grover, Industrial Gums (Third Edition), Polysaccharides and Their Derivatives, 1993, pages 475-504, the content of which is incorporated by reference in its entirety for all purposes). In some embodiments, the binding agent is methylcellulose. In some embodiments, the hybrid meat substitute products comprise between about 0.5% and about 5%, between about 1% and about 4%, between about 2% and about 3%, between about 1% and about 2%, between about 3% and about 4%, between about 4% and about 5%, between about 0.5% and about 1.5%, or between about 1% and about 1.5% (including all ranges and subranges therebetween) by weight of the binding agent.

In some embodiments, the binding agent is formulated in a carbohydrate-based gel. An example of a carbohydrate-based gel comprising methylcellulose is methylcellulose emulsion. In some embodiments, the carbohydrate-based gel of the hybrid meat substitute product has a melting temperature between about 45° C. and about 85° C. In some embodiments, the carbohydrate-based gel becomes firm upon cooking (e.g., to 140° F. to 190° F.). In some embodiments, the carbohydrate-based gel comprises methylcellulose, hydroxypropylmethyl cellulose, guar gum, locust bean gum, xanthan gum, agar, pectin, carrageenan, konjac, alginate, chemically-modified agarose, or mixtures thereof. In some embodiments, the carbohydrate-based gel comprises methylcellulose and/or its derivative. In some embodiments, the carbohydrate-based gel comprises methylcellulose. In some embodiments, the hybrid meat substitute products comprise at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% (including all ranges and subranges therebetween) by weight of the carbohydrate-based gel. In some embodiments, the hybrid meat substitute products comprise at most 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% (including all ranges and subranges therebetween) by weight of the carbohydrate-based gel. In some embodiments, the hybrid meat substitute products comprise between 1-2%, 2-3%, 3-4%, 4-5%, 5-6%, 6-7%, 7-8%, 8-9%, 9-10%, 10-12%, 12-15%, 15-20%, 20-25%, or 25-30% (including all ranges and subranges therebetween) by weight of the carbohydrate-based gel. In some embodiments, the hybrid meat substitute products comprise between 1-3%, 2-4%, 3-5%, 4-6%, 5-7%, 6-8%, 7-9%, 8-10%, 9-12%, 10-15%, 12-20%, 15-25%, or 20-30% (including all ranges and subranges therebetween) by weight of the carbohydrate-based gel.

In some embodiments, the hybrid meat substitute product (or the plant-based meat dough) comprises no binding agent. In some embodiments, the hybrid meat substitute product (or the plant-based meat dough) comprises no methylcellulose. In some embodiments, the animal cells in the hybrid meat substitute product act as a binder, thereby removing the need for any additional binding agent.

In some embodiments, the hybrid meat substitute product (or the plant-based meat dough before the animal cells are added) comprises one or more flavoring agents. In some embodiments, the flavoring agent is selected from the group consisting of a vegetable extract, a fruit extract, an acid, an antioxidant, a carotenoid, a lactone, and any combinations thereof. In some embodiments, the antioxidant is epigallocatechin gallate. In some embodiments, the carotenoid is lutein, 3-carotene, zeaxanthin, trans-(3-apo-8'-carotenal) lycopene, or canthaxanthin. In some embodiments, the vegetable extract is from a cucumber or tomato. In some embodiments, the fruit extract is from a melon or pineapple. The amount of flavoring agents can vary depending on the type of flavoring agent. In some embodiments, a flavoring agent can be about 0.5% to about 7% of the hybrid meat substitute product. For example, a flavoring agent such as a mixture of flavor precursors can be about 0.5% to about 7% of the hybrid meat substitute product (e.g., about 1% to about 3%; about 3% to about 6%; about 4% to about 7%). In some embodiments, a flavoring agent such as a flavoring compound can be about 0.00001% to about 5% of the hybrid meat substitute product.

In some embodiments, the hybrid meat substitute product (or the plant-based meat dough before the animal cells are added) comprises one or more pH adjusting agents. In some embodiments, the pH adjusting agent is an acid. In some embodiments, the pH adjusting agent is a base. In some embodiments, the pH adjusting agent is selected from acetic acid, lactic acid, glycolic acid, citric acid, succinic acid, tartaric acid, caprylic acid, capric acid, lauric acid, myristic acid, palmitic acid, palmitoleic acid, stearic acid, oleic acid, linoleic acid, alpha linolenic acid, gamma linolenic acid, arachidic acid, arachidonic acid, behenic acid, erucic acid, and glucan delta lactone. In some embodiments, the pH of the hybrid meat substitute product is between 4-8. In some embodiments, the pH of the hybrid meat substitute product is between 4-7, 5-8, 4-6, 5-7, 6-8, 4-5, 5-6, 6-7, or 7-8, including all ranges and subranges there between. In some embodiments, the pH of the hybrid meat substitute product is between 4.0-4.3, 4.2-4.5, 4.4-4.7, 4.6-4.9, 4.8-5.1, 5.0-5.3, 5.2-5.5, 5.4-5.7, 5.6-5.9, 5.8-6.1, 6.0-6.3, 6.2-6.5, 6.4-6.7, 6.6-6.9, 6.8-7.1, 7.0-7.3, 7.2-7.5, 7.4-7.7, 7.6-7.9, or 7.8-8.1, including all ranges and subranges therebetween.

Properties of the Hybrid Meat Substitute Product

In some embodiments, the hybrid meat substitute product resembles ground animal meat (e.g., ground beef, ground chicken, ground turkey, ground lamb, or ground pork). In some embodiments, the hybrid meat substitute product resembles a burger patty. In some embodiments, the hybrid meat substitute product is principally composed of ingredients derived from non-animal sources. In some embodiments, the hybrid meat substitute product is composed of ingredients partially derived from animal sources but supplemented with ingredients derived from non-animal sources.

In some embodiments, the animal cells and the plant-based meat dough are bound together by one or more binding agents, which can produce hybrid meat substitute product that have one or more similar or superior attributes compared to animal meat. In some embodiments, the hybrid meat substitute product incorporates one or more edible fibrous components, which can help achieve a textural heterogeneity and fibrousness in the hybrid meat substitute product that resembles the heterogeneity and texture of animal meat. In some embodiments, the hybrid meat substitute product incorporates one or more flavoring agents, which can help mimic the sensory properties of ground meat.

In some embodiments, the hybrid meat substitute product comprises about 1% to about 40% (e.g., about 1% to about 5%, about 3% to about 10%, about 5% to about 15%, about 10% to about 20%, about 15% to about 30%, or about 20% to about 40%) by weight of the animal cells of the disclosure; optionally, about 0% to about 97% of one or more plant-based protein/product (e.g., about 10% to about 90%, about 40% to about 80%); about 0% to about 40% (e.g., about 15% to about 25%) by weight of an optional carbohydrate-based gel; about 0% to about 30% by weight of an optional animal fat (e.g., about 1% to about 5%, about 3% to about 10%, about 5% to about 15%, about 10% to about 20%, or about 15% to about 30%); about 0% to about 35% by weight of an optional non-animal fat (e.g., about 10% to about 15%); about 0% to about 10% by weight of an optional flavoring agent (e.g., about 0.00001% to about 5%); about 0% to about 15% (e.g., about 2% to about 15% or about 2% to about 10%) by weight of an optional binding agent; and about 0% to about 4% (e.g., about 0.05% to about 1%, or about 0.2% to about 2%) by weight of an optional iron complex such as a heme-containing protein and/or an iron salt.

In some embodiments, the hybrid meat substitute product comprises between 0.1-30% total fat (animal fat plus non-animal fat) by weight. In some embodiments, the hybrid meat substitute product comprises about 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, total fat by weight, including all ranges and subranges therebetween. In some embodiments, the hybrid meat substitute product comprises at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, total fat by weight, including all ranges and subranges in between. In some embodiments, the hybrid meat substitute product comprises no more than 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, total fat by weight, including all ranges and subranges in between. In some embodiments, the hybrid meat substitute product comprises between 0.1-0.5%, 0.5-1%, 1-2%, 2-3%, 3-4%, 4-5%, 5-6%, 6-7%, 7-8%, 8-9%, 9-10%, 10-12%, 12-15%, 15-20%, 20-25%, or 25-30%, total fat by weight, including all ranges and subranges in between. In some embodiments, the hybrid meat substitute product comprises between 0.1-1%, 0.5-2%, 1-3%, 2-4%, 3-5%, 4-6%, 5-7%, 6-8%, 7-9%, 8-10%, 9-12%, 10-15%, 12-20%, 15-25%, or 20-30%, total fat by weight, including all ranges and subranges in between. In some embodiments, the hybrid meat substitute product comprises between 0.1-2%, 0.5-3%, 1-4%, 2-5%, 3-6%, 4-7%, 5-8%, 6-9%, 7-10%, 8-12%, 9-15%, 10-20%, 12-25%, or 15-30%, total fat by weight, including all ranges and subranges in between. In some embodiments, the hybrid meat substitute product comprises between 5-10% total fat by weight. In some embodiments, the hybrid meat substitute product comprises between 4-6%, 3-7%, or 2-8%, total fat by weight, including all ranges and subranges in between. In some embodiments, the hybrid meat substitute product comprises between 9-11%, 8-12%, or 7-13%, total fat by weight, including all ranges and subranges in between.

In some embodiments, the hybrid meat substitute product comprises 30%-97% plant-based meat dough by weight. In some embodiments, the hybrid meat substitute product comprises 60%-97% plant-based meat dough by weight. In some embodiments, the hybrid meat substitute product comprises about 60%, 65%, 70%, 75%, 80%, 85%, 90%, or 95% plant-based meat dough by weight. In some embodiments, the hybrid meat substitute product comprises at least 30%, at least 40%, at least 50%, at least 60%, at least 65%, at least 70%, at least 75%, at least 80%, at least 85%, or at least 90%, plant-based meat dough by weight, including all ranges and subranges therebetween. In some embodiments, the hybrid meat substitute product comprises no more than 60%, no more than 65%, no more than 70%, no more than 75%, no more than 80%, no more than 85%, no more than 90%, or no more than 95% plant-based meat dough by weight, including all ranges and subranges therebetween. In some embodiments, the hybrid meat substitute product comprises 30-50%, 40-60%, 50-65%, 60-70%, 65-75%, 70-80%, 75-85%, 80-90%, 85-95%, 30-60%, 40-65%, 50-70%, 60-75%, 65-80%, 70-85%, 75-90%, 80-95%, 30-65%, 40-70%, 50-75%, 60-80%, 65-85%, 70-90%, 75-95%, 30-70%, 40-75%, 50-80%, 60-85%, 65-90%, 70-95%, 30-75%, 40-80%, 50-85%, 60-90%, or 65-95%, plant-based meat dough by weight, including all ranges and subranges therebetween.

Methods of Producing the Hybrid Meat Substitute Product

In one aspect, the present disclosure provides methods of producing the hybrid meat substitute products of the disclosure.

In some embodiments, the method comprises preparing the plant-based meat dough. In some embodiment, preparing the plant-based meat dough comprises mixing plant protein ingredients with binding agents. In some embodiments, the method comprises adding oil (e.g., plant-based oil) and mixing until homogeneously dispersed.

In some embodiments, the method comprises adding exogenous heme-containing protein to the plant-based meat dough.

In some embodiments, the method comprises adding animal cells to the plant-based meat dough. In some embodiments, the animal cells comprise the exogenous heme-containing protein.

In some embodiments, the method comprises adding animal fat to the plant-based meat dough. In some embodiments, the method comprises adding fat cells to the plant-based meat dough, wherein the fat cells comprise animal fat.

In some embodiments, the method comprises mixing the animal cells of the disclosure with one or more plant protein/product and an optional animal fat, an optional non-animal fat, an optional edible fibrous component, and an optional flavoring agent, and adding an aqueous component such as water or a broth to the mixture and kneading or otherwise mixing, manually or mechanically, to form a dough. The aqueous component can be heated before adding to the mixture of plant protein and fibrous component. Once the meat dough is formed, the meat dough can be heated (e.g., steamed or boiled, grilled, baked, etc.) to a temperature ranging from 150° F. to 250° F. (e.g., 160° F. to 240° F., 170° F. to 230° F., 180° F. to 220° F., or 190° F. to 212° F.). For example, a meat dough can be steamed by placing in a rice cooker, steam cabinet, or tunnel steamer. A meat dough can be heated by applying dry heat, for example, by placing in a bread maker or oven, or by immersing in hot water or broth. Boiling in broth can improve the meat dough flavor because beneficial flavors and off-flavor masking agents can be absorbed into the dough. Texture properties may also be modulated by choice of the cooking method.

In some embodiments, the method comprises processing of the animal cells.

In some embodiments, the animal cells of the hybrid meat substitute product have undergone one or more food processing steps selected from heating, refrigerating, and freezing. In some embodiments, the animal cells are processed as a raw, uncooked food ingredient, or as a cooked food ingredient. In some embodiments, the ingredient comprises animal cells that have been heated (e.g., cooked). In some embodiments, the food ingredient comprises animal cells that have undergone one or more food processing steps selected from baking, roasting, broiling, sautéing, braising, steaming, poaching, grilling, frying (e.g., deep-frying, pan-frying), impingement cooking, boiling, stewing, simmering, microwaving, and sous vide cooking. In some embodiments, the food ingredient comprising the animal cells has undergone one or more flavoring steps. Non-limiting examples of flavoring steps include smoking, marinating and glazing.

In some embodiments, the food processing step comprises exposing the animal cells to high temperatures (e.g., heating) that would not support the viability, survival, expansion and/or differentiation of the cells. In some embodiments, exposing the animal cells to temperatures comprises fully or partially cooking the animal cells, for example, by heating the animal cells to a temperature of about 100° F. to about 600° F., about 100° F. to about 550° F., about 100° F. to about 500° F., about 100° F. to about 450° F., about 100° F. to about 400° F., about 100° F. to about 350° F., about 100° F. to about 300° F., about 100° F. to about 250° F., about 100° F. to about 200° F. or about 100° F. to about 150° F., or by heating the cell population to a temperature of at least 100° F., at least 125° F., at least 150° F., at least 175° F., at least 200° F., at least 225° F., at least 250° F., at least 275° F., at least 300° F., at least 325° F., at least 350° F., at least 375° F., at least 400° F., at least 425° F., at least 450° F., at least 475° F., at least 500° F., at least 525° F., at least 550° F., at least 575° F., or at least 600° F., including all ranges and subranges therebetween. In some embodiments, the animal cells are exposed to high temperatures for at least 15 seconds, at least 30 seconds, at least 1 minute, at least 2 minutes, at least 3 minutes, at least 5 minutes, at least 10 minutes, at least 20 minutes, at least 30 minutes, or at least 60 minutes, including all ranges and subranges therebetween.

In some embodiments, the food processing step comprises exposing the animal cells to low temperatures that would not support the expansion and/or differentiation of the animal cells. Low temperatures include a temperature of about 15° C. (about 59° F.) or lower, about 10° C. (about 50° F.) or lower, about 0° C. to about 15° C. (about 32° F. to about 59° F.), about 0° C. to −15° C. (about 32° F. to about 5° F.), about −15° C. to about 15° C. (about 5° F. to about 59° F.), about 0° C. to −213° C. (about 32° F. to about −350° F.), about −30° C. to about −100° C. (about −22° F. to about −148° F.), about −50° C. to about −90° C. (about −58° F. to about −130° F.), or about −170° C. to about −190° C. (about −274° F. to about −310° F.), including all ranges and subranges therebetween.

In some embodiments, the animal cells are cooled to a temperature of about 2° C. to about 8° C. (about 35° F. to about 46.5° F.). In some embodiments, the animal cells are frozen, for example, by cooling to a temperature of about 32° F. or lower, e.g. about 32° F. to about 0° F., about 32° F. to about −10° F., about 32° F. to about −20° F., about 32° F. to about −30° F., about 32° F. to about −40° F., about 32° F. to about −50° F., about 32° F. to about −60° F., about 32° F. to about −70° F., about 32° F. to about −80° F., and the like. In some embodiments, the animal cells are exposed to low temperatures as low as about −300° F. to about −350° F., such as the liquid nitrogen temperature of about −321° F.

FURTHER NUMBERED EMBODIMENTS

Further numbered embodiments of the present disclosure are provided as follows:

Embodiment 1. A hybrid meat substitute product comprising:
a) a plant-based meat dough;
b) animal cells; and
c) exogenous heme-containing protein.

Embodiment 2. The hybrid meat substitute product of Embodiment 1, comprising at least 0.75% heme-containing protein by weight, and at least 2.5% animal cells by weight, wherein the animal cells are cultured animal cells.

Embodiment 3. The hybrid meat substitute product of Embodiment 1 or 2, comprising:
d) animal fat.

Embodiment 4. The hybrid meat substitute product of any one of Embodiments 1-3, wherein the hybrid meat substitute product does not comprise methylcellulose or its derivative.

Embodiment 5. The hybrid meat substitute product of any one of Embodiments 1-4, wherein the animal cells comprise, or are derived from, skeletal muscle cells, myoblasts, myogenic cells, fibroblasts, mesenchymal stem cells, endothelial cells, adipose progenitor cells, preadipocytes, or cardiomyocytes.

Embodiment 6. The hybrid meat substitute product of any one of Embodiments 1-5, wherein the animal cells are not hepatocytes.

Embodiment 7. The hybrid meat substitute product of any one of Embodiments 1-6, wherein the animal cells are myoblasts.

Embodiment 8. The hybrid meat substitute product of any one of Embodiments 1-7, wherein the animal cells are substantially undifferentiated cultivated myoblast cells.

Embodiment 9. The hybrid meat substitute product of any one of Embodiments 1-8, wherein at least 90%, 80%, 70%, 60% of the animal cells do not exhibit muscle fibers or myotubes.

Embodiment 10. The hybrid meat substitute product of any one of Embodiments 1-9, wherein the animal cells are cultivated cells.

Embodiment 11. The hybrid meat substitute product of any one of Embodiments 1-10, wherein the animal cells are suspension culture cells (i.e., wherein more than 90%, 80%, 70%, or 60% of the animal cells not adhered to any growth substrate).

Embodiment 12. The hybrid meat substitute product of any one of Embodiments 1-11, wherein the animal cells are not in a meat structure.

Embodiment 13. The hybrid meat substitute product of any one of Embodiments 1-12, wherein the animal cells do not comprise any connective tissue and/or a blood vessel.

Embodiment 14. The hybrid meat substitute product of any one of Embodiments 1-13, comprising between 0.1-40% animal cells by weight.

Embodiment 15. The hybrid meat substitute product of any one of Embodiments 1-14, comprising at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, or 39%, animal cells by weight, including all ranges and subranges in between.

Embodiment 16. The hybrid meat substitute product of any one of Embodiments 1-14, comprising at least 2.5% animal cells by weight, including all ranges and subranges in between.

Embodiment 17. The hybrid meat substitute product of any one of Embodiments 1-16, comprising no more than 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, or 39%, animal cells by weight, including all ranges and subranges in between.

Embodiment 18. The hybrid meat substitute product of any one of Embodiments 1-17, comprising between 2-10% animal cells by weight.

Embodiment 19. The hybrid meat substitute product of any one of Embodiments 1-17, comprising no more than 20% animal cells by weight.

Embodiment 20. The hybrid meat substitute product of any one of Embodiments 1-19, comprising between 0.1-10% exogenous heme-containing protein by weight.

Embodiment 21. The hybrid meat substitute product of any one of Embodiments 1-20, comprising at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% exogenous heme-containing protein by weight, including all ranges and subranges in between.

Embodiment 22. The hybrid meat substitute product of any one of Embodiments 1-21, comprising at least 0.25% exogenous heme-containing protein by weight.

Embodiment 23. The hybrid meat substitute product of any one of Embodiments 1-22, comprising no more than 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% exogenous heme-containing protein by weight, including all ranges and subranges in between.

Embodiment 24. The hybrid meat substitute product of any one of Embodiments 1-23, comprising between 0.1-10% total heme-containing protein by weight.

Embodiment 25. The hybrid meat substitute product of any one of Embodiments 1-24, comprising at least 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% total heme-containing protein by weight, including all ranges and subranges in between.

Embodiment 26. The hybrid meat substitute product of any one of Embodiments 1-25, comprising at least 0.25% total heme-containing protein by weight.

Embodiment 27. The hybrid meat substitute product of any one of Embodiments 1-26, comprising no more than 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.2%, 2.5%, 3%, 3.5%, 4%, 4.5%, 5%, 5.5%, 6%, 6.5%, 7%, 7.5%, 8%, 8.5%, 9%, or 9.5% total heme-containing protein by weight, including all ranges and subranges in between.

Embodiment 28. The hybrid meat substitute product of any one of Embodiments 1-27, comprising between 0.5-2% exogenous heme-containing protein by weight.

Embodiment 28.1. The hybrid meat substitute product of any one of Embodiments 1-27, comprising between 0.5-2.5% exogenous heme-containing protein by weight.

Embodiment 28.2. The hybrid meat substitute product of any one of Embodiments 1-27, comprising between 0.5-1.0% exogenous heme-containing protein by weight.

Embodiment 29. The hybrid meat substitute product of any one of Embodiments 1-28.2, comprising at least 0.5% exogenous heme-containing protein by weight.

Embodiment 30. The hybrid meat substitute product of any one of Embodiments 1-29, comprising animal cells and exogenous heme-containing protein at an amount according to one of the combinations listed in Table 1A.

Embodiment 31. The hybrid meat substitute product of any one of Embodiments 1-30, comprising between 0.5-1.6% total heme-containing protein by weight.

Embodiment 31.1. The hybrid meat substitute product of any one of Embodiments 1-30, comprising between 0.5-3% total heme-containing protein by weight.

Embodiment 31.2. The hybrid meat substitute product of any one of Embodiments 1-30, comprising between 0.5-2.5% total heme-containing protein by weight.

Embodiment 31.3. The hybrid meat substitute product of any one of Embodiments 1-30, comprising between 0.5-1.0% total heme-containing protein by weight.

Embodiment 32. The hybrid meat substitute product of any one of Embodiments 1-31.3, comprising at least 0.6% total heme-containing protein by weight.

Embodiment 33. The hybrid meat substitute product of any one of Embodiments 1-32, comprising animal cells and total heme-containing protein at an amount according to one of the combinations listed in Table 1B.

Embodiment 34. The hybrid meat substitute product of any one of Embodiments 1-33, wherein the exogenous heme-containing protein is selected from the group consisting of a non-symbiotic hemoglobin, a Hell's gate globin I, a flavohemoprotein, a leghemoglobin, a heme-dependent peroxidase, a cytochrome c peroxidase, a mammalian myoglobin, an androglobin, a cytoglobin, a globin E, a globin X, a globin Y, a hemoglobin, a myoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin, a truncated 2/2 globin, a hemoglobin 3, a cytochrome, and a peroxidase.

Embodiment 35. The hybrid meat substitute product of any one of Embodiments 1-34, wherein the exogenous heme-containing protein is a myoglobin.

Embodiment 36. The hybrid meat substitute product of Embodiment 35, wherein at least 30%, 40%, 50%, 60%, 70%, 80%, or 90% of the myoglobin is oxymyoglobin.

Embodiment 37. The hybrid meat substitute product of Embodiment 35, wherein at least 30%, 40%, 50%, 60%, 70%, 80%, or 90% of the myoglobin is deoxymyoglobin.

Embodiment 38. The hybrid meat substitute product of Embodiment 35, wherein at least 30%, 40%, 50%, 60%, 70%, 80%, or 90% of the myoglobin is metmyoglobin.

Embodiment 39. The hybrid meat substitute product of any one of Embodiments 1-38, wherein the heme-containing protein is bovine myoglobin, wherein the bovine myoglobin comprises an amino acid sequence having at least 80%, 85%, 90%, or 95% identity to SEQ ID NO: 1.

Embodiment 40. The hybrid meat substitute product of any one of Embodiments 1-39, comprising between 0.0003-0.03% by weight of iron (Fe) bound to the (exogenous or total) heme-containing protein.

Embodiment 41. The hybrid meat substitute product of any one of Embodiments 1-40, comprising at least 0.0003%, 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, or 0.026%, by weight of iron (Fe) bound to the (exogenous or total) heme-containing protein.

Embodiment 42. The hybrid meat substitute product of any one of Embodiments 1-41, comprising at least 0.00075% by weight of iron (Fe) bound to the (exogenous or total) heme-containing protein.

Embodiment 43. The hybrid meat substitute product of any one of Embodiments 1-41, comprising at least 0.0015% by weight of iron (Fe) bound to the (exogenous or total) heme-containing protein.

Embodiment 44. The hybrid meat substitute product of any one of Embodiments 1-43, comprising no more than 0.0004%, 0.0005%, 0.0006%, 0.0007%, 0.0008%, 0.0009%, 0.001%, 0.0012%, 0.0014%, 0.0016%, 0.0018%, 0.002%, 0.0023%, 0.0026%, 0.003%, 0.0035%, 0.004%, 0.0045%, 0.005%, 0.006%, 0.007%, 0.008%, 0.009%, 0.01%, 0.012%, 0.014%, 0.016%, 0.018%, 0.02%, 0.023%, 0.026%, or 0.03% by weight of iron (Fe) bound to the (exogenous or total) heme-containing protein.

Embodiment 45. The hybrid meat substitute product of any one of Embodiments 1-44, comprising between 0.0015-0.006% by weight of iron (Fe) bound to the (exogenous or total) heme-containing protein.

Embodiment 46. The hybrid meat substitute product of any one of Embodiments 3-45, wherein the animal fat is from cultivated cells.

Embodiment 47. The hybrid meat substitute product of any one of Embodiments 3-46, wherein the animal fat is from cultivated adipocytes.

Embodiment 48. The hybrid meat substitute product of any one of Embodiments 3-47, comprising between 0.1-30% animal fat by weight.

Embodiment 49. The hybrid meat substitute product of any one of Embodiments 3-48, comprising between 5-30% animal fat by weight.

Embodiment 50. The hybrid meat substitute product of any one of Embodiments 1-49, comprising between 10-20% total fat by weight.

Embodiment 51. The hybrid meat substitute product of any one of Embodiments 1-50, comprising at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, animal fat by weight, including all ranges and subranges in between.

Embodiment 52. The hybrid meat substitute product of any one of Embodiments 1-50, comprising at least 2.5% animal fat by weight.

Embodiment 53. The hybrid meat substitute product of any one of Embodiments 1-52, comprising no more than 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, animal fat by weight, including all ranges and subranges in between.

Embodiment 54. The hybrid meat substitute product of any one of Embodiments 1-53, comprising at least 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, total fat by weight, including all ranges and subranges in between.

Embodiment 55. The hybrid meat substitute product of any one of Embodiments 1-54, comprising no more than 0.1%, 0.2%, 0.5%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, or 29%, total fat by weight, including all ranges and subranges in between.

Embodiment 56. The hybrid meat substitute product of any one of Embodiments 1-55, comprising animal fat and exogenous heme-containing protein at an amount according to one of the combinations listed in Table 2A.

Embodiment 57. The hybrid meat substitute product of any one of Embodiments 1-56, comprising animal fat and total heme-containing protein at an amount according to one of the combinations listed in Table 2B.

Embodiment 58. The hybrid meat substitute product of any one of Embodiments 1-57, wherein at least a portion of the exogenous heme-containing protein is comprised within the animal cells.

Embodiment 59. The hybrid meat substitute product of any one of Embodiments 1-58, wherein less than 10%, 20%, 30%, 40%, 50%, or 60% of the (relative) exogenous heme-containing protein in the hybrid meat substitute product is comprised within the animal cells.

Embodiment 60. The hybrid meat substitute product of any one of Embodiments 1-59, wherein the exogenous heme-containing protein is provided as an cell-free or substantially cell-free ingredient.

Embodiment 61. The hybrid meat substitute product of any one of Embodiments 1-60, wherein the animal cells are bovine cells, porcine cells, ovine cells, chicken cells, turkey cells, or cells from an aquatic animal species.

Embodiment 62. The hybrid meat substitute product of any one of Embodiments 3-61, wherein the animal fat is from a bovine, porcine, or ovine source.

Embodiment 63. The hybrid meat substitute product of any one of Embodiments 1-62, wherein the hybrid meat substitute product does not comprise any binding agent selected from methylcellulose, hydroxypropylmethyl cellulose, guar gum, locust bean gum, xanthan gum, agar, pectin, carrageenan, konjac, alginate, agarose, starch (native or modified), flours, and derivatives thereof.

Embodiment 64. The hybrid meat substitute product of any one of Embodiments 1-62, wherein the hybrid meat substitute product does not comprise any binding agent.

Embodiment 65. A hybrid meat substitute product comprising:
a) 60%-97% plant-based meat dough by weight;
b) 1%-10% cultivated animal cells by weight;
c) 1%-10% exogenous heme-containing protein by weight;
d) 1%-25% animal fat by weight;
wherein the animal cells have not differentiated into muscle fibers and wherein the cultivated animal cells are from a cow.

Embodiment 66. A hybrid meat substitute product comprising:
a) 60%-97% plant-based meat dough by weight;
b) 1%-10% cultivated animal cells by weight;
c) 1%-10% total heme-containing protein by weight;
d) 1%-25% animal fat by weight;
wherein the animal cells have not differentiated into muscle fibers and wherein the cultivated animal cells are from a cow.

Embodiment 67. The hybrid meat substitute product of any one of Embodiments 1-66, wherein at least 20%, at least 30%, at least 40%, at least 50%, at least 60%, at least 70%, at least 80%, at least 90%, at least 95%, at least 98%, at least 99%, or 100%, of the animal cells are myoblasts.

Embodiment 68. The hybrid meat substitute product of Embodiments 67, wherein at least 70% of the animal cells are myoblast.

Embodiment 69. The hybrid meat substitute product of any one of Embodiments 1-68, wherein at least 20%, at least 30%, at least 40%, at least 50%, at least 60%, at least 70%, at least 80%, at least 90%, at least 95%, at least 98%, at least 99%, or 100%, of the animal cells are fibroblasts.

Embodiment 70. The hybrid meat substitute product of Embodiments 69, wherein at least 70% of the animal cells are fibroblast.

Embodiment 71. The hybrid meat substitute product of any one of Embodiments 1-70, wherein the animal cells are not adhered to any growth substrate.

Embodiment 72. The hybrid meat substitute product of any one of Embodiments 1-71, wherein the animal cells are not hepatocytes.

Embodiment 73. The hybrid meat substitute product of any one of Embodiments 1-72, wherein the hybrid meat substitute product mimics ground meat.

Embodiment 74. The hybrid meat substitute product of any one of Embodiments 1-73, wherein the hybrid meat substitute product is shaped like a burger patty.

Embodiment 75. The hybrid meat substitute product of any one of Embodiments 1-74. wherein the hybrid meat substitute product does not have any methylcellulose.

Embodiment 76. A consumer food item selected from the group consisting of: a burger, a meatball, a chili, a shepherd's pie, pizza, taco lasagna, sloppy joe, stroganoff, and meatloaf, wherein said consumer food comprises the hybrid substitute meat product of any one of Embodiments 1-75 or a cooked product thereof.

Embodiment 77. A cooked food product prepared by cooking a food item comprising the hybrid substitute meat product of any one of Embodiments 1-75.

Embodiment 78. A method of producing the hybrid substitute meat product of any one of Embodiments 1-75, comprising mixing the animal cells with plant-based ingredient(s).

Embodiment 79. The method of Embodiment 78, further comprising mixing the exogenous heme-containing protein with the animal cells and the plant-based ingredient(s), wherein the exogenous heme-containing protein is provided as an isolated ingredient.

Embodiment 80. The method of Embodiment 78 or 79, further comprising mixing the animal fat with the animal cells and the plant-based ingredient(s).

EXAMPLES

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 1: Incorporation of Animal Muscle Cells and Animal Fat into Plant-Based Burger Patty Results in Improved Sensory Profile An initial set of experiments were designed to test whether incorporating animal muscle cells or animal fat would improve the sensory profile of a plant-based burger patty.

Four different formulas were tested, each containing 5-10% (w/w) animal muscle cells, and 5-10% (w/w) animal fat within a plant-based burger matrix. The plant-based meat dough was prepared as follows:
1. Mix water, seasoning ingredients and other texture ingredients.
2. Add plant protein ingredients (e.g., plant protein ingredients derived from pea, soy and gluten) and animal cells and mix.
3. Add emulsion phase and binding ingredients (e.g., methylcellulose or its emulsion); mix until homogenously dispersed.
4. Add oil phase (e.g., plant-based oil) and animal fat; mix until homogenously dispersed.
5. Reduce particle size (e.g., using grinding techniques) of the cooled mixture.
6. Cover and freeze for storage.

The experimental design of these patties is provided in Table 3 below:

TABLE 3

| Ingredients Group | Percentage (w/w) | | | |
| --- | --- | --- | --- | --- |
| | 5% Muscle 5% Fat | 10% Muscle 5% Fat | 5% Muscle 10% Fat | 10% Muscle 10% Fat |
| Animal Muscle Cells | 5% | 10% | 5% | 10% |
| Animal fat | 5% | 5% | 10% | 10% |
| Plant-Based Meat Dough | 90% | 85% | 85% | 80% |

The trial burger patties were thawed under refrigerated conditions (4° C.) and were then cooked on a skillet until they reached an internal temperature of 165 F. Patties were served alone, without any buns, burger trimmings, or any condiments or dressing to ensure that feedback was not influenced by other factors. Tasters were asked a series of questions about their experience, and were asked to provide descriptive notes. A summary of the results of this experiment are provided in Table 4 below:

TABLE 4

| | 5% Animal Cells | 10% Animal Cells |
| --- | --- | --- |
| 5% Animal Fat | Generally preferred. Has a smoky/bacon flavor and a juicy mouthfeel. | More neutral flavor, but dryer and more coarse. |
| 10% Animal Fat | Generally preferred. Tasted juicier with a noticeable "saturated fat" mouthfeel. Balanced flavor. | More neutral flavor, tasted juicy, but more coarse and has a less favorable texture. |

Test patties comprising 5% (w/w) animal muscle cells were generally preferred, whereas feedback for formulas comprising 10% (w/w) animal muscle cells indicated coarse texture. In this example, the animal muscle cells were derived from shredded harvested beef. Overall, the formula with 5% (w/w) final concentration of both animal muscle cells and animal fat is considered to be the most appropriate starting point for testing the effect of the combination of animal muscle cells/fat with additional myoglobin in a plant-based burger patty.

Example 2: Incorporation of Exogenous Myoglobin into Plant-Based Burger Patty Results in Improvement of Visual Appeal Factors in Dose-Dependent Manner In a second set of experiments, up to 0.75% final concentration (w/w) of bovine myoglobin was added to otherwise identical plant-based burger patties to test whether incorporation of myoglobin would improve the color and sensory profile of the burger patty to gain more consumer acceptance and to more closely replicate the experience of a beef patty. No commercial source of food-safe exogenous myoglobin was available at the time that this experiment was conducted. Therefore myoglobin used in this example was purified by a commercial lab from harvested meat.

The following protocol was used to prepare the plant-base/myoglobin hybrid burger patty:
1. Mix water, seasoning ingredients and other texture ingredients.
2. Add plant protein ingredients (e.g., plant protein ingredients derived from pea, soy and gluten) and mix.
3. Add emulsion phase and binding ingredients (e.g., methylcellulose or its emulsion) and myoglobin; mix until homogeneously dispersed.
4. Add oil phase (e.g., plant-based oil); mix until homogeneously dispersed.
5. Reduce particle size (e.g., using grinding techniques) of the cooled mixture.
6. Cover and freeze for storage at −3° F.

This set of experiments tested the color and sensory profile of three otherwise identical plant-based patties with only varying final concentrations of myoglobin ranging from 0.25%, 0.50%, or 0.75%, without adding any animal muscle cells or animal fat. The formula of these patties (excluding plant-based meat dough and 100% beef controls) is provided in Table 5 below:

TABLE 5

| Ingredients | Percentage (w/w) | | |
| --- | --- | --- | --- |
| Group | 0.25% Myoglobin | 0.5% Myoglobin | 0.75% Myoglobin |
| Myoglobin | 0.25% | 0.50% | 0.75% |
| Plant-Based Meat Dough | 99.75% | 99.5% | 99.25% |

Figure 1B:
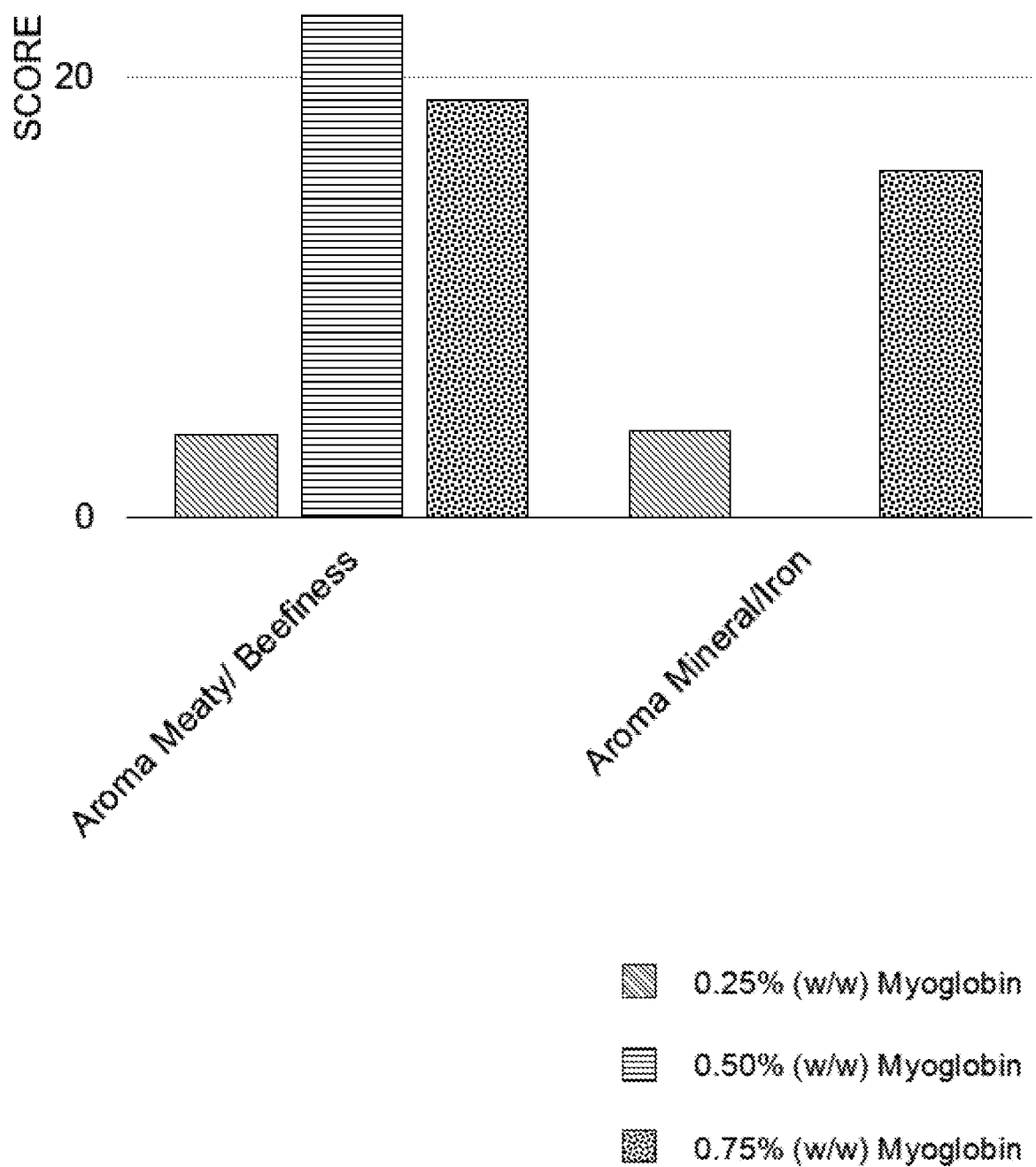
Figure 1C:
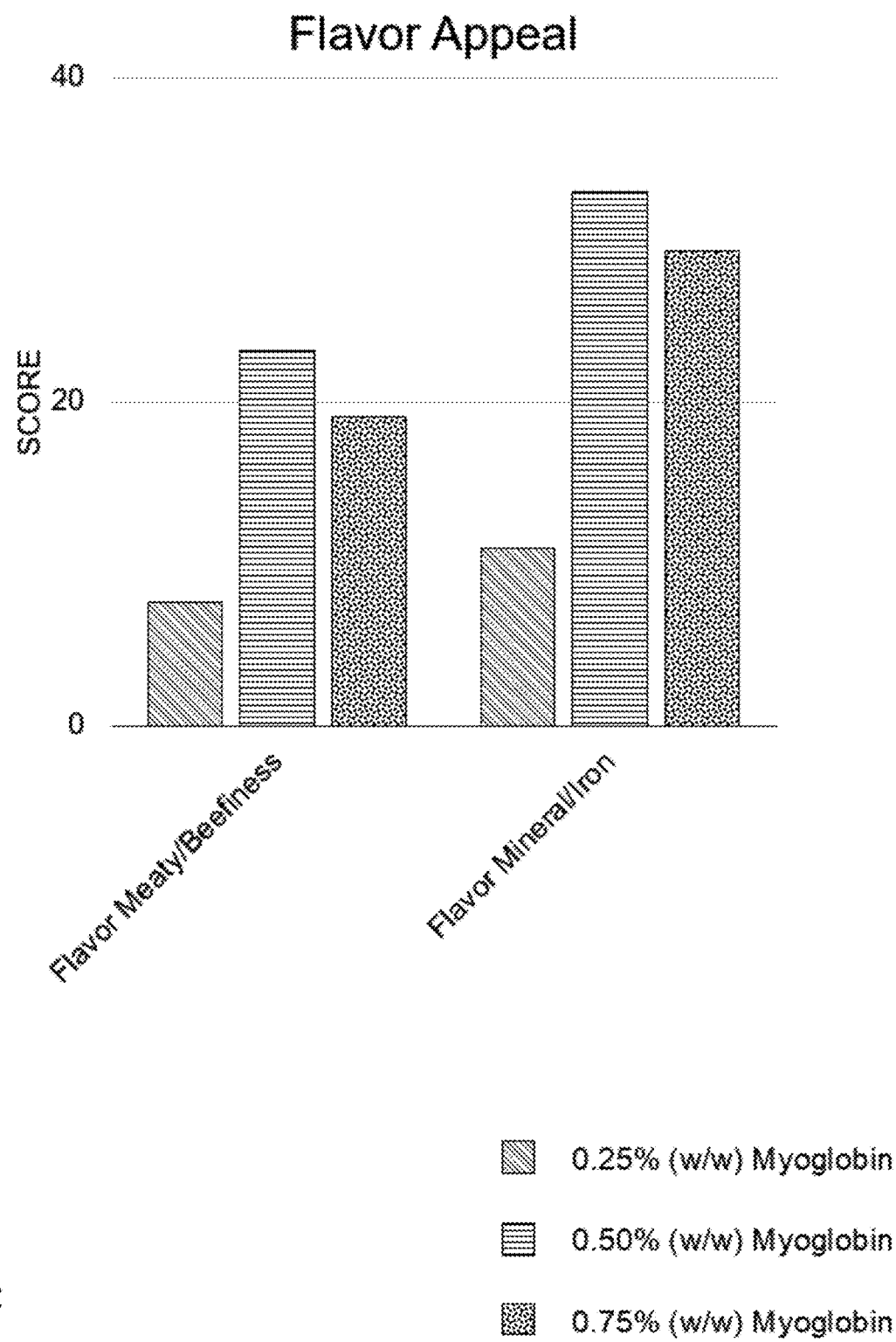

The trial burger patties were thawed under refrigerated conditions (4° C.) and were then cooked on a skillet until they reached an internal temperature of 165° F. Patties were served alone, without any buns, burger trimmings, or any condiments or dressing to ensure that feedback was not influenced by other factors. Each formula was compared to two controls in a taste test: 1) a beef burger patty composed of CreamCo 100% beef shoulder clod (chuck), natural, corn finish; and 2) the same plant-based patty formula without myoglobin. Multiple participants used a scoring system to evaluate the color and sensory profile of each formula (FIGS. 1A-1C). The results from this experiment are presented in a 0-100 scoring system, in which a score of 100 means that the specific feature was indistinguishable from that of the control beef patty for all trial participants, and a score of 0 means that the specific feature is indistinguishable from that of the control plant-based patty without any myoglobin for all trial participants. The higher the score is, the closer it is to the corresponding feature of the beef patty.

As shown in FIG. 1A, incorporating 0.25-0.75% (w/w) final concentration of myoglobin results in dose-dependent improvements of visual appeal factors, including raw color intensity, cooked color intensity and of color and sensory profile of the patty. The extent of improvement generally correlates with the concentration of incorporated myoglobin.

Test patties with myoglobin also exhibited dose-dependent increases in olfactory appeal factors such as meaty/beefiness smell and mineral/iron smells. (See FIG. 1B). Test patties with 0.25% and 0.5% (w/w) myoglobin also exhibited dose-dependent increases in flavor appeal factors of meaty/beefiness flavor and mineral/iron flavor. (See FIG. 1C) These increases in flavor appeal however, appeared to plateau and even diminish at higher concentrations of 0.75% (w/w) myoglobin in this experiment, suggesting potential limitations of myoglobin as a flavor enhancer.

Example 3: Higher Concentrations of Exogenous Myoglobin Improve Visual and Olfactory Appeal Factors of Plant-Based Burger Dough, but Exhibit a Plateau in Flavor Appeal Improvements Additional experiments with higher concentrations of myoglobin were conducted to evaluate whether further increases in myoglobin concentration would continue to improve the color and sensory profile of the patty. Following the protocol above for Example 2, burger patties were generated with three different trial concentrations (1%, 1.35%, and 1.7% (w/w)) of bovine myoglobin within otherwise identical plant-based burger meat doughs. The myoglobin in this experiment was extracted from harvested meat, as described in Example 2, above. The experimental design of these patties (excluding plant-based matrix and 100% beef controls) is provided in Table 6 below:

TABLE 6

| Ingredients | Percentage (w/w) | | |
| --- | --- | --- | --- |
| Group | 1% Myoglobin | 1.35% Myoglobin | 1.7% Myoglobin |
| Myoglobin | 1.00% | 1.35% | 1.70% |
| Plant-Based Meat Dough | 99.00% | 98.65% | 98.30% |

The trial burger patties were defrosted at refrigerated temperature and were then cooked on a skillet until they reached an internal temperature of 165° F. Patties were served alone, without any buns, burger trimmings, or any condiments or dressing to ensure that feedback was not influenced by other factors.

Figure 2A:
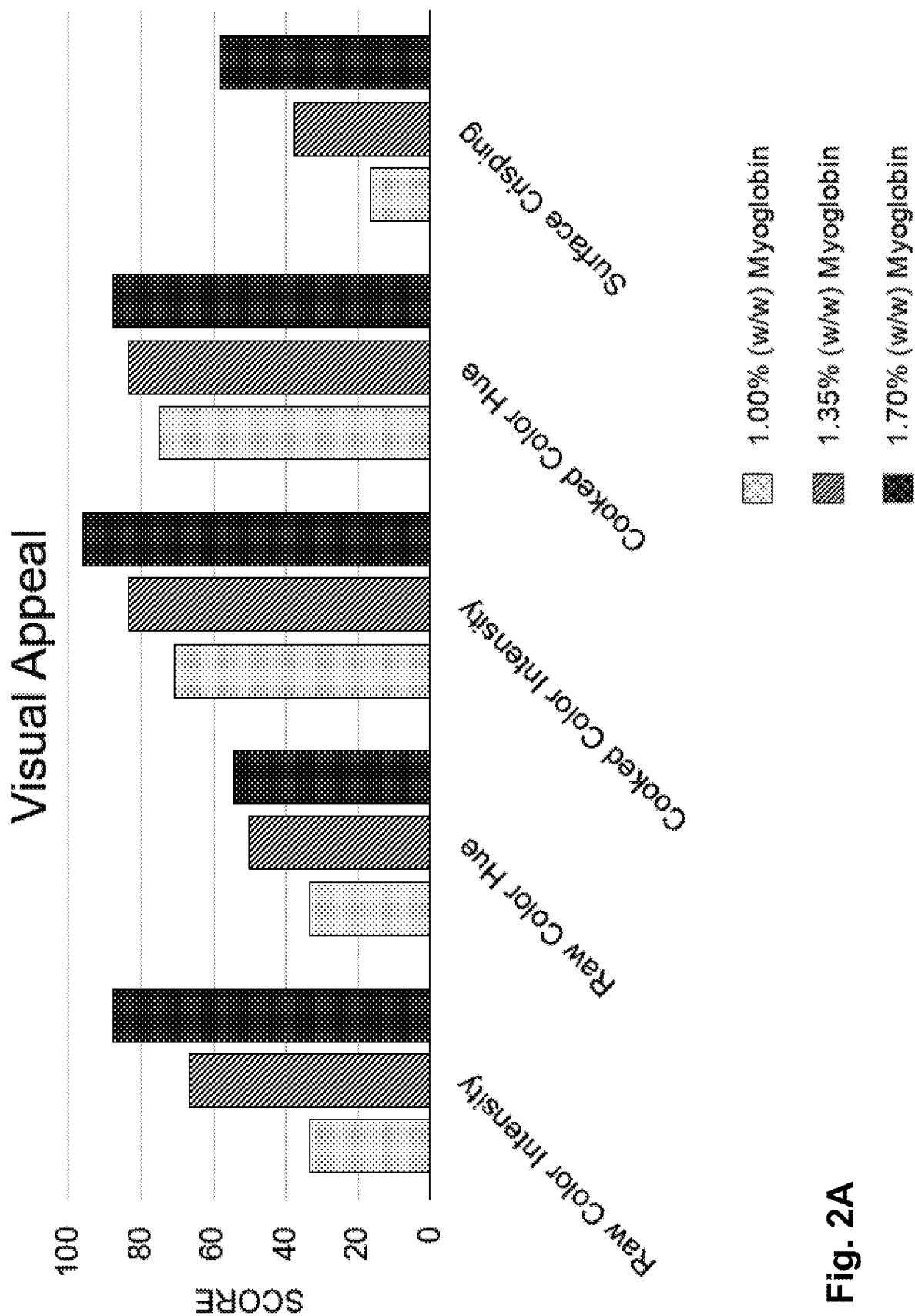
FIG. 2A-C shows the results of a consumer preference test of meat substitute products.
Figure 2B:
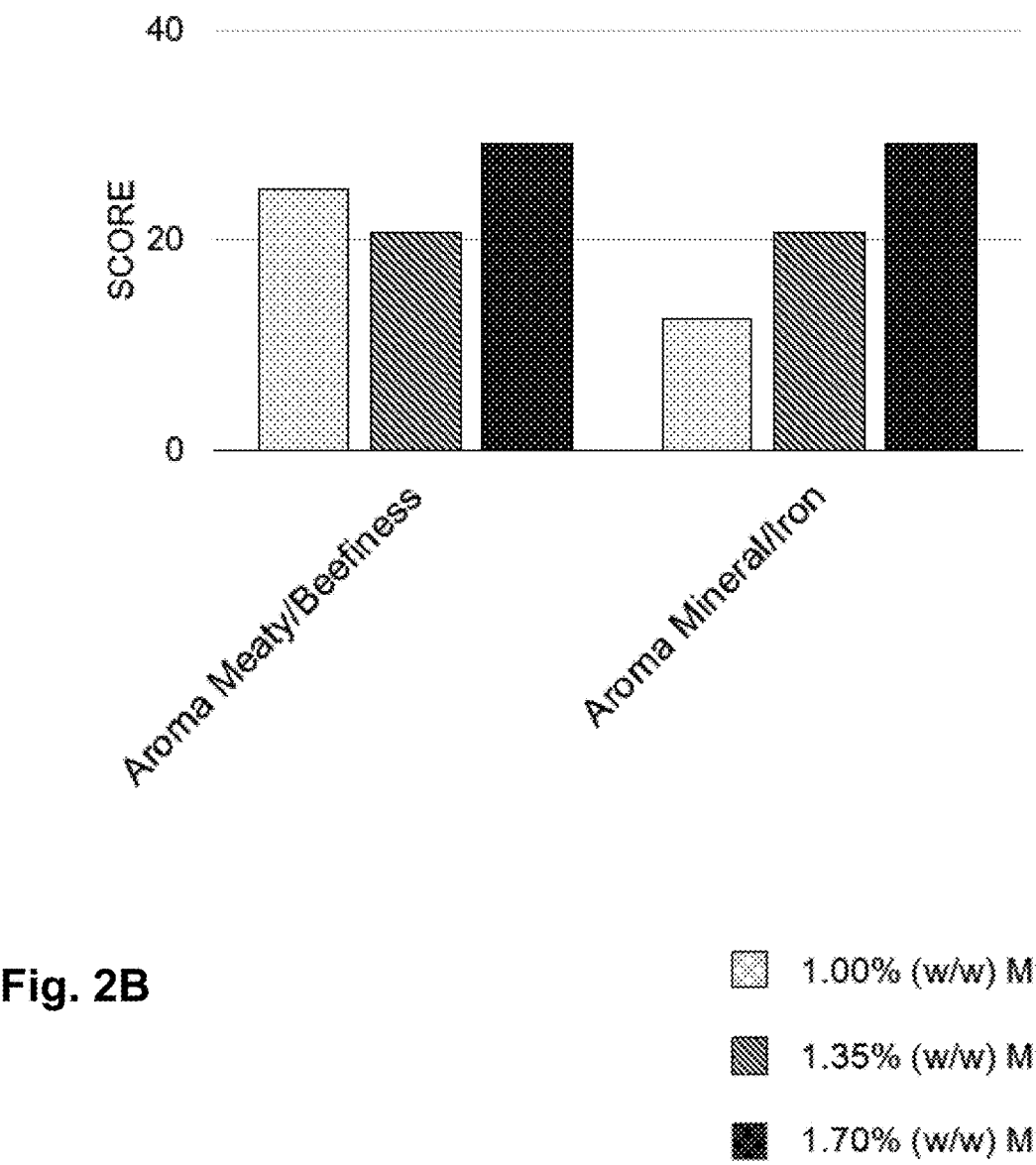
Figure 2C:
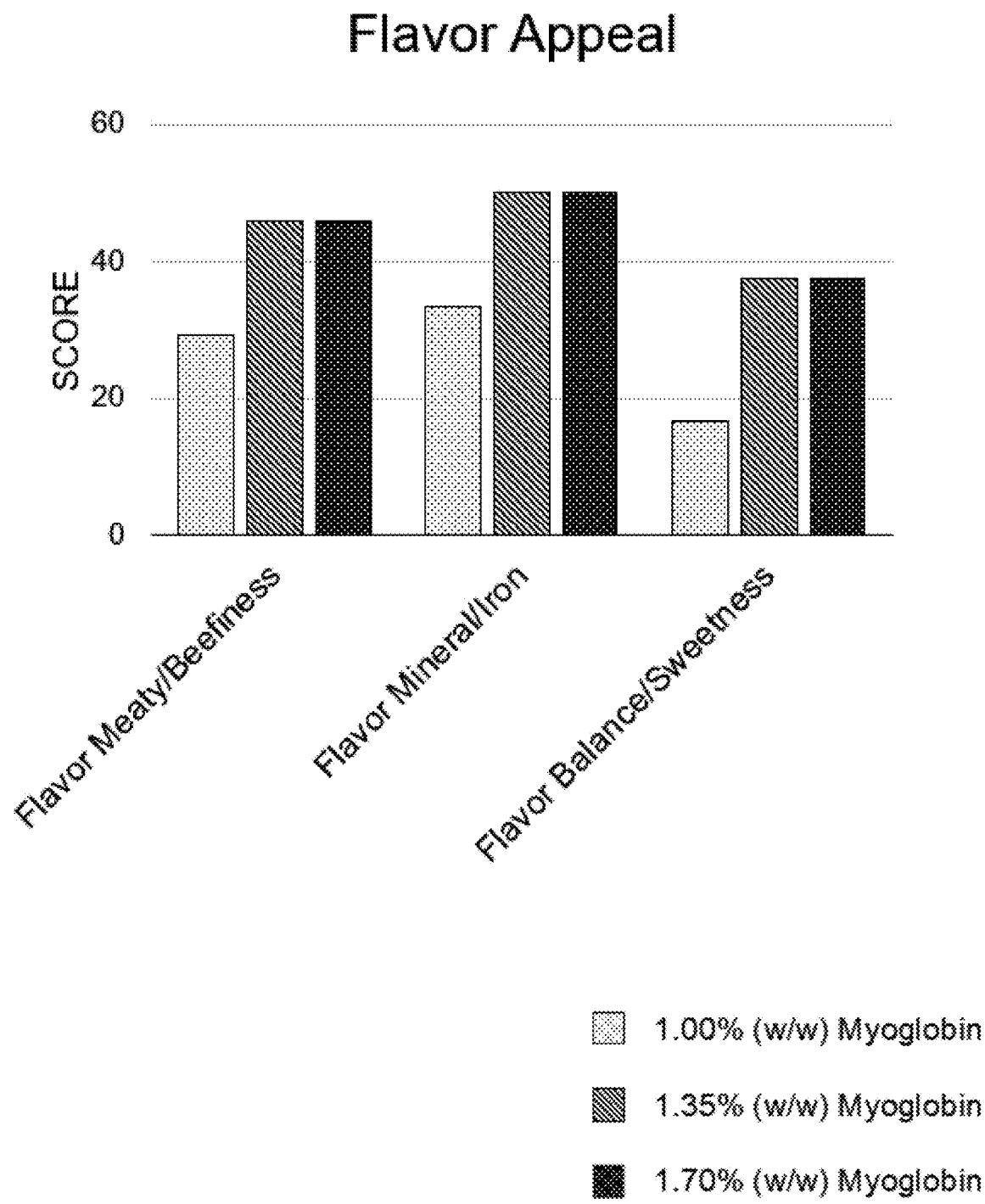

Similar to the experiments of Example 2, each myoglobin-containing plant-based patty formula was compared to two controls: 1) a beef burger patty composed of CreamCo 100% beef shoulder clod (chuck), natural, corn finish; and 2) the same plant-based patty formula without myoglobin, using a scoring system to evaluate the visual, olfactory and flavor appeal of the patties (FIGS. 2A-2C).

The results from this experiment are presented in a 0-100 scoring system, in which a score of 100 means that the specific feature is indistinguishable from that of the control beef patty for all trial participants, and a score of 0 means that the specific feature is indistinguishable from that of the control plant-based patty without any myoglobin for all trial participants. The higher the score is, the closer it is to the corresponding feature of the beef patty.

As shown in FIG. 2A, increasing the concentration of myoglobin above 1% results in further improvements of the color and surface crisping. The improvements to visual appeal factors exhibit dose-dependent response with myoglobin content, with the highest scores reported for the 1.70% myoglobin content.

Olfactory appeal factors of meaty/beefiness aroma and mineral/iron aroma also exhibit dose dependent increases. (See FIG. 2B) But the marginal score increases past 1.0% myoglobin are significantly smaller than visual appeal gains.

The results for flavor appeal factors produced different results. In accordance with the results of Example 2, 1.0% myoglobin content patties exhibited increases in savory/meaty flavor, mineral/iron flavor, and flavor balance/sweetness over the control plant based patty alone. (See FIG. 2C). Flavor improvements however were not dose-dependent at these higher ranges, showing a clear score plateau after 1.35% myoglobin content. These results suggest that myoglobin's ability to mimic beef burger flavor is dose-limited when applied alone. The flavor plateau in this experiment was similar to that of Example 2, except that it shifted to a slightly higher myoglobin concentration. This shift could be due to general experimental variability, such as variability between consumer feedback groups. Another potential explanation is that the harvested myoglobin, which had been purified and stored since the experiment in Example 2 began to degrade, thereby causing the shift. A new source of commercial myoglobin was identified for further experiments, to permit analysis with fresh ingredient batches. This new source of myoglobin, however, was not implemented until after Example 4 was completed, to allow for direct comparison between the results of Example 3 and 4. Further studies into myoglobin's effect on flavor with other ingredients is provided below.

Example 4: Combination of Exogenous Myoglobin with Animal Muscle Cells and Animal Fat Unexpectedly and Significantly Improves Color and Sensory Profile of Plant-Based Patty An experiment was designed to test whether exogenous myoglobin could improve the sensory profile of burger patties that already contained myoglobin in the form of animal muscle cells. Test patties containing various combinations of 5% (w/w) animal muscle cells, 5% (w/w) animal fat, and 1.55% (w/w) of exogenous bovine myoglobin within a plant-based patty matrix were tested. As with earlier examples, animal muscle cells were sourced from harvested beef for convenience, but the inventions disclosed herein can also use non-harvested animal cells, such as cultivated cells.

The experiment was replicated with two plant-based meat doughs. The first, plant-based meat dough was the same as Examples 2-3 with the exception that patties containing added animal fat had their plant-based fat content (i.e. plant oil, as described above) reduced so as to maintain equal total fat contents throughout all test patties. The second plant-based meat dough followed the recipe and plant-based fat reduction schemes as above, but also had a small amount of flavoring spices added. The different formulas (excluding plant-based meat dough and 100% beef controls) of this example are outlined in Table 7 below:

TABLE 7

| Ingredients Group | Percentage (w/w) | | | |
| --- | --- | --- | --- | --- |
| | no Myoglobin no Flavoring Agent | +Myoglobin no Flavoring Agent A | no Myoglobin + Flavoring Agent | +Myoglobin + Flavoring Agent |
| Myoglobin | 0.00% | 1.55% | 0.00% | 1.55% |
| Animal Muscle cells | 5.0% | 5.0% | 5.0% | 5.0% |
| Animal Fat | 5.0% | 5.0% | 5.0% | 5.0% |
| Flavoring Agent | 0.0% | 0.0% | 3.0% | 3.0% |
| Plant-Based Meat Dough (Fat adjusted) | 90.00% | 88.45% | 87.00% | 85.45% |

The trial burger patties were defrosted at refrigerated temperature and were then cooked on a skillet until they reached an internal temperature of 165 F. Patties were served alone, without any buns, burger trimmings, or any condiments or dressing to ensure that feedback was not influenced by other factors.

Similar to the experiments of Examples 2-3, each tested patty formula was compared to two controls: 1) the beef patty as described above, and 2) the same plant-based patty used to formulate the test patties, but lacking any of the added myoglobin/animal muscle cells/animal fat. Two plant based patty controls were used to appropriately control for test patties formulated with and without the additional flavoring agent. The test patty formulas containing the flavoring agent were compared with a plant-based patty control that also included the flavoring agent, whereas the test patty formulas without the flavoring agent were compared with a plant-based patty control without the flavoring agent.

Persons having skill in the art will recognize that patties containing animal muscle cells contained higher basal myoglobin contents compared to purely plant-based control patties. Applicant estimates, based on the myoglobin content of the animal muscle cells, that the 5% animal muscle cells imparted about 0.06% basal myoglobin content to all test patties.

Figure 8A:
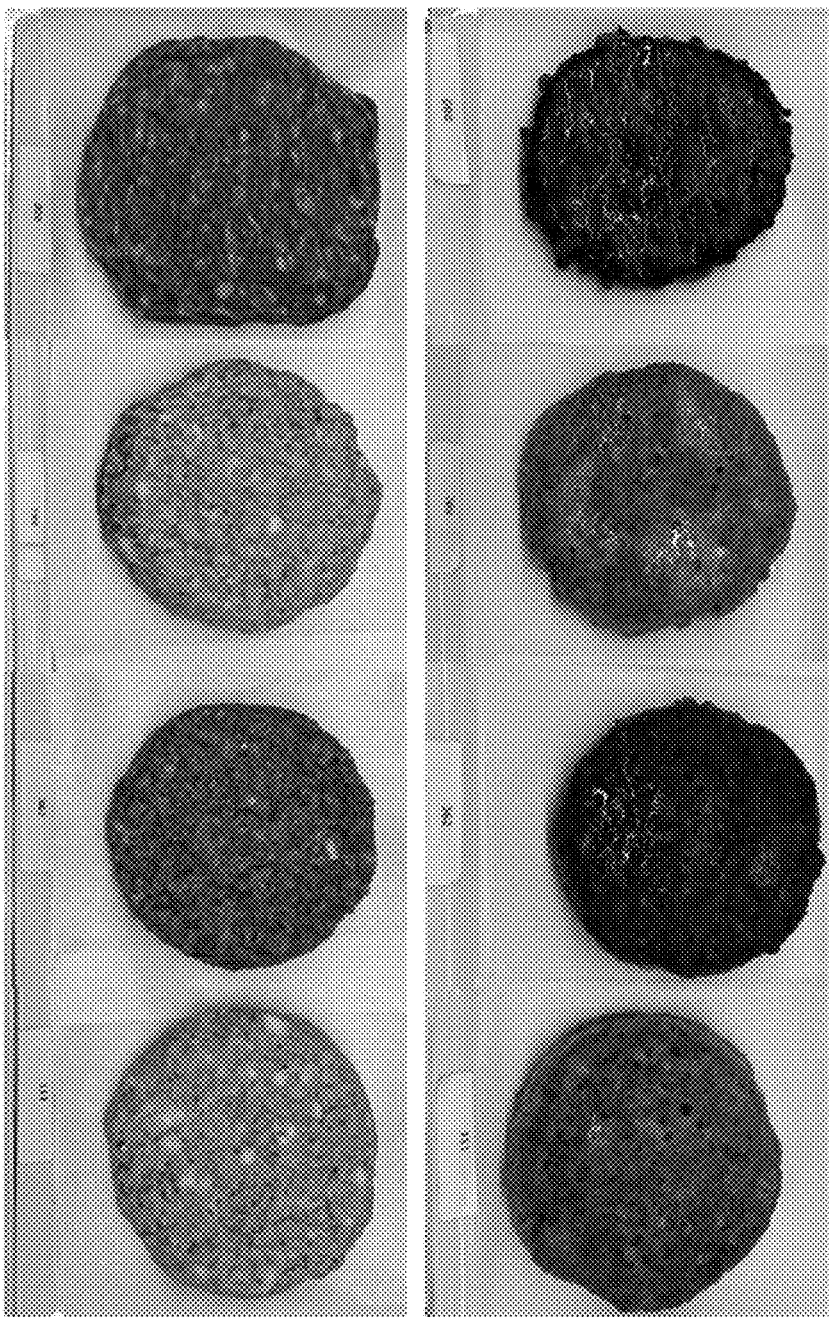

The results from this experiment are presented in a 0-100 scoring system, in which a score of 100 means that the specific feature is indistinguishable from that of the control beef patty for all trial participants, and a score of 0 means that the specific feature is indistinguishable from that of the control plant-based patty without any animal muscle cells/fat/myoglobin for all trial participants. The higher the score is, the closer it is to the corresponding feature of the beef patty. Images of these burger patties (before and after cooking) are shown in FIGS. 8A-8B.

Figure 3A:
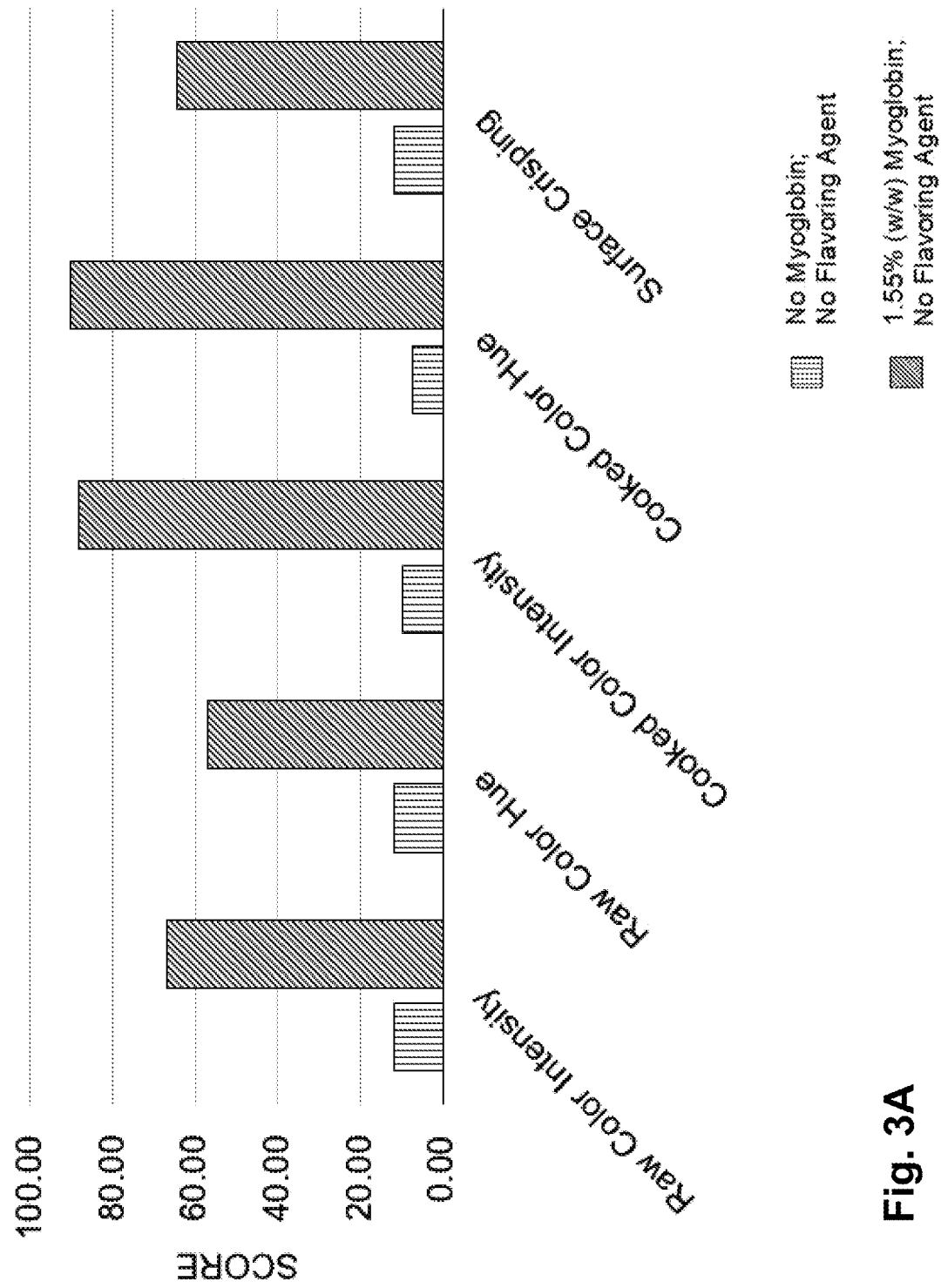
FIG. 3A-C shows the results of a consumer preference test of meat substitute products.
Figure 3B:
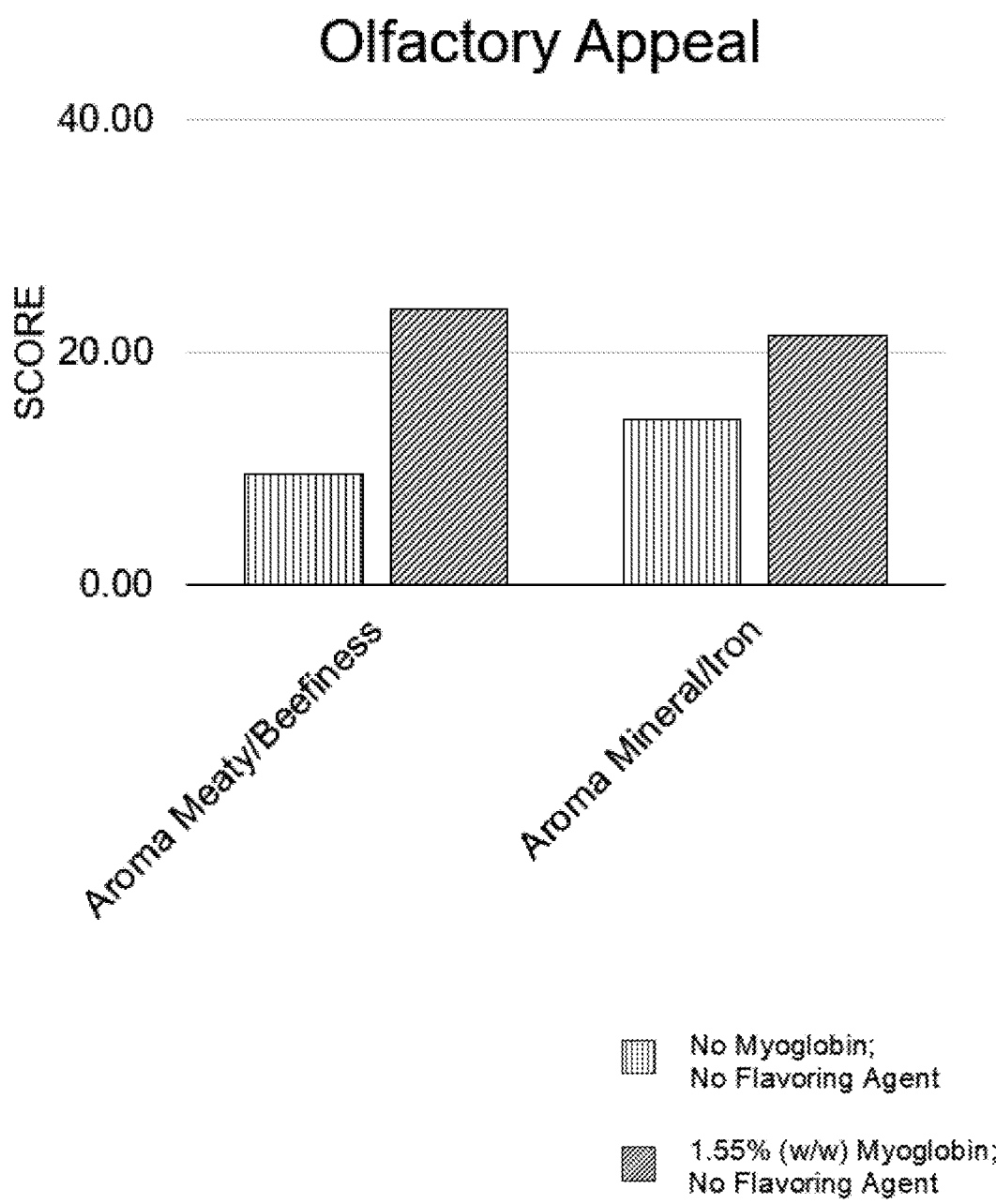

As shown in FIG. 3A, test patties incorporating 1.55% (w/w) exogenous myoglobin in addition to 5% (w/w) animal muscle cells and 5% (w/w) animal fat exhibited large improvements in visual appeal factors of raw color intensity, raw color hue, cooked color intensity, cooked color hue and surface crisping. Similarly, the addition of exogenous myoglobin to the patties containing 5% (w/w) animal muscle cells and 5% (w/w) animal fat resulted in further increases in olfactory appeal factors of meaty/beefiness aroma and mineral/iron aroma. (See FIG. 3B). These results were expected, as previous studies in Examples 2-3 had demonstrated a dose-dependent relationship for these visual and olfactory appeal factors based on the presence of total myoglobin.

Figure 3C:
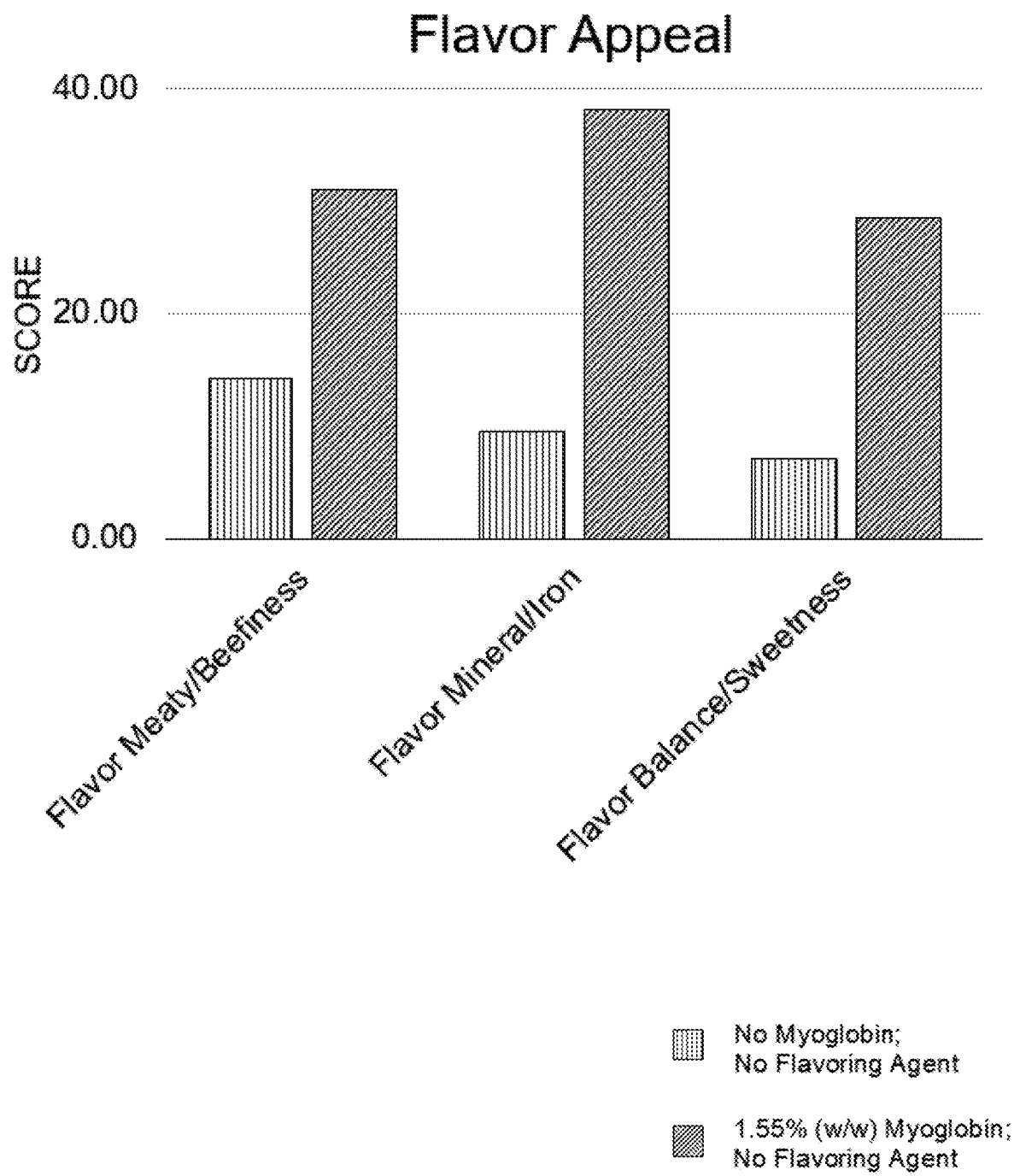

FIG. 3C demonstrated that the addition of 1.55% (w/w) exogenous myoglobin on top of patties containing 5% (w/w) animal muscle cells and 5% (w/w) animal fat resulted in drastic increases to flavor appeal factors of overall flavor intensity (meatiness and beefiness), mineral/iron flavor, and flavor balance/sweetness. These results were unexpected, as prior experiments from Examples 2-3 had shown limited/no flavor benefits above 0.50% (w/w) myoglobin. It was also interesting that the presence of 5% (w/w) animal muscle cells and 5% (w/w) animal fat resulted in only minor (10%-15%) improvements to flavor scores alone, but resulted in 30%-40% improvements when combined with exogenous myoglobin. Without wishing to be bound by any theory, Applicant believes that the flavor benefits of higher myoglobin contents are unlocked by the presence of animal cells, which potentially modulate and "bring out" the meatiness and beefiness flavor of the burger.

Figure 4A:
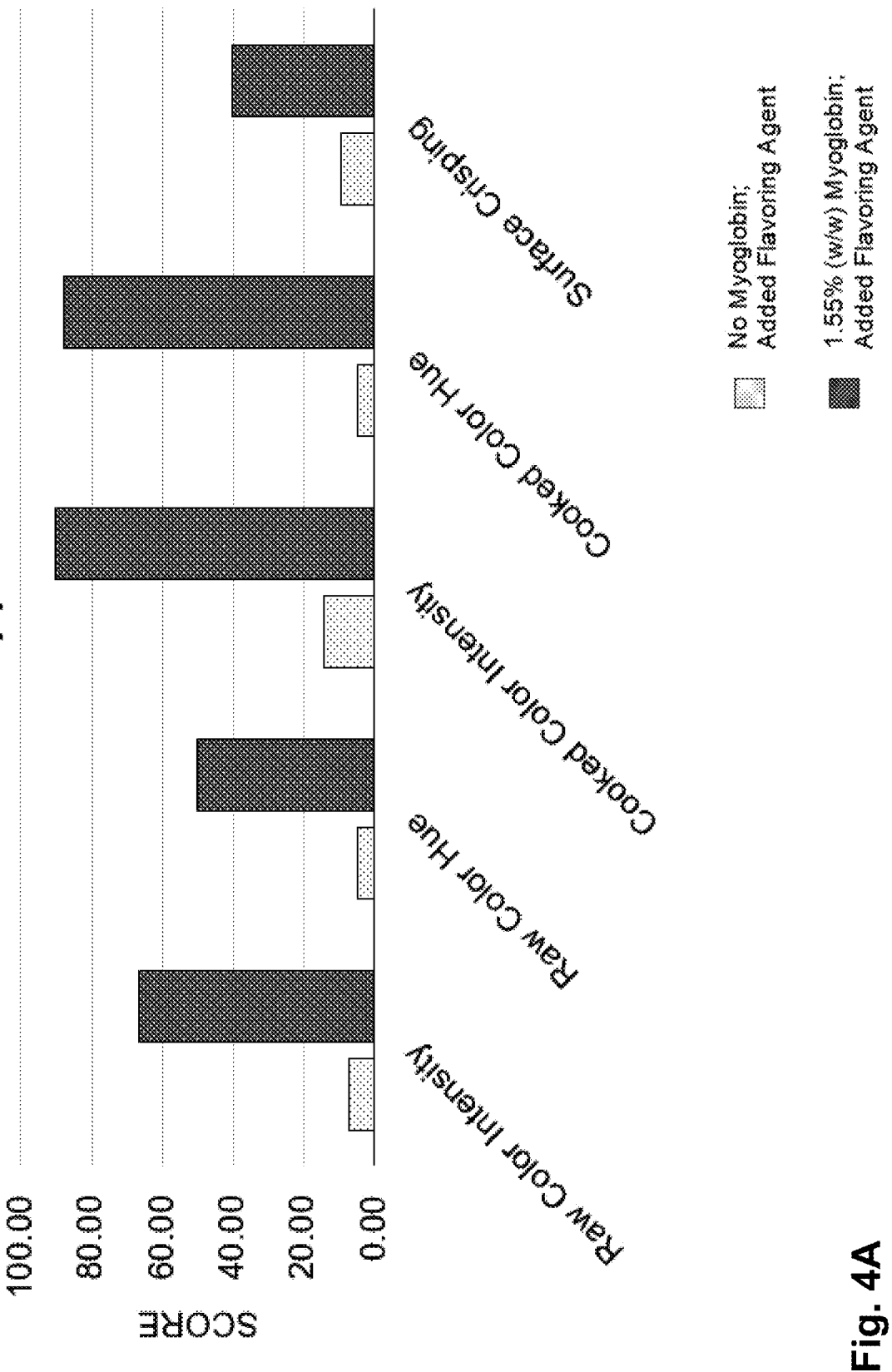
FIG. 4A-C shows the results of a consumer preference test of meat substitute products.
Figure 4B:
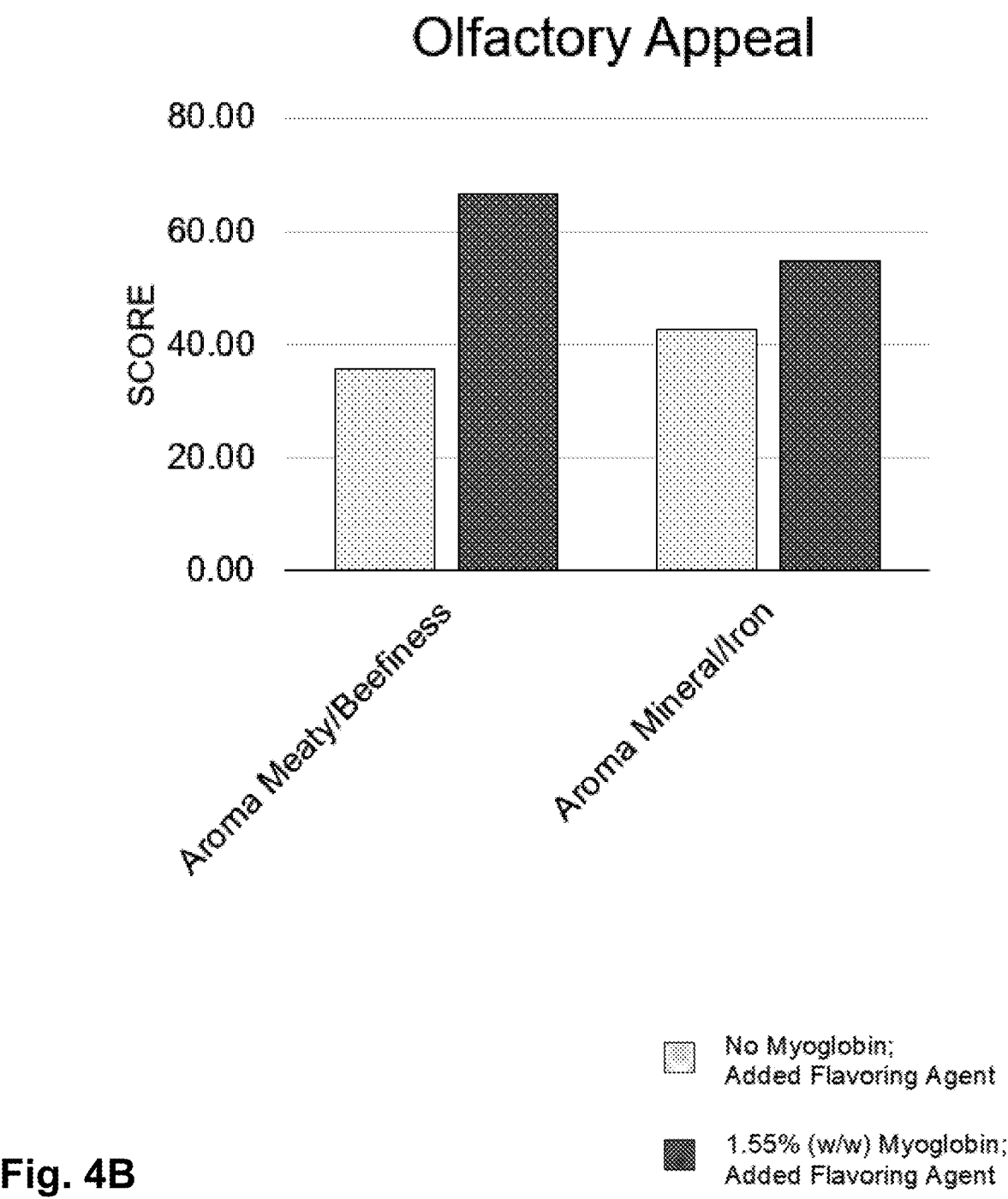
Figure 4C:
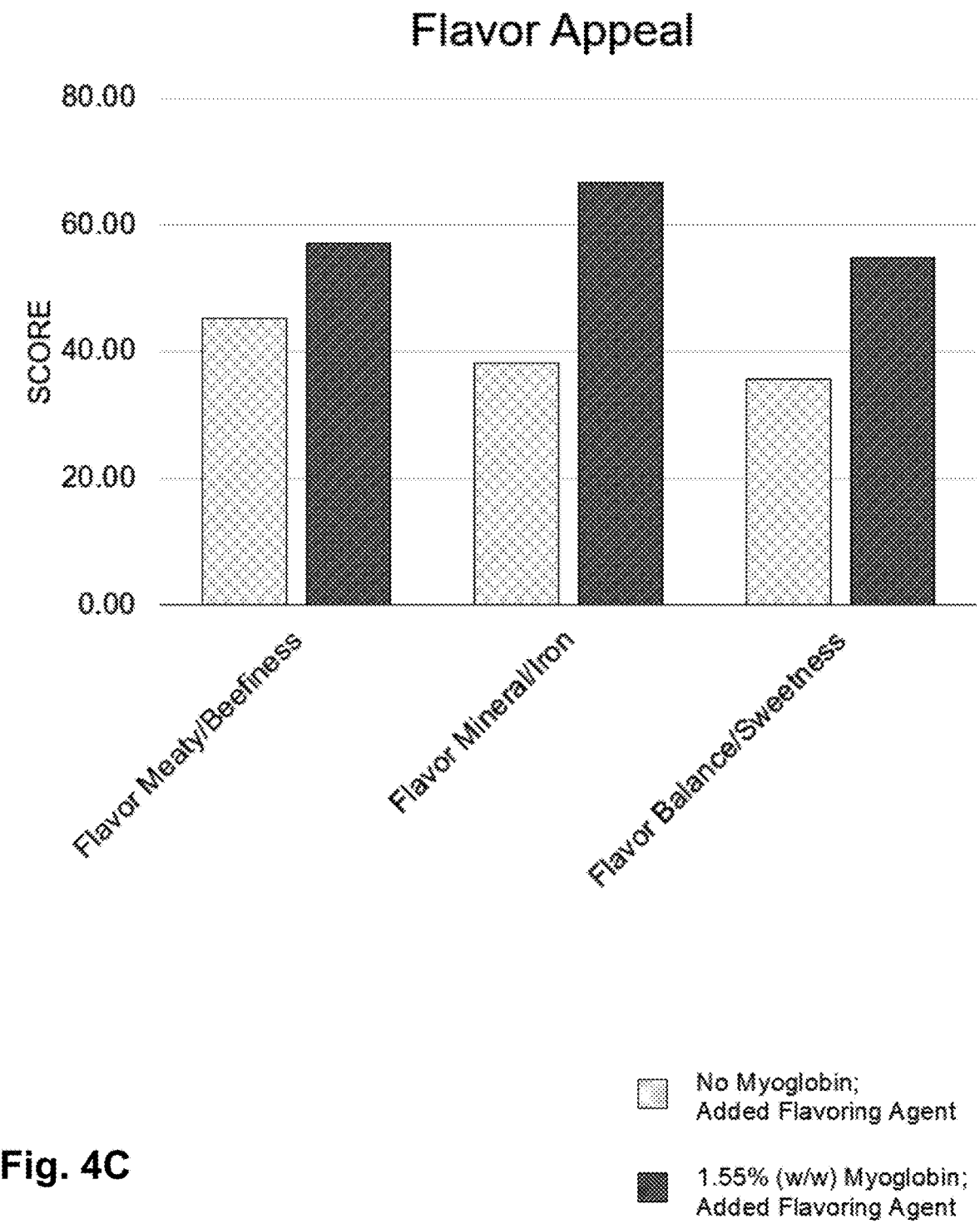

As discussed above, this experiment was also repeated using plant-based matrices with flavor additives also designed to increase meatiness and beefiness. The results from these experiments replicated the results for non-flavored plant-based matrixes. (See FIGS. 4A-4C). It is notable that the addition of exogenous myoglobin still resulted in drastic increases to all flavor appeal factors, especially to those of mineral/iron flavor, and overall flavor balance/sweetness. (See FIG. 4C). These results indicate that the flavor benefits of combination of exogenous myoglobin and animal muscle cells exist independent of recipe changes in the plant-based matrix.

Figure 5:
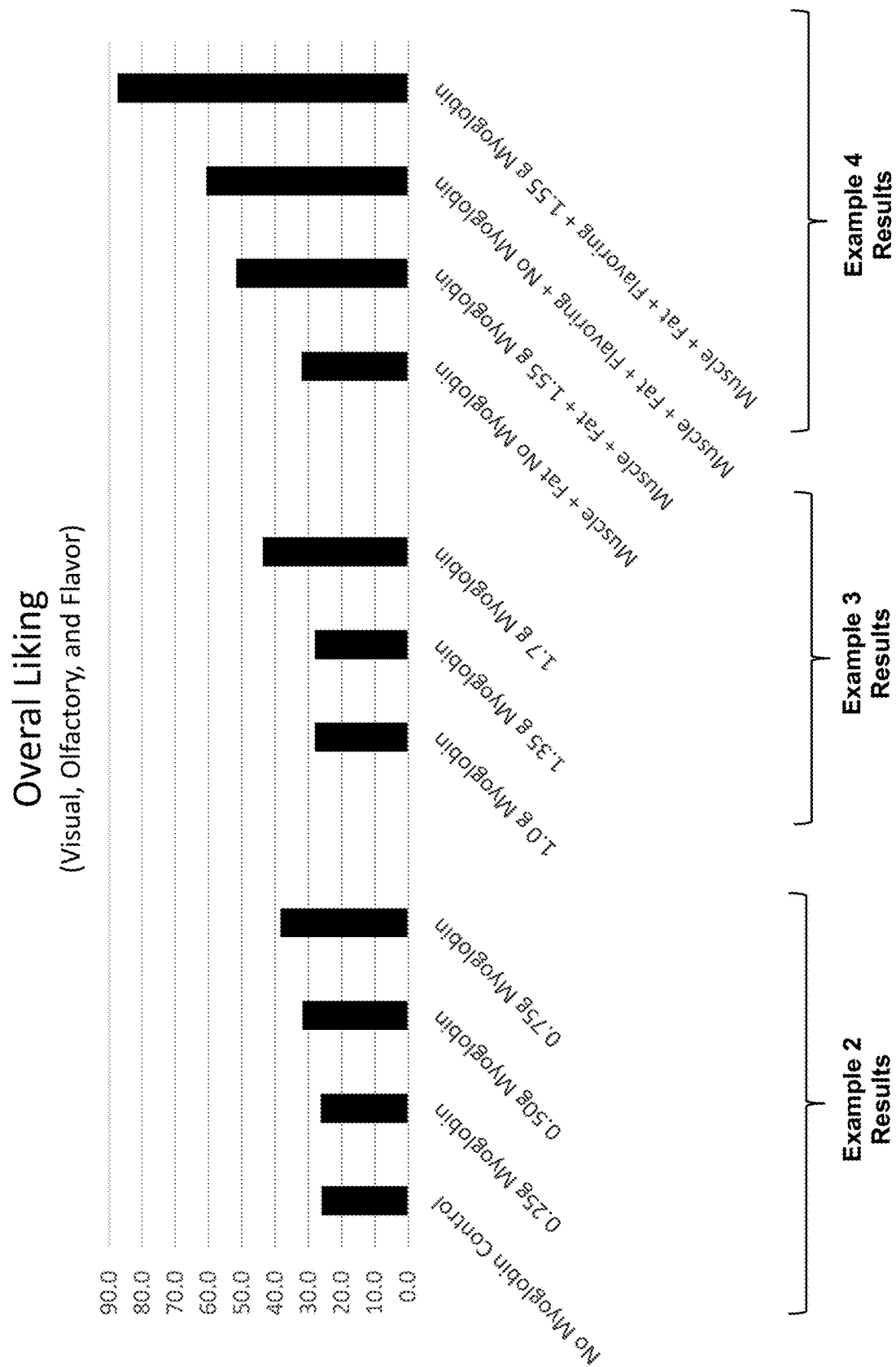
FIG. 5 is a chart showing the scores of overall liking of various meat substitute products.

Indeed, test patties containing 1.55% (w/w) exogenous myoglobin, 5% (w/w) animal muscle cells and 5% (w/w) animal fat in the flavored plant-based matrix exhibited higher than 85% overall liking/satisfaction scores, nearly matching those of the 100% beef burger controls. These results compare to the 25% scores for patties with 0.25% (w/w) myoglobin, and the ~40% highest score achievable by myoglobin alone at any tested concentration (See FIG. 5) These results suggest that exogenous myoglobin can be used to synergistically amplify the consumer likability of patties containing only a fractional amounts of animal muscle cells and animal fat cells, nearly mimicking the experience of a traditional beef burger, with only 5% of the muscle cells.

Example 5: Animal Cells and Exogenous Myoglobin Synergistically Improved the Sensory Profile of Hybrid Meat Substitute Product This set of experiments was designed to test how animal cells could improve the sensory profile of plant-based patties that contained low level (0.5%-0.75%) exogenous myoglobin. These experiments were conducted with a new commercial source of bovine myoglobin, and included proper controls to gain further insights into the flavor synergies achieved by combining exogeneous myoglobin with animal cells.

Test patties were produced in a process similar to those in Examples 2-4: mix water, seasoning, plant protein ingredients (e.g., plant protein ingredients derived from pea, soy and gluten), and emulsion phase and binding ingredients (e.g., methylcellulose or its emulsion) to make base burger patties. Selected samples also received exogenous hemeprotein (myoglobin) and/or animal cells (from harvested and macerated locomotive beef tissue). Mixed patties were then covered and stored in cold until ready to cook.

Consumer taste trials were conducted under standard controlled conditions using well-known and accepted food science protocols (see e.g., Sensory Evaluation of Foods, by Harry T. Lawless and Hildegarde Haymann. Second Edition. Publisher: Springer). Trial burger patties were thawed under refrigerated conditions (4° C.) and were then cooked on a skillet until they reached an internal temperature of 165° F. Patties were served alone, without any buns, burger trimmings, or any condiments or dressing to ensure that feedback was not influenced by other factors. Each tested sample was compared to two controls in a taste test: 1) a beef burger patty composed of CreamCo 100% beef shoulder clod (chuck), natural, corn finish; and 2) the same plant-based patty formula without myoglobin or animal cells. Multiple participants used a scoring system to evaluate the color and sensory profile of each formula. The results from these consumer taste trials are presented in a 0-100 scoring system, in which a score of 100 means that the specific feature was indistinguishable from that of the control beef patty for all trial participants, and a score of 0 means that the specific feature is indistinguishable from that of the control plant-based patty without any hemeprotein for all trial participants. The higher the score is, the closer it is to the corresponding feature of the beef patty.

Four different formulations of burger patties were tested in the study, as shown in Table 8 below:

TABLE 8

| Ingredients Group | Percentage (w/w) | | | |
|---|---|---|---|---|
| | 2.5% Animal Cell | 0.5% Myoglobin | 2.5% Animal Cell 0.5% Myoglobin | 2.5% Animal Cell 0.75% Myoglobin |
| Animal Cells | 2.5% | 0% | 2.5% | 2.5% |
| Myoglobin | 0% | 0.5% | 0.5% | 0.75% |
| Plant-Based Meat Doug | 97.5% | 99.5% | 97% | 96.75% |

Figure 6A:
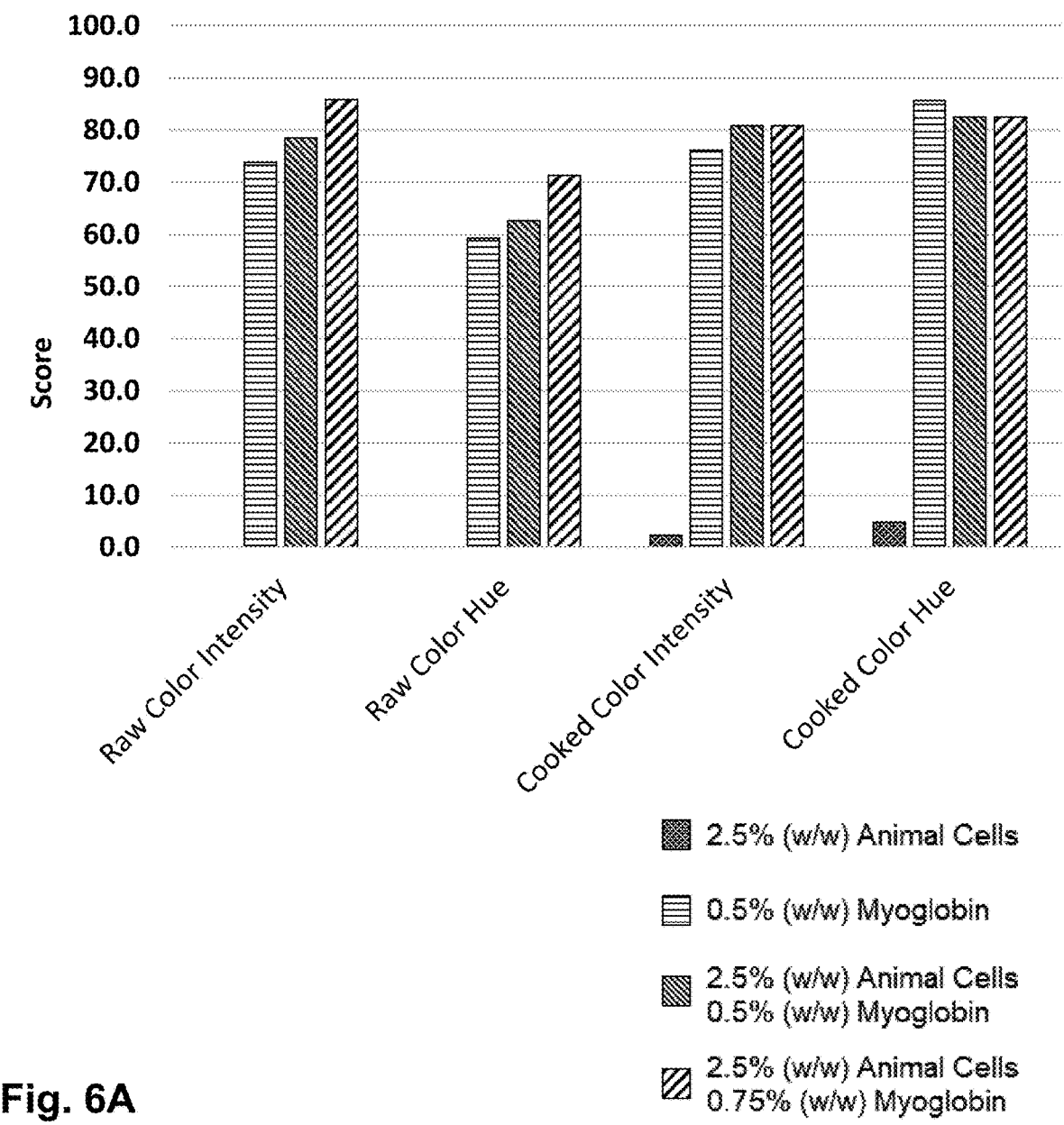
FIG. 6A-C shows the results of a consumer preference test of meat substitute products.
Figure 6B:
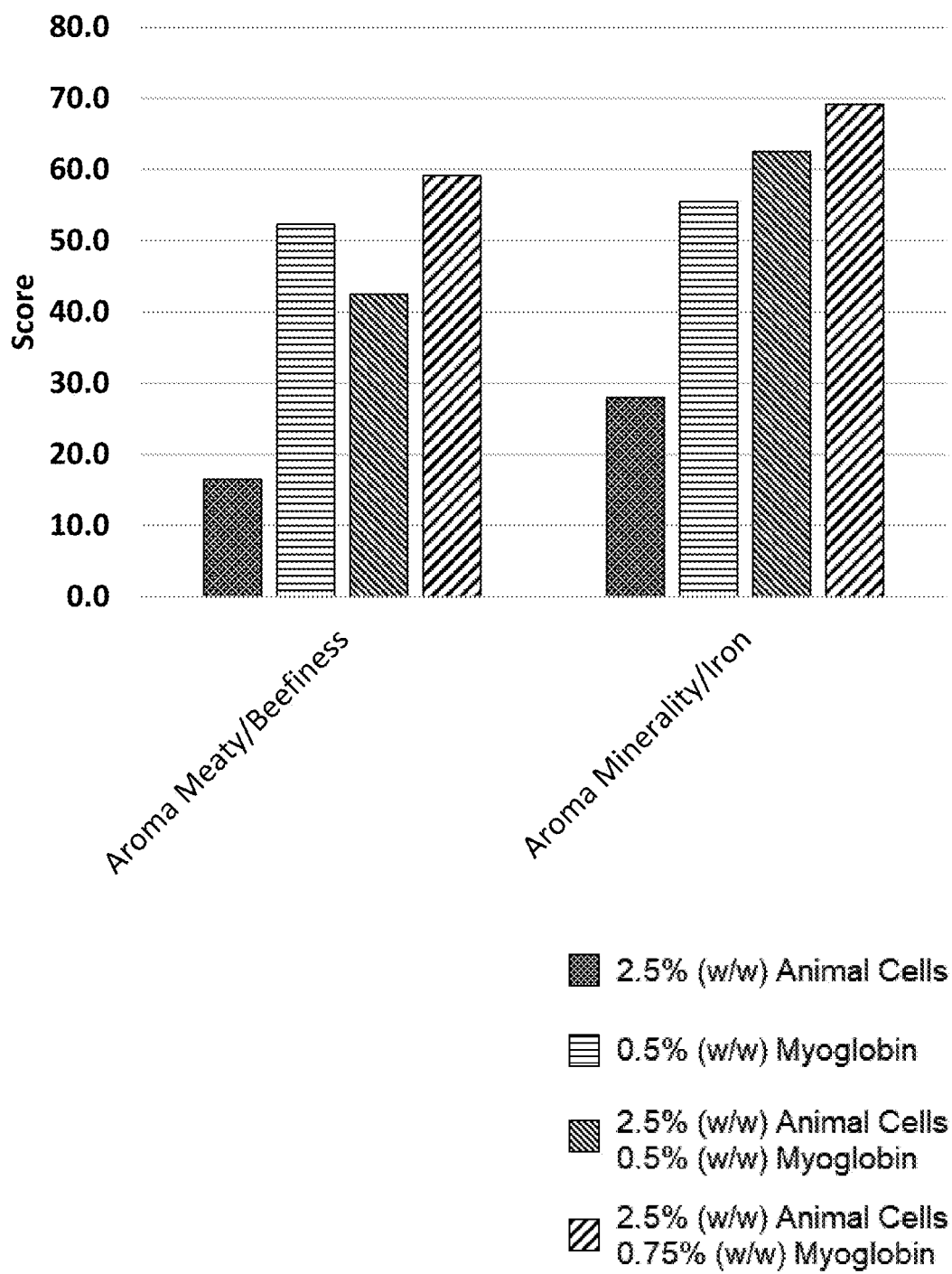
Figure 6C:
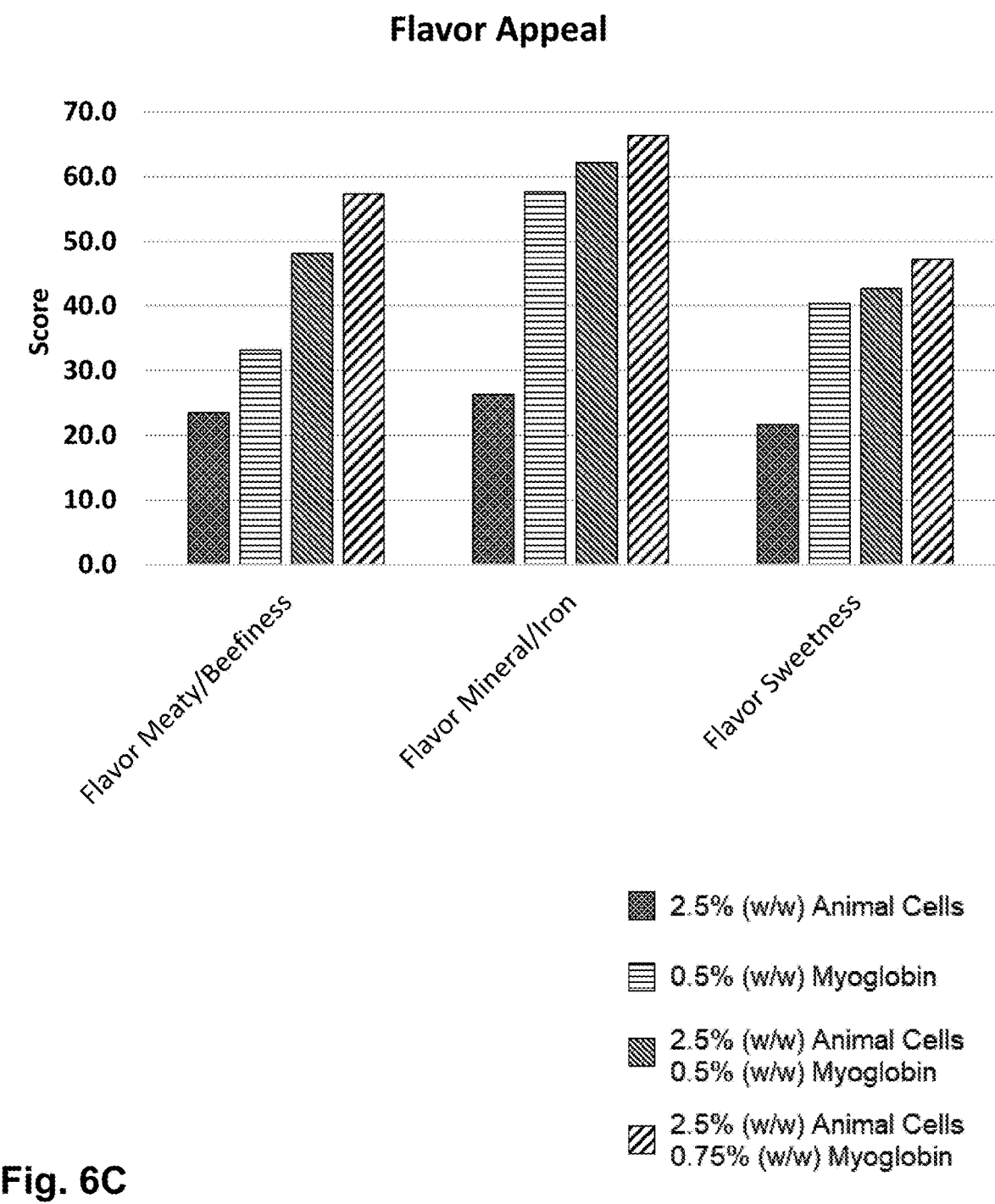

The results (FIG. 6A-6C) show that combining animal cells and myoglobin led to improvements of various visual, olfactory, and flavor attributes of the hybrid meat substitute product.

Notably, the combination of animal cells and exogenous myoglobin within the hybrid meat substitute product resulted in synergistic improvements in flavor scores. Specifically, as shown in the first 3 columns on the left of FIG. 6C, the addition of only 2.5% (w/w) of animal cells to a plant-based meat substitute product comprising exogenous myoglobin resulted in an outsized 45% improvement in flavor match ("Flavor Meaty/Beefiness") to full beef burgers compared to comparable meat analogues containing myoglobin but no cells, and a 105% improvement in flavor match to full beef burgers compared to meat analogues containing only the 2.5% (w/w) animal cells. In other words, the hybrid meat substitute product made out of i) plant-based meat dough, supplemented with small amounts of ii) exogenous myoglobin, and iii) animal cells, scored 45% and 105% higher in meaty/beefiness score than identical meat analogue parties that only lacked the animal cells or myoglobin, respectively.

The animal cells used in this study were derived from locomotive meat tissue, which contained about 12 mg/g myoglobin. The incorporation of the 2.5% (w/w) animal cells to the meat substitute product was thus equivalent to adding 0.03% (w/w) myoglobin. This represents a relative increase of only 6% in myoglobin content, but results in a 45% improvement in flavor scores.

Harvested animal cells, instead of cultivated cells, were used in this study because the latter remain extremely expensive to produce, and are therefore not a commercially viable ingredient to conduct multiple large taste trials. Taste tests with cultivated cells are expected to yield similar results, except that the effect of exogenous hemeproteins is expected to be more pronounced, given that cultivated cells have substantially lower inherent heme contents. A limited number of taste trials with cultivated cells were also carried out, which confirmed flavor improvements from combined cultivated animal cells and exogenous hemeprotein (results not shown).

Combining animal cells and exogenous myoglobin in the meat substitute product also unexpectedly extended the flavor gains that were attainable through the addition of hemeprotein. Earlier consumer taste trials using freshly extracted myoglobin had demonstrated that exogenous hemeproteins had a limited concentration range in which they could effectuate flavor improvements, with further increases in hemeprotein content resulting in no additional flavor gains. For example, in FIG. 1C, the flavor scored increases up to 0.5% (w/w) myoglobin content, followed by sharp reductions in flavor scores for meat analogues with myoglobin contents of 0.75% (w/w).

The addition of even small amounts of animal cells could overcome this "flavor plateau," and expand the concentration range at which exogenous hemeproteins could produce flavor improvements. As shown in columns 2-4 and 6-8 of FIG. 6C, the plant-based meat substitute product comprising both animal cells and exogenous myoglobin continued to exhibit Flavor Meaty/Beefiness and Flavor Mineral/Iron score increases past the 0.5% myoglobin "flavor plateau" of comparable meat analogues without animal cells.

Therefore, the results in this Example showed that the addition of animal cells improves the flavor and increases the concentration range at which hemeprotein flavor improvements occur, by overcoming the "flavor plateau" of non-animal cell-containing meat substitute products.

Example 6: The Hybrid Meat Substitute Product has Higher Overall Liking Compared to a Commercially Available Plant-Based Meat Substitute Product The hybrid meat substitute product was used to prepare a burger product ((termed "R&D Burger"), which was directly compared to the latest version of the commercially available Impossible Burger made from plant-based ingredients. The R&D Burger was formulated with a plant based meat dough, 0.5% (w/w) exogenous myoglobin, and 2.5% (w/w) animal cells, and was cooked on a skillet until it reached an internal temperature of 165° F. The Impossible Burger was purchased from a local supermarket off the shelf, and cooked according to package instructions. Briefly, patties sized at 113 g (the same weight as the R&D Burger) were formed and cooked in the griddle to 165° F.

Both the Impossible Burger and the R&D Burger were subjected to the consumer taste trial against each other. Testers were asked to rank their overall liking of each of the burgers within a scale of 1-9. Participants were asked to consider aspects of: visual appeal when raw, cooked visual appeal, cooked aroma, cooked taste, and cooked texture. Only the burger patties were tested, to avoid confounding effects of bread, condiments, and other burger trimmings. As shown in Table 9 below, the R&D Burger was assigned an average score of 7.5, while the Impossible Burger was assigned an average score of only 6.

TABLE 9

|  | Overall Liking | Raw visual | Cooked visual | Cooked aroma | Taste | Texture |
|---|---|---|---|---|---|---|
| Impossible Burger | 6 | 3.67 | 3.67 | 2.50 | 3.67 | 2.67 |
| R&D Burger | 7.5 | 4.17 | 3.83 | 3.83 | 3.33 | 3.67 |
| Highest possible score | 9 | 5 | 5 | 5 | 5 | 5 |

Accordingly, the R&D Burger with 1) a plant-based meat dough, supplemented with small amounts of ii) exogenous myoglobin, and iii) animal cells, scored 25% higher in overall liking than the Impossible Burger.

Example 7: Adding Animal Fat Improves the Fatty Mouthfeel of the Hybrid Meat Substitute Product Comprising Exogenous Myoglobin Experiments were conducted to test whether adding animal fat would improve the taste of the hybrid meat substitute product. Briefly, a plant-based meat dough was mixed with beef muscle (representing animal cells; 5% final w/w), fat (animal and/or plant-based; 12% total fat w/w), flavors, and optionally exogenous hemeprotein, to form patties. The final percentage (w/w) of exogenous myoglobin was 0%, 0.45%, or 0.9% in each formulation. Because an additional 0.06% (w/w) of myoglobin was present in the 5% w/w beef muscle, the total amount of myoglobin in the formulation was 0%, 0.51%, or 0.96% (w/w). The total amount of fat (animal and plant-based) was kept at 12%. Table 10 below shows the different formulations of burger patties tested in this Example:

TABLE 10

| | Percentage (w/w) Group | | | | | | |
|---|---|---|---|---|---|---|---|
| Ingredients | 1 | 2 | 3 | 4 | 5 | 6 | 7 |
| Myoglobin (total) | 0.06% | 0.06% | 0.51% | 0.51% | 0.51% | 0.96% | 0.96% |
| Animal Fat | 6% | 12% | 0% | 7.2% | 0% | 5.4% | 12% |
| Plant-based Fat | 6% | 0% | 12% | 4.8% | 12% | 6.6% | 0% |
| Animal Cells | 5% | 5% | 5% | 5% | 5% | 5% | 5% |
| Plant-Based Matrix | 82.94% | 82.94% | 82.49% | 82.49% | 82.49% | 82.04% | 82.04% |

Two controls were also included: (1) the positive control of beef patty, using CreamCo 100% Beef shoulder clod (Chuck), natural, corn finish; (2) a negative control of plant-based meat dough with 12% plant-based fat and without flavor or myoglobin. The patties were cooked on an electric griddle at setting 350° F. until the internal temperature reached 160° F. Eight trial participants were asked to assess various parameters (e.g., raw visual, cooked visual, aroma, texture, flavor) of each test patty based on its degree of closeness between the two controls. The results were presented in a 0-100 scoring system, in which a score of 100 means that the specific feature was indistinguishable from that of the positive control (beef patty) for all participants, and a score of 0 means that the specific feature was indistinguishable from that of the control plant-based patty for all trial participants.

Figure 7:
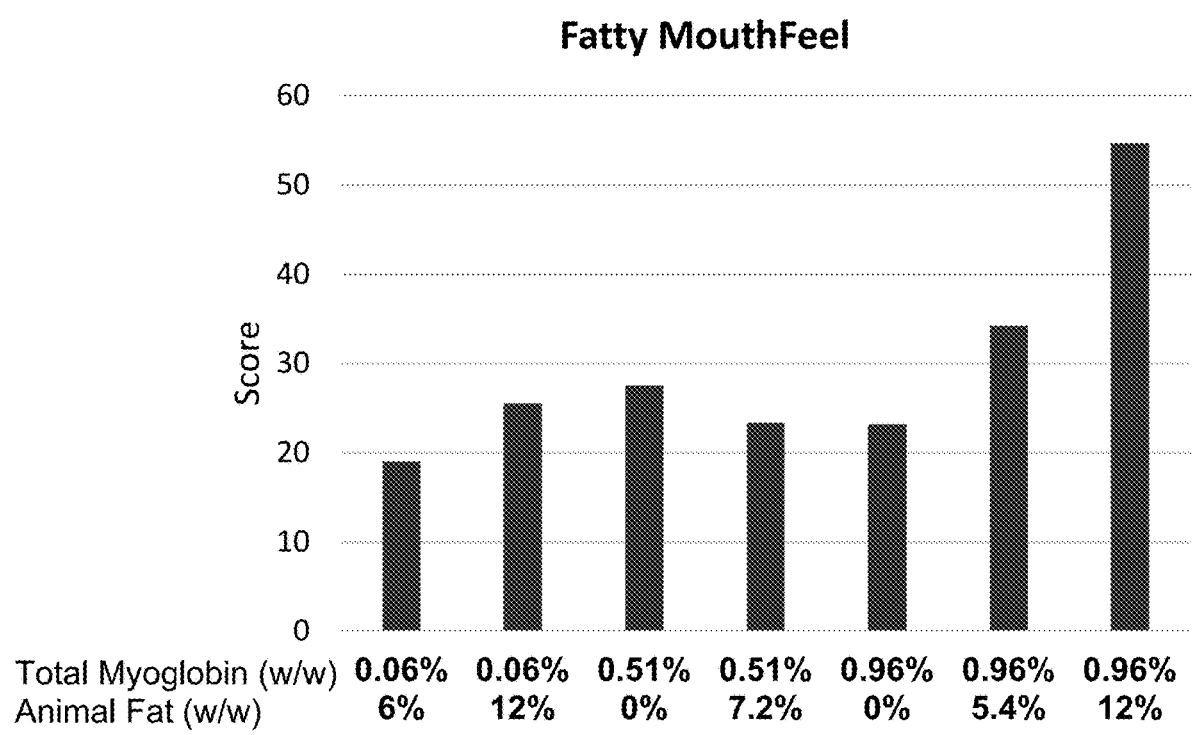
FIG. 7 is a chart showing the score of fatty mouthfeel texture factor for meat substitute products comprising the 5% (w/w) animal cells and 12% (w/w) total fat, with the indicated amount of total myoglobin and animal fat.

Interestingly, the results suggested that the presence of exogenous heme-containing protein contributed to the hybrid meat substitute product's overall fatty mouthfeel. Specifically, the presence of exogenous myoglobin increased the fatty mouthfeel of added animal fat. As shown in FIG. 7, when a significant amount of exogenous myoglobin was present (e.g., 0.96 total myoglobin), replacing plant-based fat with animal fat significantly improved the fatty mouthfeel of the hybrid meat substitute product (see the two columns on the right of FIG. 7). On the other hand, patties without exogenous myoglobin did not show such fatty mouthfeel taste improvement when the plant-based fat was replaced with animal fat. Therefore, exogenous myoglobin and animal fat synergistically increase the fatty mouthfeel texture of the hybrid meat substitute product.

Example 8: Testing the Effect of Different Levels of Exogenous Heme-Containing Protein and Animal Fat on Color and Sensory Profile of Plant-Based Patty An experiment is designed to test how different levels of exogenous heme-containing protein and animal fat could improve the sensory profile of burger patties. As outlined in Table 11 below, test burger patties contain different levels of exogenous bovine myoglobin and animal fat, but the total fat level (plant fat+animal fat) is kept at 12% (w/w) for all the patties. In addition, the patties also contain 5% (w/w) animal cells and 3% (w/w) flavoring agent and prepared according to the protocol in Example 4 above. The animal cells are sourced from slaughtered beef for this experiment, but can also be non-harvested animal cells (e.g., cultivated cells).

Similar to the experiments of Example 4 above, each tested patty formula is compared to two controls: 1) the 100% beef patty as described above, and 2) the same plant-based patty with the flavoring agent used to formulate the test patties, but lacking any of the added myoglobin/animal muscle cells/fat.

Persons having skill in the art will recognize that patties containing animal muscle cells contained higher basal myoglobin contents compared to purely plant-based control patties. Applicant estimates, based on the myoglobin content of the animal muscle cells, that the 5% animal muscle cells imparted about 0.06% basal myoglobin content to all test patties. The results from this experiment will be presented in a 0-100 scoring system, in which a score of 100 means that the specific feature is indistinguishable from that of the control beef patty for all trial participants, and a score of 0 means that the specific feature is indistinguishable from that of the control plant-based patty without any animal muscle cells/fat/myoglobin for all trial participants.

Example 9: Removal of Methylcellulose Binder from Hybrid Meat Substitute Product This Example explored the structural integrity and texture of hybrid meat substitute products without artificial binders. Specifically, commercial meat substitute products utilize methylcellulose emulsion (a carbohydrate gel) as a binder to bind all ingredients together and to provide greater firmness in the finished product. Methylcellulose is particularly popular, because of its increased firmness post cooking, which mimics the properties of ground meat.

Figure 9A:
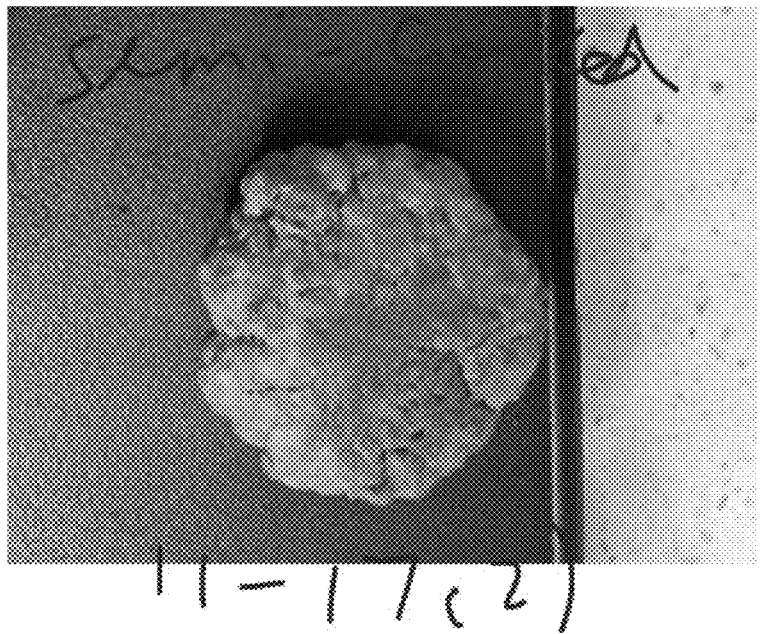
FIG. 9A-B depict pictures of meat substitute products according to the present disclosure.
Figure 9B:
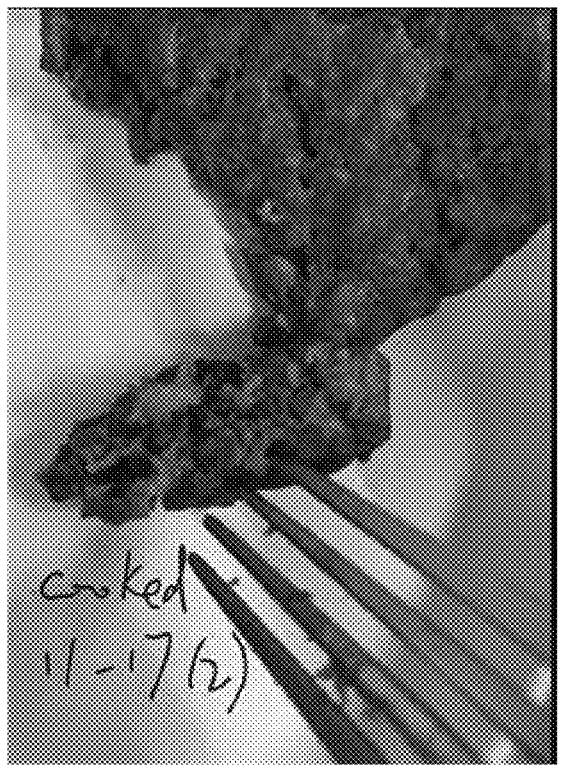

The instant inventors hypothesized that the animal cells within the presently disclosed hybrid meat substitute product could act as a binder, thereby removing the need for any additional binders. Two trial burger patties were prepared. The control patty contained only the plant-based meat dough as described in earlier examples, with ~22% methylcellulose emulsion. The test patty comprised the plant-based meat dough without methylcellulose, but with 15% added animal cells. The resulting test patty bound well in its raw form, and further maintained its integrity well after cooking. (See FIG. 9A and FIG. 9B) The results suggested that the presently claimed hybrid meat substitute products would not require binders, such as methylcellulose.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as, an acknowledgment or any form of suggestion that they constitute valid prior art or form part of the common general knowledge in any country in the world.

TABLE 11

| Group | 1 | 2 | 3 | 4 | 5 | 6 | 7 | 8 |
|---|---|---|---|---|---|---|---|---|
| Exogenous Myoglobin | 0.45% | 0% | 0.90% | 0% | 0.90% | 0.45% | 0.90% | 0% |
| Animal Muscle cells | 5% | 5% | 5% | 5% | 5% | 5% | 5% | 5% |
| Animal Fat | 0% | 12% | 0% | 0% | 5.40% | 7.20% | 12% | 6% |
| Flavoring Agent | 3% | 3% | 3% | 3% | 3% | 3% | 3% | 3% |
| Plant-Based Matrix (Fat adjusted) | 91.55% | 80% | 91.10% | 92% | 85.70% | 84.35% | 79.10% | 86% |

The invention claimed is:

1. A hybrid meat substitute product comprising:
   a) at least 60% by weight plant-based meat dough;
   b) at least 2.5% by weight cultured animal cells; and
   c) at least 0.50% by weight exogenous heme-containing protein,
   wherein the cultured animal cells and the exogenous heme-containing protein synergistically improve the meaty flavor of the hybrid meat substitute product.

2. The hybrid meat substitute product of claim 1, comprising:
   d) animal fat.

3. The hybrid meat substitute product of claim 1, wherein the animal cells comprise, or are derived from, skeletal muscle cells, myoblasts, myogenic cells, fibroblasts, mesenchymal stem cells, endothelial cells, adipose progenitor cells, preadipocytes, or cardiomyocytes.

4. The hybrid meat substitute product of claim 1, wherein the animal cells are not hepatocytes.

5. The hybrid meat substitute product of claim 1, wherein the animal cells are myoblasts.

6. The hybrid meat substitute product of claim 1, wherein the animal cells are fibroblasts.

7. The hybrid meat substitute product of claim 1, wherein the animal cells are not in a meat structure.

8. The hybrid meat substitute product of claim 1, comprising between 2.5-20% the animal cells by weight.

9. The hybrid meat substitute product of claim 1, comprising between 2.5-6% the animal cells by weight.

10. The hybrid meat substitute product of claim 1, comprising between 0.5-2% the exogenous heme-containing protein by weight.

11. The hybrid meat substitute product of claim 1, comprising at least 0.75% the exogenous heme-containing protein by weight.

12. The hybrid meat substitute product of claim 1, wherein the exogenous heme-containing protein is selected from the group consisting of a non-symbiotic hemoglobin, a Hell's gate globin I, a flavohemoprotein, a leghemoglobin, a heme-dependent peroxidase, a cytochrome c peroxidase, a mammalian myoglobin, an androglobin, a cytoglobin, a globin E, a globin X, a globin Y, a hemoglobin, a myoglobin, an erythrocruorin, a beta hemoglobin, an alpha hemoglobin, a protoglobin, a cyanoglobin, a cytoglobin, a histoglobin, a neuroglobins, a chlorocruorin, a truncated hemoglobin, a truncated 2/2 globin, a hemoglobin 3, a cytochrome, and a peroxidase.

13. The hybrid meat substitute product of claim 1, wherein the exogenous heme-containing protein is a myoglobin.

14. The hybrid meat substitute product of claim 13, wherein at least 50% of the myoglobin is oxymyoglobin.

15. The hybrid meat substitute product of claim 1, wherein the heme-containing protein is bovine myoglobin, wherein the bovine myoglobin comprises an amino acid sequence having at least 80%, 85%, 90%, or 95% identity to SEQ ID NO: 1.

16. The hybrid meat substitute product of claim 2, wherein the animal fat is from cultivated cells.

17. The hybrid meat substitute product of claim 2, wherein the animal fat is from cultivated adipocytes.

18. The hybrid meat substitute product of claim 2, comprising between 0.1-30% the animal fat by weight.

19. The hybrid meat substitute product of claim 2, comprising between 10-20% total fat by weight.

20. The hybrid meat substitute product of claim 1, wherein the exogenous heme-containing protein is provided as a cell-free ingredient.

* * * * *

SEQUENCE LISTING

```
Sequence total quantity: 31
SEQ ID NO: 1                  moltype = AA  length = 154
FEATURE                       Location/Qualifiers
source                        1..154
                              mol_type = protein
                              organism = Bos taurus
SEQUENCE: 1
MGLSDGEWQL VLNAWGKVEA DVAGHGQEVL IRLFTGHPET LEKFDKFKHL KTEAEMKASE    60
DLKKHGNTVL TALGGILKKK GHHEAEVKHL AESHANKHKI PVKYLEFISD AIIHVLHAKH   120
PSDFGADAQA AMSKALELFR NDMAAQYKVL GFHG                              154

SEQ ID NO: 2                  moltype = AA  length = 133
FEATURE                       Location/Qualifiers
source                        1..133
                              mol_type = protein
                              organism = Methylacidiphilum infernorum
SEQUENCE: 2
MIDQKEKELI KESWKRIEPN KNEIGLLFYA NLFKEEPTVS VLFQNPISSQ SRKLMQVLGI    60
LVQGIDNLEG LIPTLQDLGR RHKQYGVVDS HYPLVGDCLL KSIQEYLGQG FTEEAKAAWT   120
KVYGIAAQVM TAE                                                     133

SEQ ID NO: 3                  moltype = AA  length = 139
FEATURE                       Location/Qualifiers
source                        1..139
                              mol_type = protein
                              organism = Aquifex aeolicus
SEQUENCE: 3
MLSEETIRVI KSTVPLLKEH GTEITARMYE LLFSKYPKTK ELFAGASEEQ PKKLANAIIA    60
YATYIDRLEE LDNAISTIAR SHVRRNVKPE HYPLVKECLL QAIEEVLNPG EEVLKAWEEA   120
YDFLAKTLIT LEKKLYSQP                                               139

SEQ ID NO: 4                  moltype = AA  length = 145
FEATURE                       Location/Qualifiers
source                        1..145
                              mol_type = protein
                              organism = Glycine max
SEQUENCE: 4
MGAFTEKQEA LVSSSFEAFK ANIPQYSVVF YTSILEKAPA AKDLFSFLSN GVDPSNPKLT    60
GHAEKLFGLV RDSAGQLKAN GTVVADAALG SIHAQKAITD PQFVVVKEAL LKTIKEAVGD   120
KWSDELSSAW EVAYDELAAA IKKAF                                        145

SEQ ID NO: 5                  moltype = AA  length = 162
FEATURE                       Location/Qualifiers
source                        1..162
                              mol_type = protein
                              organism = Hordeum vulgare
SEQUENCE: 5
MSAAEGAVVF SEEKEALVLK SWAIMKKDSA NLGLRFFLKI FEIAPSARQM PPFLRDSDVP    60
LETNPKLKTH AVSVFVMTCE AAAQLRKAGK ITVRETTLKR LGGTHLKYGV ADGHFEVTRF   120
ALLETIKEAL PADMWGPEMR NAWGEAYDQL VAAIKQEMKP AE                     162

SEQ ID NO: 6                  moltype = AA  length = 1153
FEATURE                       Location/Qualifiers
source                        1..1153
                              mol_type = protein
                              organism = Magnaporthe oryzae
SEQUENCE: 6
MDGAVRLDWT GLDLTGHEIH DGVPIASRVQ VMVSFPLFKD QHIIMSSKES PSRKSSTIGQ    60
STRNGSCQAD TQKGQLPPVG EKPKPVKENP MKKLKEMSQR PLPTQHGDGT YPTEKKLTGI   120
GEDLKHIRGY DVKTLLAMVK SKLKGEKLKD DKTMLMERVM QLVARLPTES KKRAELTDSL   180
INELWESLDH PPLNYLGPEH SYRTPDGSYN HPFNPQLGAA GSRYARSVIP TVTPPGALPD   240
PGLIFDSIMG RTPNSYRKHP NNVSSILWYW ATIIIHDIFW TDPRDINTNK SSSYLDLAPL   300
YGNSQEMQDS IRTFKDGRMK PDCYADKRLA GMPPGVSVLL IMFNRFHNHV AENLALINEG   360
GRFNKPSDLL EGEAREAAWK KYDNDLFQVA RLVTSGLYIN ITLVDYVRNI VNLNRVDTTW   420
TLDPRQDAGA HVGTADGAER GTGNAVSAEF NLCYRWHSCI SEKDSKFVEA QFQNIFGKPA   480
SEVRPDEMWK GFAKMEQNTP ADPGQRTFGG FKRGPDGKFD DDDLVRCISE AVEDVAGAFG   540
ARNVPQAMKV VETMGIIQGR KWNVAGLNEF RKHFHLKPYS TFEDINSDPG VAEALRRLYD   600
HPDNVELYPG LVAEEDKQPM VPGVGIAPTY TISRVVLSDA VCLVRGDRFY TTDFTPRNLT   660
NWGYKEVDYD LSVNHGCVFY KLFIRAFPNH FKQNSVYAHY PMVVPSENKR ILEALGRADL   720
FDFEAPKYIP PRVNITSYGG AEYILETQEK YKVTWHEGLG FLMGEGGLKF MLSGDDPLHA   780
QQRKCMAAQL YKDGWTEAVK AFYAGMMEEL LVSKSYFLGN NKHRHVDIIR DVGNMVVHF   840
ASQVFGLPLK TAKNPTGVFT EQEMYGILAA IFTTIFFDLD PSKSFPLRTK TREVCQKLAK   900
LVEANVKLIN KIPWSRGMFV GKPAKDEPLS IYGKTMIKGL KAHGLSDYDI AWSHVVPTSG   960
AMVPNQAQVF AQAVDYYLSP AGMHYIPEIH MVALQPSTPE TDALLLGYAM EGIRLAGTFG  1020
SYREAAVDDV VKEDNGRQVP VKAGDRVFVS FVDAARDPKH FPDPEVVNPR RPAKKYIHYG  1080
VGPHACLGRD ASQIAITEMF RCLFRRRNVR RVPGPQGELK KVPRPGGFYV YMREDWGGLF  1140
PFPVTMRVMW DDE                                                    1153
```

```
SEQ ID NO: 7                moltype = AA   length = 530
FEATURE                     Location/Qualifiers
source                      1..530
                            mol_type = protein
                            organism = Fusarium oxysporum
SEQUENCE: 7
MKGSATLAFA LVQFSAASQL VWPSKWDEVE DLLYMQGGFN KRGFADALRT CEFGSNVPGT    60
QNTAEWLRTA FHDAITHDAK AGTGGLDASI YWESSRPENP GKAFNNTFGF FSGFHNPRAT   120
ASDLTALGTV LAVGACNGPR IPFRAGRIDA YKAGPAGVPE PSTNLKDTFA APFTKAGFTKE  180
EMTAMVACGH AIGGVHSVDF PEIVGIKADP NNDTNVPFQK DVSSFHNGIV TEYLAGTSKN   240
PLVASKNATF HSDKRIFDND KATMKKLSTK AGFNSMCADI LTRMIDTVPK SVQLTPVLEA   300
YDVRPYITEL SLNNKNKIHF TGSVRVRITN NIRDNNDLAI NLIYVGRDGK KVTVPTQQVT   360
FQGGTSFGAG EVFANFEFDT TMDAKNGITK FFIQEVKPST KATVTHDNQK TGGYKVDDTV   420
LYQLQQSCAV LEKLPNAPLV VTAMVRDARA KDALTLRVAH KKPVKGSIVP RFQTAITNFK   480
ATGKKSSGYT GFQAKTMFEE QSTYFDIVLG GSPASGVQFL TSQAMPSQCS              530

SEQ ID NO: 8                moltype = AA   length = 358
FEATURE                     Location/Qualifiers
source                      1..358
                            mol_type = protein
                            organism = Fusarium graminearum
SEQUENCE: 8
MASATRQFAR AATRATRNGF AIAPRQVIRQ QGRRYYSSEP AQKSSSAWIW LTGAAVAGGA    60
GYYFYGNSAS SATAKVFNPS KEDYQKVYNE IAARLEEKDD YDDGSYGPVL VRLAWHASGT   120
YDKETGTGGS NGATMRFAPE SDHGANAGLA AARDFLQPVK EKFPWITYSD LWILAGVCAI   180
QEMLGPAIPY RPGRSDRDVS GCTPDGRLPD ASKRQDHLIG IFGRMGFNDQ EIVALSGAHA   240
LGRCHTDRSG YSGPWTFSPT VLTNDYFRLL VEEKWQWKKW NGPAQYEDKS TKSLMMLPSD   300
IALIEDKKFK PWVEKYAKDN DAFFKDFSNV VLRLFELGVP FAQGTENQRW TFKPTHQE     358

SEQ ID NO: 9                moltype = AA   length = 122
FEATURE                     Location/Qualifiers
source                      1..122
                            mol_type = protein
                            organism = Chlamydomonas moewusii
SEQUENCE: 9
MSLFAKLGGR EAVEAAVDKF YNKIVADPTV STYFSNTDMK VQRSKQFAFL AYALGGASEW    60
KGKDMRTAHK DLVPHLSDVH FQAVARHLSD TLTELGVPPE DITDAMVVA STRTEVLNMP   120
QQ                                                                  122

SEQ ID NO: 10               moltype = AA   length = 121
FEATURE                     Location/Qualifiers
source                      1..121
                            mol_type = protein
                            organism = Tetrahymena pyriformis
SEQUENCE: 10
MNKPQTIYEK LGGENAMKAA VPLFYKKVLA DERVKHFFKN TDMDHQTKQQ TDFLTMLLGG    60
PNHYKGKNMT EAHKGMNLQN LHFDAIIENL AATLKELGVT DAVINEAAKV IEHTRKDMLG   120
K                                                                   121

SEQ ID NO: 11               moltype = AA   length = 117
FEATURE                     Location/Qualifiers
source                      1..117
                            mol_type = protein
                            organism = Paramecium caudatum
SEQUENCE: 11
MSLFEQLGGQ AAVQAVTAQF YANIQADATV ATFFNGIDMP NQTNKTAAFL CAALGGPNAW    60
TGRNLKEVHA NMGVSNAQFT TVIGHLRSAL TGAGVAAALV EQTVAVAETV RGDVVTV     117

SEQ ID NO: 12               moltype = AA   length = 147
FEATURE                     Location/Qualifiers
source                      1..147
                            mol_type = protein
                            organism = Aspergillus niger
SEQUENCE: 12
MPLTPEQIKI IKATVPVLQE YGTKITTAFY MNMSTVHPEL NAVFNTANQV KGHQARALAG    60
ALFAYASHID DLGALGPAVE LICNKHASLY IQADEYKIVG KYLLEAMKEV LGDACTDDIL   120
DAWGAAYWAL ADIMINREAA LYKQSQG                                       147

SEQ ID NO: 13               moltype = AA   length = 165
FEATURE                     Location/Qualifiers
source                      1..165
                            mol_type = protein
                            organism = Zea mays
SEQUENCE: 13
MALAEADDGA VVFGEEQEAL VLKSWAVMKK DAANLGLRFF LKVFEIAPSA EQMFSFLRDS    60
DVPLEKNPKL KTHAMSVFVM TCEAAAQLRK AGKVTVRETT LKRLGATHLR YGVADGHFEV   120
TGFALLETIK EALPADMWSL EMKKAWAEAY SQLVAAIKRE MKPDA                   165
```

```
SEQ ID NO: 14            moltype = AA   length = 169
FEATURE                  Location/Qualifiers
source                   1..169
                         mol_type = protein
                         organism = Oryza sativa
SEQUENCE: 14
MALVEGNNGV SGGAVSFSEE QEALVLKSWA IMKKDSANIG LRFFLKIFEV APSASQMFSF  60
LRNSDVPLEK NPKLKTHAMS VFVMTCEAAA QLRKAGKVTV RDTTLKRLGA THFKYGVGDA 120
HFEVTRFALL ETIKEAVPVD MWSPAMKSAW SEAYNQLVAA IKQEMKPAE            169

SEQ ID NO: 15            moltype = AA   length = 160
FEATURE                  Location/Qualifiers
source                   1..160
                         mol_type = protein
                         organism = Arabidopsis thaliana
SEQUENCE: 15
MESEGKIVFT EEQEALVVKS WSVMKKNSAE LGLKLFIKIF EIAPTTKKMF SFLRDSPIPA  60
EQNPKLKPHA MSVFVMCCES AVQLRKTGKV TVRETTLKRL GASHSKYGVV DEHFEVAKYA 120
LLETIKEAVP EMWSPEMKVA WGQAYDHLVA AIKAEMNLSN                      160

SEQ ID NO: 16            moltype = AA   length = 147
FEATURE                  Location/Qualifiers
source                   1..147
                         mol_type = protein
                         organism = Pisum sativum
SEQUENCE: 16
MGFTDKQEAL VNSSWESFKQ NLSGNSILFY TIILEKAPAA KGLFSFLKDT AGVEDSPKLQ  60
AHAEQVFGLV RDSAAQLRTK GEVVLGNATL GAIHVQRGVT DPHFVVVKEA LLQTIKKASG 120
NNWSEELNTA WEVAYDGLAT AIKKAMT                                    147

SEQ ID NO: 17            moltype = AA   length = 145
FEATURE                  Location/Qualifiers
source                   1..145
                         mol_type = protein
                         organism = Vigna unguiculata
SEQUENCE: 17
MVAFSDKQEA LVNGAYEAFK ANIPKYSVVF YTTILEKAPA AKNLFSFLAN GVDATNPKLT  60
GHAEKLFGLV RDSAAQLRAS GGVVADAALG AVHSQKAVND AQFVVVKEAL VKTLKEAVGD 120
KWSDELGTAV ELAYDELAAA IKKAY                                      145

SEQ ID NO: 18            moltype = AA   length = 161
FEATURE                  Location/Qualifiers
source                   1..161
                         mol_type = protein
                         organism = Vigna radiata
SEQUENCE: 18
MTTTLERGFT EEQEALVVKS WNVMKKNSGE LGLKFFLKIF EIAPSAQKLF SFLRDSTVPL  60
EQNPKLKPHA VSVFVMTCDS AVQLRKAGKV TVRESNLKKL GATHFRTGVA NEHFEVTKFA 120
LLETIKEAVP EMWSPAMKNA WGEAYDQLVD AIKYEMKPPS S                    161

SEQ ID NO: 19            moltype = AA   length = 154
FEATURE                  Location/Qualifiers
source                   1..154
                         mol_type = protein
                         organism = Sus scrofa
SEQUENCE: 19
MGLSDGEWQL VLNVWGKVEA DVAGHGQEVL IRLFKGHPET LEKFDKFKHL KSEDEMKASE  60
DLKKHGNTVL TALGGILKKK GHHEAELTPL AQSHATKHKI PVKYLEFISE AIIQVLQSKH 120
PGDFGADAQG AMSKALELFR NDMAAKYKEL GFQG                            154

SEQ ID NO: 20            moltype = AA   length = 154
FEATURE                  Location/Qualifiers
source                   1..154
                         mol_type = protein
                         organism = Equus caballus
SEQUENCE: 20
MGLSDGEWQQ VLNVWGKVEA DIAGHGQEVL IRLFTGHPET LEKFDKFKHL KTEAEMKASE  60
DLKKHGTVVL TALGGILKKK GHHEAELKPL AQSHATKHKI PIKYLEFISD AIIHVLHSKH 120
PGDFGADAQG AMTKALELFR NDIAAKYKEL GFQG                            154

SEQ ID NO: 21            moltype = AA   length = 124
FEATURE                  Location/Qualifiers
source                   1..124
                         mol_type = protein
                         organism = Synechocystis PCC6803
```

```
SEQUENCE: 21
MSTLYEKLGG TTAVDLAVDK FYERVLQDDR IKHFFADVDM AKQRAHQKAF LTYAFGGTDK    60
YDGRYMREAH KELVENHGLN GEHFDAVAED LLATLKEMGV PEDLIAEVAA VAGAPAHKRD   120
VLNQ                                                               124

SEQ ID NO: 22           moltype = AA  length = 183
FEATURE                 Location/Qualifiers
source                  1..183
                        mol_type = protein
                        organism = Synechococcus sp. PCC 7335
SEQUENCE: 22
MDVALLEKSF EQISPRAIEF SASFYQNLFH HHPELKPLFA ETSQTIQEKK LIFSLAAIIE    60
NLRNPDILQP ALKSLGARHA EVGTIKSHYP LVGQALIETF AEYLAADWTE QLATAWVEAY  120
DVIASTMIEG ADNPAAYLEP ELTFYEWLDL YGEESPKVRN AIATLTHFHY GEDPQDVQRD  180
SRG                                                                183

SEQ ID NO: 23           moltype = AA  length = 118
FEATURE                 Location/Qualifiers
source                  1..118
                        mol_type = protein
                        organism = Nostoc commune
SEQUENCE: 23
MSTLYDNIGG QPAIEQVVDE LHKRIATDSL LAPVFAGTDM VKQRNHLVAF LAQIFEGPKQ    60
YGGRPMDKTH AGLNLQQPHF DAIAKHLGER MAVRGVSAEN TKAALDRVTN MKGAILNK    118

SEQ ID NO: 24           moltype = AA  length = 146
FEATURE                 Location/Qualifiers
source                  1..146
                        mol_type = protein
                        organism = Vitreoscilla stercoraria
SEQUENCE: 24
MLDQQTINII KATVPVLKEH GVTITTTFYK NLFAKHPEVR PLFDMGRQES LEQPKALAMT    60
VLAAAQNIEN LPAILPAVKK IAVKHCQAGV AAAHYPIVGQ ELLGAIKEVL GDAATDDILD  120
AWGKAYGVIA DVFIQVEADL YAQAVE                                       146

SEQ ID NO: 25           moltype = AA  length = 131
FEATURE                 Location/Qualifiers
source                  1..131
                        mol_type = protein
                        organism = Corynebacterium sp.
SEQUENCE: 25
MTTSENFYDS VGGEETFSLI VHRFYEQVPN DDILGPMYPP DDFEGAEQRL KMFLSQYWGG    60
PKDYQEQRGH PRLRMRHVNY PIGVTAAERW LQLMSNALDV VDLTAEQREA IWEHMVRAAD  120
MLINSNPDPH A                                                       131

SEQ ID NO: 26           moltype = AA  length = 132
FEATURE                 Location/Qualifiers
source                  1..132
                        mol_type = protein
                        organism = Bacillus subtilis
SEQUENCE: 26
MGQSFNAPYE AIGEELLSQL VDTFYERVAS HPLLKPIFPS DLTETARKQK QFLTQYLGGP    60
PLYTEEHGHP MLRARHLPFP ITNERADAWL SCMKDAMDHV GLEGEIREFL FGRLELTARH  120
MVNQTEAEDR SS                                                      132

SEQ ID NO: 27           moltype = AA  length = 136
FEATURE                 Location/Qualifiers
source                  1..136
                        mol_type = protein
                        organism = Bacillus megaterium
SEQUENCE: 27
MREKIHSPYE LLGGEHTISK LVDAFYTRVG QHPELAPIFP DNLTETARKQ KQFLTQYLGG    60
PSLYTEEHGH PMLRARHLPF EITPSRAKAW LTCMHEAMDE INLEGPERDE LYHRLILTAQ  120
HMINSPEQTD EKGFSH                                                  136

SEQ ID NO: 28           moltype = AA  length = 399
FEATURE                 Location/Qualifiers
source                  1..399
                        mol_type = protein
                        organism = Saccharomyces cerevisiae
SEQUENCE: 28
MLAEKTRSII KATVPVLEQQ GTVITRTFYK NMLTEHTELL NIFNRTNQKV GAQPNALATT    60
VLAAAKNIDD LSVLMDHVKQ IGHKHRALQI KPEHYPIVGE YLLKAIKEVL GDAATPEIIN  120
AWGEAYQAIA DIFITVEKKM YEEALWPGWK PFDITAKEYV ASDIVEFTVK PKFGSGIELE  180
SLPITPGQYI TVNTHPIRQE NQYDALRHYS LCSASTKNGL RFAVKMEAAR ENFPAGLVSE  240
YLHKDAKVGD EIKLSAPAGD FAINKELIHQ NEVPLVLLSS GVGVTPLLAM LEEQVKCNPN  300
RPIYWIQSSY DEKTQAFKKH VDELLAECAN VDKIIVHTDT EPLINAAFLK EKSPAHADVY  360
TCGSLAFMQA MIGHLKELEH RDDMIHYEPF GPKMSTVQV                         399
```

```
SEQ ID NO: 29          moltype = AA  length = 152
FEATURE                Location/Qualifiers
source                 1..152
                       mol_type = protein
                       organism = Nicotina tobaccum
SEQUENCE: 29
MSSFSEEQEA LVLKSWDSMK KNAGEWGLKL FLKIFEIAPS AKKLFSFLKD SNVPLEQNAK    60
LKPHAKSVFV MTCEAAVQLR KAGKVVVRDS TLKKLGAAHF KYGVADEHFE VTKFALLETI   120
KEAVPDMWSV DMKNAWGEAF DQLVNAIKTE MK                                 152

SEQ ID NO: 30          moltype = AA  length = 160
FEATURE                Location/Qualifiers
source                 1..160
                       mol_type = protein
                       organism = Medicago sativa
SEQUENCE: 30
MGTLDTKGFT EEQEALVVKS WNAMKKNSAE LGLKLFLKIF EIAPSAQKLF SFLKDSKVPL    60
EQNTKLKPHA MSVFLMTCES AVQLRKSGKV TVRESSLKKL GANHFKYGVV DEHFEVTKFA   120
LLETIKEAVP EMWSPAMKNA WGEAYDQLVN AIKSEMKPSS                         160

SEQ ID NO: 31          moltype = AA  length = 161
FEATURE                Location/Qualifiers
source                 1..161
                       mol_type = protein
                       organism = Glycine max
SEQUENCE: 31
MTTTLERGFS EEQEALVVKS WNVMKKNSGE LGLKFFLKIF EIAPSAQKLF SFLRDSTVPL    60
EQNPKLKPHA VSVFVMTCDS AVQLRKAGKV TVRESNLKKL GATHFRTGVA NEHFEVTKFA   120
LLETIKEAVP EMWSPAMKNA WGEAYDQLVD AIKSEMKPPS S                       161
```